US006835557B1

(12) United States Patent
Weissmann

(10) Patent No.: US 6,835,557 B1
(45) Date of Patent: Dec. 28, 2004

(54) DNA SEQUENCES, RECOMBINANT DNA MOLECULES AND PROCESSES FOR PRODUCING HUMAN INTERFERON-LIKE POLYPEPTIDES

(75) Inventor: Charles Weissmann, Zurich (CH)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 08/487,280

(22) Filed: Jun. 7, 1995

Related U.S. Application Data

(60) Division of application No. 06/223,108, filed on Jan. 7, 1981, now abandoned, which is a continuation-in-part of application No. 06/118,084, filed on Feb. 4, 1980, now Pat. No. 4,530,901.

(30) Foreign Application Priority Data

| | | |
|---|---|---|
| Jan. 8, 1980 | (EP) | 80300079 |
| Apr. 3, 1980 | (EP) | 80301100 |
| Oct. 2, 1980 | (GB) | 8031737 |

(51) Int. Cl.[7] .................................................. C12P 19/34

(52) U.S. Cl. .............. 435/91.1; 435/252.3; 435/252.33; 435/325; 435/254.11; 435/254.2; 435/320.1; 536/23.52

(58) Field of Search ........................... 435/69.51, 240.1, 435/252.3–252.35, 325, 235, 254.11, 254.2, 320.1; 536/23.52

(56) References Cited

U.S. PATENT DOCUMENTS

| | | | | |
|---|---|---|---|---|
| 3,699,222 A | | 10/1972 | Isaacs et al. | 424/85.4 |
| 4,184,917 A | | 1/1980 | Dorner et al. | 435/68.1 |
| 4,190,495 A | | 2/1980 | Curtiss, III | 435/172.3 |
| 4,237,224 A | | 12/1980 | Cohen et al. | 435/69.1 |
| 4,241,174 A | | 12/1980 | Familletti et al. | 435/5 |
| 4,262,090 A | | 4/1981 | Colby, Jr. et al. | 435/91.33 |
| 4,530,901 A | * | 7/1985 | Weissmann | 435/69.51 |
| 6,482,613 B1 | * | 11/2002 | Goeddel et al. | 435/69.51 |

FOREIGN PATENT DOCUMENTS

| | | |
|---|---|---|
| DE | 2724918 | 12/1978 |
| DE | 2930604 | 2/1980 |
| EP | 0001929 | 11/1978 |
| EP | 0018218 | 4/1979 |
| EP | 0011560 | 5/1980 |
| EP | 28033 | 10/1980 |
| EP | 0020147 | 12/1980 |
| GB | 1412591 | 11/1975 |
| GB | 1568047 | 5/1978 |
| GB | 1521032 | 8/1978 |
| GB | 2019408 | 10/1979 |
| GB | 2027033 | 2/1980 |
| GB | 2031434 | 4/1980 |
| GB | 2033905 | 5/1980 |
| GB | 2034323 | 6/1980 |
| GB | 2034717 | 6/1980 |
| GB | 2037296 | 7/1980 |

OTHER PUBLICATIONS

Abstracts, Conference On Regulatory Functions Of Interferons, New York Academy of Sciences (Oct. 23–26, 1979).
"Purification Of Interferon mRNA By Hybridizing Induced Material to cDNA", *Research Disclosure*, No. 183009, pp. 361–362 (Jul. 1979).
R. Ambler et al., "Partial Amino Acid Sequence of Penicillinase Coded By *Escherichia coli* Plasmid R6K", *Proc. Natl. Acad. Sci. USA*, 75, pp. 3732–3736 (Aug. 1978).
P. Beverley et al., "Killing Comes Naturally", *Nature*, 278, pp. 119–120 (Mar. 8, 1979).
F. Bolivar et al., "Construction And Characterization Of New Cloning Vehicles II. A Multipurpose Cloning System", *Gene*, 2, pp. 95–113 (1977).
P. Bridgen et al., "Human Lymphoblastoid Interferon", *J. Biol. Chem.*, 252, pp. 6585–6587 (1977).
S. Broome et al., "Immunological Screening Method To Detect Specific Translation Products", *Proc. Natl. Acad. Sci. USA*, 75, pp. 2746–2749 (Jun. 1978).
C. Burrell et al., "Expression In *Escherichia coli* of Hepatitis B Virus DNA Sequences Cloned In Plasmid pBR322", *Nature*, 279, pp. 43–47 (May 3, 1979).
M. Casadaban et al., "Lactose Genes Fused To Exogenous Promoters In One Step Using A Mu–Lac Bacteriophage: In Vivo Probe For Transcriptional Control Sequences", *Proc. Natl. Acad. Sci. USA*, 76, pp. 4530–4533 (Sep. 1979).
R. Cavalieri et al., "Synthesis Of Human Interferon By Xenopus Laevis Oocytes: Two Structural Genes For Interferons In Human Cells", *Proc. Natl. Acad. Sci. USA*, 74, pp. 3287–3291 (Aug. 1977).
A.C.Y. Chang et al., "Phenotypic Expression In *E. coli* Of A DNA Sequence Coding For Mouse Dihydrofolate Reductase", *Nature*, 275, pp. 617–624 (Oct. 19, 1978).
P. Farrell et al., "Interferon Action: Two Distinct Pathways For Inhibition Of Protein Synthesis By Double–Stranded RNA", *Proc. Natl. Acad. Sci. USA*, 75, pp. 5893–5897 (Dec. 1978).
T.H. Fraser et al., "Chicken Ovalbumin Is Synthesized And Secreted By *Escherichia coli", Proc. Natl. Acad. Sci. USA*, 75, pp. 5936–5940 (Dec. 1978).

(List continued on next page.)

*Primary Examiner*—James Martinell
(74) *Attorney, Agent, or Firm*—James F. Haley, Jr.; Jennifer T. Weissman; Connie Wong

(57) ABSTRACT

DNA sequences, recombinant DNA molecules and hosts transformed with them which produce polypeptides displaying a biological or immunological activity of human interferon, the genes coding for these polypeptides and methods of making and using these molecules, hosts, genes and polypeptides. The DNA sequences are characterized in that they code for a polypeptide displaying a biological or immunological activity of human interferon. In appropriate hosts these DNA sequences and recombinant DNA molecules permit the production and identification of genes and polypeptides displaying a biological or immunological activity of human interferon and their use in antiviral and antitumor or anticancer agents.

27 Claims, 31 Drawing Sheets

OTHER PUBLICATIONS

A. Fritsch et al., "Clonage Du Génome Du Virus De L'hepatite B Dans *Escherichia coli", C. R. Acad. Sc. Paris*, 287, Série D. pp. 1453–1456 (Dec. 18, 1978).

J. Fujisawa et al., "Nonglycosylated Mouse L Cell Interferon Produced By The Action Of Tunicamycin", *J. Biol. Chem.*, 253, pp. 8677–8679 (1978).

D. Goeddel et al., "Direct Expression In *Escherichia coli* Of A DNA Sequence Coding For Human Growth Hormone", *Nature*, 281, pp. 544–548 (Oct. 18, 1979).

D. Goeddel et al., "Expression In *Escherichia coli* Of Chemically Synthesized Genes For Human Insulin", *Proc. Natl. Acad. Sci. USA*, 76, pp. 106–110 (Jan. 1979).

M. Grunstein et al., "Colony Hybridization: A Method For The Isolation Of Cloned DNAs That Contain A Specific Gene", *Proc. Natl. Acad. Sci. USA*, 72, pp. 3961–3965 (Oct. 1975).

E. Havell et al., "Altered Molecular Species Of Human Interferon Produced In The Presence Of Inhibitors Of Glycosylation", *J. Biol. Chem.*, 252, pp. 4425–4427 (1977).

R. Herberman et al., "Augmentation By Interferon Of Human Natural And Antibody–Dependent Cell–Mediated Cytotoxicity", *Nature*, 277, pp. 221–223 (Jan. 18, 1979).

K. Itakura et al., "Expression In *Escherichia coli* Of A Chemically Synthesized Gene For The Hormone Somatostatin", *Science*, 198, pp. 1056–1063 (Dec. 9, 1977).

I. Kerr et al., "ppA2'p5'A2'p5'A: An Inhibitor Of Protein Synthesis Synthesized With An Enzyme Fraction From Interferon–Treated Cells", *Proc. Natl. Acad. Sci. USA*, 75, pp. 256–260 (Jan. 1978).

E. Knight, Jr., "Interferon: Purification And Initial Characterization From Human Diploid Cells", *Proc. Natl. Acad. Sci. USA*, 73, pp. 520–523 (Feb. 1976).

J. Lewis et al., "Dual Action Of Double–Stranded RNA In Inhibiting Protein Synthesis In Extracts Of Interferon–Treated Mouse L Cells", *Eur. J. Biochem.*, 86, pp. 497–509 (1978).

J. Martial et al., "Human Growth Hormone: Complementary DNA Cloning And Expression In Bacteria", *Science*, 205, pp. 602–606 (Aug. 10, 1979).

A. Maxam et al., "A New Method For Sequencing DNA", *Proc. Natl. Acad. Sci. USA*, 74, pp. 560–564 (Feb. 1977).

O. Mercereau–Puijalon et al., "Synthesis Of An Ovalbumin–Like Protein By *Escherichia coli* K12 Harbouring A Recombinant Plasmid", *Nature*, 275, pp. 505–510 (Oct. 12, 1978).

S. Nagata et al., "Synthesis In *E. coli* Of A Polypeptide With Human Leukocyte Interferon Activity", *Nature*, 284, pp. 316–320 (Mar. 27, 1980).

A. Rosenfeld, "Interferon: The Next Wonder Therapy?", *The Reader's Digest*, pp. 130–133 (Nov. 1979).

M. Rubinstein et al., "Human Leukocyte Interferon Purified To Homogeneity", *Science*, 202, pp. 1289–1290 (Dec. 22, 1978).

M. Rubinstein et al., "Human Leukocyte Interferon: Production Purification To Homogeneity, And Initial Characterization", *Proc. Natl. Acad. Sci. USA*, 76, pp. 640–644 (Feb. 1979).

P.H. Seeburg et al., "Synthesis Of Growth Hormone By Bacteria", *Nature*, 276, pp. 795–798 (Dec. 21/28, 1978).

J. Shine et al., "Construction And Analysis Of Recombinant DNA For Human Chorionic Somatomammotropin", *Nature*, 270, pp. 494–499 (Dec. 8, 1977).

J. Sutcliffe, "Nucleotide Sequence Of The Ampicillin Resistant Gene Of *Escherichia coli* Plasmid pBR322", *Proc. Natl. Acad. Sci. USA*, 75, pp. 3737–3741 (Aug. 1978).

T. Taniguchi et al., "Construction And Identification Of A Bacterial Plasmid Containing The Human Fibroblast Interferon Gene Sequence", *Proc. Japan. Acad.*, 55, Ser. B, pp. 464–469 (1979).

J. Treuner et al., "Successful Treatment Of Nasopharyngeal Carcinoma With Interferon", preprint.

L. Villa–Komaroff et al., "A Bacterial Clone Synthesizing Proinsulin", *Proc. Natl. Acad. Sci. USA*, 75, pp. 3727–3731 (Aug. 1978).

R. Wagner, "Biological Studies Of Interferon I. Supression Of Cellular Infection With Eastern Equine Encephalomyelitis Virus", *Virology*, 13, pp. 323–337 (1961).

K. Zoon, "Amino Terminal Sequence Of The Major Component Of Human Lymphoblastoid Interferon", *Science*, 207, pp. 527–528 (Feb. 1, 1980).

Report "International Workshop On Interferon In The Treatment of Cancer", (Mar.–Apr. 1975).

Berg et al., Conference On Regulatory Functions Of Interferons Abstract No. I9 (1979).

R. J. Britten and E. H. Davidson, "Repetitive And Non–Repetitive DNA Sequences And A Speculation On The Origins Of Evolutionary Novelty", *The Quarterly Review of Biology*, 46, pp. 111–133 (Jun. 1971).

D. Goeddel et al., "The Structure Of Eight Distinct Cloned Human Leukocyte Interferon cDNAs", *Nature*, 290 pp. 20–26 (1981) ("Goeddel III").

D. E. Kennell, "Principles and Practices of Nucleic Acid Hybridization", *Progr. Nucl. Acid. Res. Mol. Biol.*, 11, pp. 259–301 (1971).

N. Mantei et al., "The Nucleotide Sequence Of A Cloned Human Leukocyte Interferon cDNA", *Gene*, 10, pp. 1–10 (May 1980).

S. Nagata et al., "The Structure Of One Of The Eight Or More Distinct Chromosomal Genes For Human Interferon–α", *Nature*, 2 pp. 401–408 (Oct. 1980) ("Nagata II").

F. Rougeon et al., "Insertion Of A Rabbit β–globin Gene Sequence In An *E. coli* Plasmid", *Nucl. Acids Res.*, 2, pp. 2365–2378 (Dec. 1975).

W. E. Stewart et al., Comparisons Of Several Biological And Physiochemical Properties Of Human Leukocyte Interferons Prod By Human Leukocyte And *E. coli, Gene*, 11, pp. 181–186 (1980) Chemical Abstracts, 94: 63542q, p. 550 (Mar. 1981).

M. Streuli et al., "At Least Three Human Type α–Interferons: Structure Of α2", *Science*, 209, pp. 1343–1347 (1980) [Chemical Abstracts, 93: 236612x, p. 624 (Dec. 1980].

T. Taniguchi et al., "Human Leukocyte And Fibroblast Interferon Are Structurally Related", *Nature*, 285, pp. 547–549 (Jun. 1980) ("Taniguchi II").

C. Weissmann, "The Cloning Of Interferon And Other Mistakes", *Interferon* (London), 3, pp. 101–134 (1981).

* cited by examiner

```
                                 10                                  20
        MetSerIleGlnHisPheArgValAlaLeuIleProPhePheAlaAlaPheCysLeuProValPheAlaHisProGluThr
pBR322  ATGAGTATTCAACATTTCCGTGTCGCCCTTATTCCCTTTTTTGCGGCATTTTGCCTTCCTGTTTTTGCTCACCCAGAAACG

           29      181
        LeuVal     ProAlaAlaMet
        CTGGTG ••• CCTGCAGCAATG •••
                     Pst

                                                                                          24
        MetSerIleGlnHisPheArgValAlaLeuIleProPhePheAlaAlaPheCysLeuProValPheAlaHisArgCysSerAsn
pKT279  ATGAGTATTCAACATTTCCGTGTCGCCCTTATTCCCTTTTTTGCGGCATTTTGCCTTCCTGTTTTTGCTCACCGCTGCAGCAATG •••
                                                                                          Pst

                                                                                             25
        MetSerIleGlnHisPheArgValAlaLeuIleProPhePheAlaAlaPheCysLeuProValPheAlaHisProLeuGlnGln
pKT280  ATGAGTATTCAACATTTCCGTGTCGCCCTTATTCCCTTTTTTGCGGCATTTTGCCTTCCTGTTTTTGCTCACCCGCTGCAGCAATG •••
                                                                                             Pst

                                                                                        27
        MetSerIleGlnHisPheArgValAlaLeuIleProPhePheAlaAlaPheCysLeuProValPheAlaHisProGluThr •••
pKT287  ATGAGTATTCAACATTTCCGTGTCGCCCTTATTCCCTTTTTTGCGGCATTTTGCCTTCCTGTTTTTGCTCACCCAGAAACG •••

        AlaAlaAlaMet
        GCTGCAGCAATG •••
          Pst
```

FIG. 6

50 60 70
270 280 290 300 310 320 330 340 350
GLNLYSALAPROALAILESERVALLEUHISGLULEUILEGLNGLNILEPHEASNLEUPHETHRTHRLYSASPSERSERALAALATRPASP
CAGAAGGCTCCAGCCATCTCTGTCCTCCATGAGCTGATCCAGCAGATCTTCAACCTCTTTACCACAAAAGATTCATCTGCTGCTTGGGAT
AluMbo I EcoP15 Bgl II Mbo I Mbo II Hinf 80 90 100
360 370 380 390 400 410 420 430 440
GLUASPLEULEUASPLYSPHECYSTHRGLULEUTYRGLNGLNLEUASNASPLEUGLUALACYSVALMETGLNGLUGLUARGVALGLYGLU
GAGGACCTCCTAGACAAATTCTGCACCGAACTCTACCAGCAGCTGAATGACTTGGAAGCCTGTGTGATGCAGGAGGAGAGGGTGGGAGAA
Ava I EcoP15 Pvu II Alu I Sfa NI 110 120 130
450 460 470 480 490 500 510 520 530
THRPROLEUMETASNALAASPSERILELEUALAVALLYSLYSTYRPHEARGARGILETHRLEUTYRLEUTHRGLULYSLYSTYRSERPRO
ACTCCCCTGATGAATGCGGACTCCATCTTGGCTGTGAAGAAATACTTCCGAAGAATCACTCTCTATCTGACAGAGAAGAAATACAGCCCT
Hinf Mbo II Mbo II Hinf Mbo II

CYSALATRPGLUVALVALARGALAGLUILEMETARGSERLEUSERLEUSERTHRASNLEUGLNGLUARGLEUARGARGLYSGLU

TGTGCCTGGGAGGTTGTCAGAGCAGAAATCATGAGATCCCTCTCTTTATCAACAAACTTGCAAGAAAGATTAAGGAGGAAGGAATAACAT

EcoRII MboII 630 640 650 660 670 680 690 700 710

CTGGTCCAACATGAAAACAATTCTTATTGACTCATACACCAGGTCACGCTTTCATGAATTCTGTCATTTCAAAGACTCTCACCCCTGCTA

AvaII Hinf EcoRII EcoRI Hinf Hph 720 730 740 750 760 770 780 790 800

TAACTATGACCATGCTGATAAACTGATTTATCTATTTAAATATTTATTTAACTATTCATAAGATTTAAATTATTTTTGTTCATATAACGT 810 820 830 840 850 860 865

CATGTGCACCTTTACACTGTGGTTAGTGTAATAAAACATGTTCCTTATATTTACTCAAAAAAAC$_{15}$

AccI

FIG. 10

```
                                                                                    -50         -40
206(II)                                                                       G13.TTACTGGTGGCCCTC.
                                                                                leu  leu  val  ala  leu

                                                                       -20
                                                              met  ala  ser  pro  phe  ala  leu  leu  met  val  leu
2h(I)   G23CTCTAGGTTCAGAGTCACCCATCTCAGCAAGCCCAGAAGTATCTGCAATATCTACGATGGCCTCGCCCTTTGCTTTACTGATGGTCCTG.
           -120     -110     -100     -90      -80      -70      -60      -50      -40

           -30      -20      -10      1        10       20       30       40       50
206(II) .CTGGTGCTCAGCTGCAAGTCAAGCTGCTCTGTGGGCTGTGATCTGCCTCAAACCCACAGCCTGGGTAGCAGGAGGACCTTGATGCTCCTG.
         leu val leu ser cys lys ser ser cys ser val gly CYS ASP LEU PRO GLN THR HIS SER LEU GLY SER ARG ARG THR LEU MET LEU LEU

            -10                         -1  1                     10

         val val leu ser cys lys ser ser cys ser leu gly CYS ASP LEU PRO GLU THR HIS SER LEU ASP ASN ARG ARG THR LEU MET LEU LEU
2h(I)   .GTGGTGCTCAGCTGCAAGTCAAGCTGCTCTCTGGGCTGTGATCTCCCTGAGACCCACAGCCTGGATAACAGGAGGACCTTGATGCTCCTG.
           -30      -20      -10      1        10       20       30       40       50
```

*FIG. 12*

```
         60        70        80        90        100       110       120          130       140
206(II)  GCACAGATGAGGAGAATCTCTCTTTTCTCCTGCTTGAAGGACAGACATGACTTTGGATTTCCCCAGGAGGAGTTT---GGCAACCAGTTC
         ALA GLN MET ARG ARG ILE SER LEU PHE SER CYS LEU LYS ASP ARG HIS ASP PHE GLY PHE PRO GLN GLU GLU PHE - GLY ASN GLN PHE

         20                            30                            40

         ALA GLN MET SER ARG ILE SER PRO SER SER CYS LEU MET ASP ARG HIS ASP PHE GLY PHE PRO GLN GLU GLU PHE ASP GLY ASN GLN PHE
2h(I)    GCACAAATGAGCAGAATCTCTCCTTCCTCCTGTCTGATGGACAGACATGACTTTGGATTTCCCCAGGAGGAGTTTGATGGCAACCAGTTC
         60        70        80        90        100       110       120          130       140


         150       160       170       180       190       200       210       220       230
206(II)  CAAAAGGCTGAAACCATCCCTGTCCTCCATGAGATGATCCAGCAGATCTTCAATCTCTTCAGCACAAAGGACTCATCTGCTGCTTGGGAT
         GLN LYS ALA GLU THR ILE PRO VAL LEU HIS GLU MET ILE GLN GLN ILE PHE ASN LEU PHE SER THR LYS ASP SER SER ALA ALA TRP ASP
         50                            60                            70

         50                            60                            70
         GLN LYS ALA PRO ALA ILE SER VAL LEU HIS GLU LEU ILE GLN GLN ILE PHE ASN LEU PHE THR THR LYS ASP SER SER ALA ALA TRP ASP
2h(I)    CAGAAGGCTCCAGCCATCTCTGTCCTCCATGAGCTGATCCAGCAGATCTTCAACCTCTTTACCACAAAAGATTCATCTGCTGCTTGGGAT
         150       160       170       180       190       200       210       220       230
```

FIG. 13

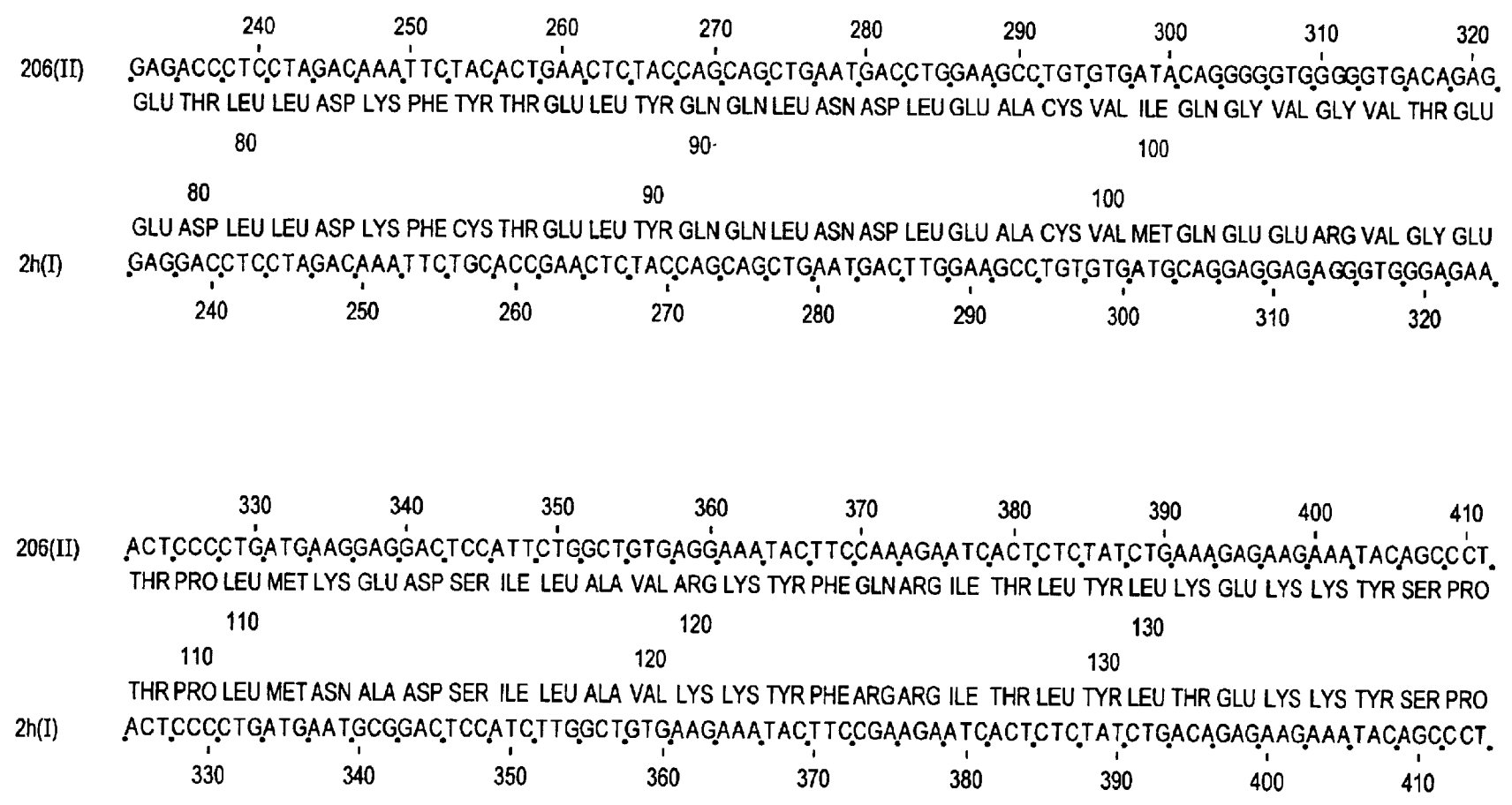

```
            240       250       260       270       280       290       300       310       320
206(II) GAGACCCTCCTAGACAAATTCTACACTGAACTCTACCAGCAGCTGAATGACCTGGAAGCCTGTGTGATACAGGGGGTGGGGGTGACAGAG
        GLU THR LEU LEU ASP LYS PHE TYR THR GLU LEU TYR GLN GLN LEU ASN ASP LEU GLU ALA CYS VAL ILE GLN GLY VAL GLY VAL THR GLU
            80                            90                            100

        80                            90                            100
        GLU ASP LEU LEU ASP LYS PHE CYS THR GLU LEU TYR GLN GLN LEU ASN ASP LEU GLU ALA CYS VAL MET GLN GLU GLU ARG VAL GLY GLU
2h(I)   GAGGACCTCCTAGACAAATTCTGCACCGAACTCTACCAGCAGCTGAATGACTTGGAAGCCTGTGTGATGCAGGAGGAGAGGGTGGGAGAA
        240       250       260       270       280       290       300       310       320

            330       340       350       360       370       380       390       400       410
206(II) ACTCCCCTGATGAAGGAGGACTCCATTCTGGCTGTGAGGAAATACTTCCAAAGAATCACTCTCTATCTGAAAGAGAAGAAATACAGCCCT
        THR PRO LEU MET LYS GLU ASP SER ILE LEU ALA VAL ARG LYS TYR PHE GLN ARG ILE THR LEU TYR LEU LYS GLU LYS LYS TYR SER PRO
            110                           120                           130

        110                           120                           130
        THR PRO LEU MET ASN ALA ASP SER ILE LEU ALA VAL LYS LYS TYR PHE ARG ARG ILE THR LEU TYR LEU THR GLU LYS LYS TYR SER PRO
2h(I)   ACTCCCCTGATGAATGCGGACTCCATCTTGGCTGTGAAGAAATACTTCCGAAGAATCACTCTCTATCTGACAGAGAAGAAATACAGCCCT
        330       340       350       360       370       380       390       400       410
```

FIG. 14

```
           420       430       440       450       460       470       480       490       500
206(II)  TGTGCCTGGGAGGTTGTCAGAGCAGAAATCATGAGATCTTTTTCTTTGTCAACAAACTTGCAAGAAAGTTTAAGAAGTAAGGAATGAAAA
         CYS ALA TRP GLU VAL VAL ARG ALA GLU ILE MET ARG SER PHE SER LEU SER THR ASN LEU GLN GLU SER LEU ARG SER LYS GLU
           140                     150                     160       165

         140                     150                     160       166
         CYS ALA TRP GLU VAL VAL ARG ALA GLU ILE MET ARG SER LEU SER LEU SER THR ASN LEU GLN GLU ARG LEU ARG ARG LYS GLU
2h(I)    TGTGCCTGGGAGGTTGTCAGAGCAGAAATCATGAGATCCCTCTCTTTATCAACAAACTTGCAAGAAAGATTAAGGAGGAAGGAATAACAT
           420       430       440       450       460       470       480       490       500

           510       520       530       540       550       560       570       580
206(II)  CTGGTTCAACATGGAAATGATTTTCATTGATTCGTATGCCAGCTCACCTTTTTATGA--TCTGCCATTTCAAAGACTCATGTTTCTGCTA

2h(I)    CTGGTCCAACATGAAAACAATTCTTATTGACTCATACACCAGGTCACGCTTTCATGAATTCTGTCATTTCAAAGACTCTCACCCCTGCTA
           510       520       530       540       550       560       570       580       590
```

206(II) TGACCATGACACGATTTAAATCTTTTCAAATGTTTTTAGGAGTATTAATCAACATTGTATTCAGCTCTTAAGGCACTAGTCCCTTACAGAG

2h(I) TAACTATGACCATGCTGATAAACTGATTTATCTATTTAAATATTTATTTAACTATTCATAAGATTTAAATTATTTTTGTTCATATAACGTC 600 610 620 630 640 650 660 670 680

690

206(II) GACCATGCTGAC$_{29}$

2h(I) ATGTGCACCTTTACACTGTGGTTAGTGTAATAAAACATGTTCCTTATATTTACTCAAAAAAAC$_{15}$ 690 700 710 720 730 740

*FIG. 16*

PARTIAL RESTRICTION MAPS OF CLONED, IFN-α RELATED CHROMOSOMAL DNA SEGMENTS

E: Eco RI, Ba: Bam HI, Bg: Bgl II, Hinc III, T: Tac I 110 120 130
400 420 440 460 480
*THRPROLEUMETASNALAASPSERILELEUALAVALLYSLYSTYRPHEARGARGILETHRLEUTYRLEUTHRGLULYSLYSTYRSERPRO*
ACTCCCCTGATGAATGCGGACTCCATCTTGGCTGTGAAGAAATACTTCCGAAGAATCACTCTCTATCTGACAGAGAAGAAATACAGCCCT
Hinf Mbo II Mbo II Hinf Mbo II 140 150 160 166
500 520 540 560
*CYSALATRPGLUVALVALARGALAGLUILEMETARGSERLEUSERLEUSERTHRASNLEUGLNGLUARGLEUARGARGLYSGLU*
TGTGCCTGGGAGGTTGTCAGAGCAGAAATCATGAGATCCCTCTCTTTATCAACAAACTTGCAAGAAAGATTAAGGAGGAAGGAATAACAT
Eco RII Mbo I 580 600 620 640 660
CTGGTCCAACATGAAAACAATTCTTATTGACTCATACACCAGGTCACGCTTTCATGAATTCTGTCATTTCAAAGACTCTCACCCCTGCTA
Ava II Hinf Eco RII Eco RI Hinf Hph 680 700 720 740
TAACTATGACCATGCTGATAAACTGATTTATCTATTTAAATATTTATTTAACTATTCATAAGATTTAAATTATTTTTGTTCATATAACGT 760 780 800 820 840
CATGTGCACCTTTACACTGTGGTTAGTGTAATAAAACATGTTCCTTATATTTACTCAATCCATTATTTTGTGTTGTTCATTAAACTTTTA
Hgi A

*FIG. 22*

```
                860                 880                 900                 920
                 |                   |                   |                   |
CTATAGGAACTTCCTGTATGTGTTCATTCTTTAATATGAAATTCCTAGCCTGACTGTGCAACCTGATTAGAGAATAAAGGGTATATTTTA

      940                959
       |                  |
TTTGCTTATCATTATTATATGTAAGA
```

FIG. 23

CONSTRUCTION OF PLASMID LAC-AUG(α-2)

160 180 200
$C_{24}$AATGCAAATAGCTTATATTATATGATTTATTTCTAGTAAA
AluI 220 240 260 280 300
GTTATTCAACACATCAGTACTTATGTCAACTGCTGAAAAGAAAAAAGTGTTGGCAACATCTGGATGAATACTGCAGCTGATGAAGTTTACAAATTATTTT
RsaI ChuII PstI AluI PvuII BbrsII 320 340 360 380 400
GTCATATAAAGCAAAATTCAAAGCTTCATACACTAAGAGAAAAATTTTAAAAAATTATTCATTCATATTTTTAGGAGTTTTGAATGATTGGATATGTAAT
EcoRI BbrI AluI DdeI EcoRI 420 440 460 480 500
TATATTCATATTATTAATGTGTATCTATATAGATTTTTATTTTGCATATGTACTTTGATACAAAATTTACATGAACAAATTACACTAAAGTTATTCCACA
EcoRI RsaI EcoRI 520 540 560 580 600
ATATACTTATCAAATTAAGTTAATGTCAATAGCTTTTAAACTTAAATTTTAGTTTAGTTAGCTTTTCTGTCATTCTTACTTACTTTGAATAAAAAGAGCA
AluI EcoRI AluI

FIG. 29

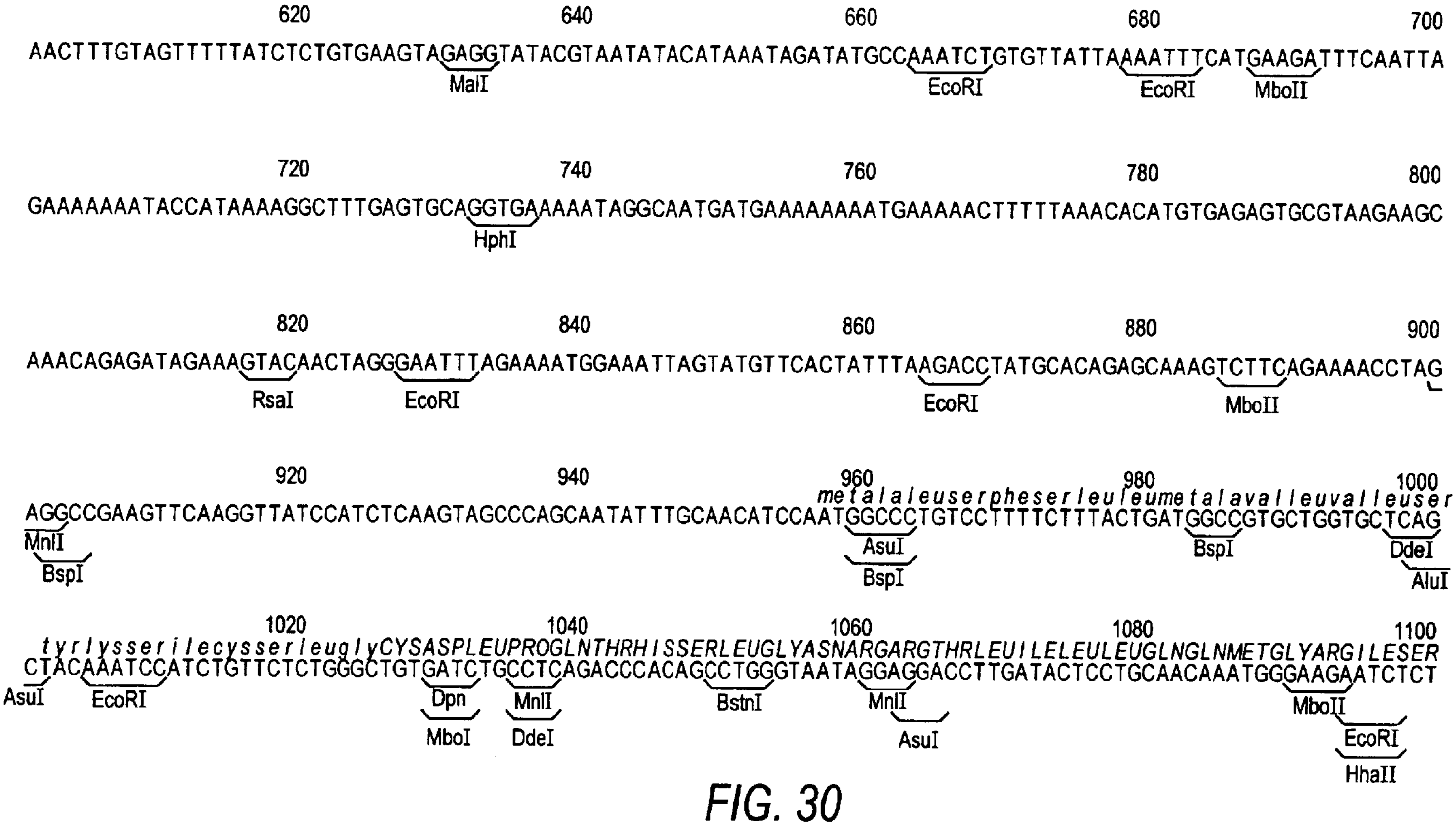

FIG. 30

```
                                                                                              700
AACTTTGTAGTTTTTATCTCTGTGAAGTAGAGGTATACGTAATATACATAAATAGATTAGCCAAATCTGTGTTATTAAAATTTCATGAAGATTCAATTA
                                620            640                660                680  ‾‾‾‾‾‾  ‾‾‾‾‾‾
                                                                                    MaII         EcoRI   MboII

                                                                                              800
GAAAAAATACCATAAAGGCTTTGAGTGCAGGTGAAAAATAGGCAATGATGAAAAAAACTTTTAAACACATGTGAGAGTGCGTAAGAAGC
      720             740                760                780
                                        ‾‾‾‾‾‾
                                         HphI

                                                                                              900
AAACAGAGATAGAAGTACAACTAGGGAATTTAGAAAAATGGAAATTAGTATGTTCACTATTTAAGACCTATGCACAGAGCAAAGTCTTCAGAAAACCTAG
      820                840                860                880
‾‾‾‾‾‾   ‾‾‾‾‾‾                                                                       ‾‾‾‾‾‾
 RsaI    EcoRI                                                                         MboII

                                           met ala leu ser phe ser leu phe leu val leu val leu ser
AGGCCGAAGTTCAAGGTTATCCATCTCAAGTAGCCCCAGCAATATTTGCAACATCCAATGGCCCTGTCCTTTTCTTTACTGATGGCCGTGCTGGTGCTCAG
      920                940                960                980               1000
‾‾‾‾‾‾              ‾‾‾‾‾‾ ‾‾‾‾‾‾                     ‾‾‾‾‾‾                                   ‾‾‾‾‾‾
 MnlI                 DpnI  MnlI                       AsuI                                     DdeI
 BspI                 MboI  DdeI                       BspI                                     AluI

       tyr lys ser ile gly ser leu glu gly lys CYS SER ALA SER PRO LEU GLU PRO ARG GLY LEU ASN THR HIS HIS HIS SER SER GLU ARG LEU GLU UGL ASN ARG ARG GLY ARG GLY THR HIS LEU ILE LEU GLU LEU GLU GLY LEU ASN MET GLY LEU TYR ARG GLY ILE LEU GLU SER ER
CTACAAATCCATCCGTTCTCTGGGCGTGATCTGCCTGCAGACCCCAGACCCCACAGCCGCCTCAGAACCTTGATACTCCTGAACTAATGGGAAGAATCTCT
          1020               1040               1060                1080                1100
‾‾‾‾‾‾             ‾‾‾‾‾‾     ‾‾‾‾‾‾      ‾‾‾‾‾‾              ‾‾‾‾‾‾              ‾‾‾‾‾‾     ‾‾‾‾‾‾
 AsuI               EcoRI      BstNI       MnlI                AsuI                MboII      EcoRI
                                                                                              HhaII
```

Figure 31:
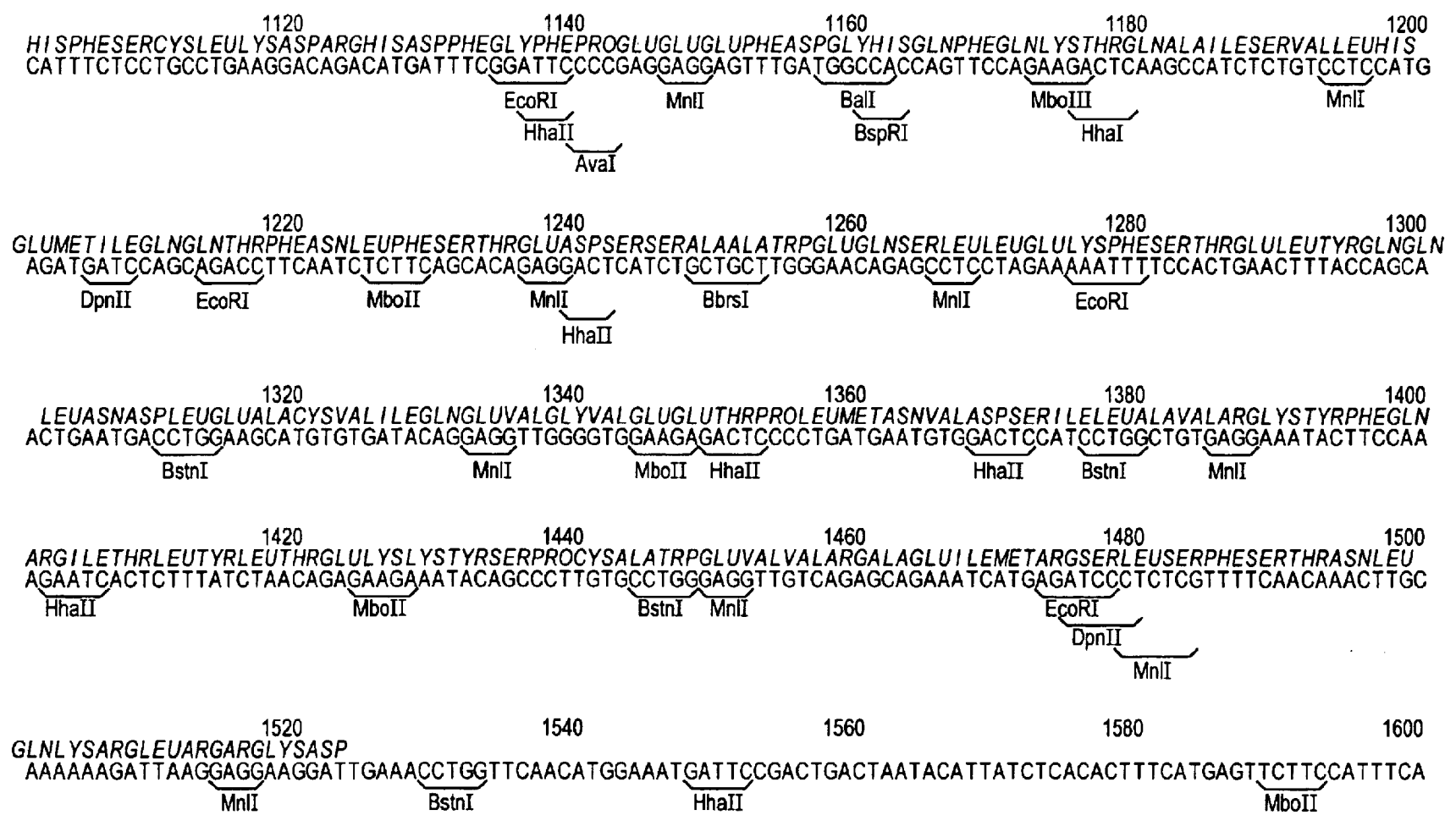

1120 1140 1160 1180 1200
HISPHESERCYSLEULYSASPARGHISASPPHEGLYPHEPROGLUGLUGLUPHEASPGLYHISGLNPHEGLNLYSTHRGLNALAILESERVALLEUHIS
CATTTCTCCTGCCTGAAGGACAGACATGATTTCGGATTCCCCGAGGAGGAGTTTGATGGCCACCAGTTCCAGAAGACTCAAGCCATCTCTGTCCTCCATG
EcoRI MnlI BalI MboIII MnlI
HhaII BspRI HhaI
AvaI 1220 1240 1260 1280 1300
GLUMETILEGLNGLNTHRPHEASNLEUPHESERTHRGLUASPSERSERALAALATRPGLUGLNSERLEULEUGLULYSPHESERTHRGLULEUTYRGLNGLN
AGATGATCCAGCAGACCTTCAATCTCTTCAGCACAGAGGACTCATCTGCTGCTTGGGAACAGAGCCTCCTAGAAAAATTTTCCACTGAACTTTACCAGCA
DpnII EcoRI MboII MnlI BbrsI MnlI EcoRI
HhaII 1320 1340 1360 1380 1400
LEUASNASPLEUGLUALACYSVALILEGLNGLUVALGLYVALGLUGLUTHRPROLEUMETASNVALASPSERILELEUALAVALARGLYSTYRPHEGLN
ACTGAATGACCTGGAAGCATGTGTGATACAGGAGGTTGGGGTGGAAGAGACTCCCCTGATGAATGTGGACTCCATCCTGGCTGTGAGGAAATACTTCCAA
BstnI MnlI MboII HhaII HhaII BstnI MnlI 1420 1440 1460 1480 1500
ARGILETHRLEUTYRLEUTHRGLULYSLYSTYRSERPROCYSALATRPGLUVALVALARGALAGLUILEMETARGSERLEUSERPHESERTHRASNLEU
AGAATCACTCTTTATCTAACAGAGAAGAAATACAGCCCTTGTGCCTGGGAGGTTGTCAGAGCAGAAATCATGAGATCCCTCTCGTTTTCAACAAACTTGC
HhaII MboII BstnI MnlI EcoRI
DpnII
MnlI 1520 1540 1560 1580 1600
GLNLYSARGLEUARGARGLYSASP
AAAAAAGATTAAGGAGGAAGGATTGAAACCTGGTTCAACATGGAAATGATTCCGACTGACTAATACATTATCTCACACTTTCATGAGTTCTTCCATTTCA
MnlI BstnI HhaII MboII

AGACTCACTTCATAACCACCACGAGTTGAATCAAAATTTTCAAATGTTTTCAGCAGTGTGAAGAAGCTTGGTGTATACCGTGCAGGTACTAGTTCTTTA

HhaII HhaII EcoRI MboII BbrI AluI RsaI 1720 1740 1760 1780 1800

CGATGACAATGCTGATGTCTCTGTTCATCTATTTATTTGAATATTTATTTGTTTTTAAAATTTAAATTATTTTTAATGTGATATCATGAGTACCTTTAC

EcoRI RsaI 1820 1840

ATTGTGGTGGATGTAACGATATATGTTCTTCATATTTAGCCAATA

MboIII

*FIG. 32*

DNA SEQUENCES, RECOMBINANT DNA MOLECULES AND PROCESSES FOR PRODUCING HUMAN INTERFERON-LIKE POLYPEPTIDES

This application is a division of U.S. patent application Ser. No. 60/223,108, filed Jan. 7, 1981, now abandoned which application is a continuation-in-part of U.S. patent application 60/118,084, filed Feb. 4, 1980, now U.S. Pat. No. 4,530,901.

TECHNICAL FIELD OF INVENTION

This invention relates to DNA sequences, recombinant DNA molecules and processes for producing interferon and interferon-like polypeptides. More particularly, the invention relates to DNA sequences expressed in appropriate host organisms. The recombinant DNA molecules disclosed herein are characterized by DNA sequences that code for polypeptides having an immunological or biological activity of human leukocyte interferon As will be appreciated from the disclosure to follow, the DNA sequences, recambinant DNA molecules and processes of this invention may be used in the production of polypeptides useful in antiviral and antitumor or anticancer agents and methods.

BACKGROUND ART

In this application the interferon nomenclature announced in *Nature*, 286, p. 2421 (Jul. 10, 1980) will be used. This nomenclature replaces that used in our earlier applications from which this application claims priority. E.g., IF is now designated IFN and leukocyte interferon is now designated IFN-α;

Two classes of interferons ("IFN") are known to exist. Interferons of Class I are small, acid stable (glyco)-proteins that render cells resistant to viral infection (A. Isaacs and J. Lindenmann, "Virus Interference I. The Interferon", *Proc. Royal Soc. Ser. B.*, 147, pp. 258–67 (1957) and W. E. Stewart, II, *The Interferon System*, Springer-Verlag (1979) (hereinafter "*The Interferon System*")). Although to some extent cell specific (*The Interferon System*, pp. 135–45), IFNs are not virus specific. Instead IFNs protect cells against a wide spectrum of viruses.

Human interferons ("HuIFN") have been classified into three groups α, β and γ. HuIFN-α or leukocyte interferon is produced in human leukocyte cells and together with minor amounts of HuIFN-p (fibroblast interferon) in lymphoblastoid cells. HuIFN-β has been purified to homogeneity and characterized (e.g. M. Rubenstein et al., "Human Leukocyte Interferon: Production, Purification To Homogeneity And Initial Characterization" *Proc. Natl. Acad. Sci. USA*, 76, pp. 640–44 (1979)). It is heterogeneous in regard to size presumably because of the carbohydrate moiety. Two components have been described, one of 21000 to 22000 and the other of 15000–18000 molecular weight. The component of lower molecular weight has been reported to represent a non-glycosylated form. The smaller form of HuIFN-α has also been reported to retain most or all of its HuIFN-α activity (W. E. Stewart, II et al., "Effect Of Glycosylation Inhibitors On The Production And Properties of Human Leukocyte Interferon", *Virology*, 97, pp. 473–76 (1979)). A portion of the amino acid sequence of HuIFN-α from lymphoblastoid cells and its amino acid composition have been reported (K. C. Zoon et al., "Amino Terminal sequence Of The Major Component Of Human Lymphoblastoid Interferon", *Science*, 207, pp. 527–28 (1980) and M. Hunkapiller and L. Hood, personal communication (1980))

HuIFN-α has also been reported to exist in several different forms, e.g. British patent application 2,037,296A. These forms appear to differ from each other structurally and physiologically. No accepted nomenclature has been adopted for these forms of HuIFN-α. Therefore, in this application each form will be referred to by a number after the general HuIFN-α designation, i.e., HuIFN-α1 or HuIFN-α3.

HuIFN-α may, like many human proteins, also be polymoiphic. Therefore, cells of particular individuals may produce HuIFN-α species within the more general HuIFN-α group or forms within that group which are physiologically similar but structurally slightly different than the group or form of which it is a part. Therefore, while the protein structure of an HuIFN-α may be generally well-defined, particular individuals may produce a HuIFN-α that is a slight variation thereof, this allelic variation probably being less severe than the difference between the various forms of HuIFN-α.

HuIFN is usually not detectable in normal or healthy cells (*The Interferon System*, pp. 55–57). Instead, the protein is produced as a result of the cell's exposure to an IFN inducer. IFN inducers are usually viruses but may also be non-viral in character, such as natural or synthetic double-stranded RNA, intracellular microbes, microbial products and various chemical agents. Numerous attempts have been made to take advantage of these non-viral inducers to render human cells resistant to viral infection (S. Baron and F. Dianzani (eds.), *Texas Reports On Biology And Medicine*, 35 ("Texas Reports"), pp. 528–40 (1977)). These attempts have not been very successful. Instead, use of exogenous HuIFN itself is now preferred.

Interferon therapy against viruses and tumors or cancers has been conducted at varying dosage regimes and under several modes of administration (The Interferon System, pp. 305–321). For example, interferon has been effectively administered orally, by innoculation—intravenous, intramuscular, intranasal, intradermal and subcutaneous—, and in the form of eye drops, ointments and sprays. It is usually administered one to three times daily in dosages of $10^4$ to $10^7$ units. The extent of the therapy depends on the patient and the condition being treated. For example, virus infections are usually treated by daily or twice daily doses over several days to two weeks and tumors and cancers are usually treated by daily or multiple daily doses over several months or years. The most effective therapy for a given patient must of course be determined by the attending physician who will consider such well known factors as the course of the disease, previous therapy, and the patient's response to interferon in selecting a mode of administration and dosage regime.

As an antiviral agent, HuIFN has been used to. treat the following: respiratory infections (*Texas Reports*, pp. 486–96); herpes simplex keratitis (*Texas Reports*, pp. 497–500); acute hemorrhagic conjunctivitis (*Texas Reports*, pp. 501–10); varicella zoster (*Texas Reports*, pp. 511–15); cytomegalovirus infection (*Texas Reports*, pp. 523–27); and hepatitis B (*Texas Reports*, pp. 516–22). See also *The Interferon System*, pp. 307–19. However, large scale use of IFN as an antiviral agent requires larger amounts of IFN than heretofore have been available.

HuIFN has other effects in addition to its antiviral action. For example, it antagonizes the effect of colony stimulating factor, inhibits the growth of hemopoietic colony-forming cells and interferes with the normal differentiation of granulocyte and macrophage precursors (*Texas Reoorts*, pp.

343–49). It also inhibits erythroid differentiation in DMSO-treated Friend leukemia cells (*Texas Reports*, pp. 420–28). HuIFN may also play a role in regulation of the immune response. Depending upon the dose and time of application in relation to antigen, HuIFN-α can be both immunopotentiating and immunosuppressive in vivo and in vitro (*Texas Reports*, pp. 357–69). In addition, specifically sensitized lymphocytes have been observed to produce HuIFN-α after contact with antigen. Such antigen-induced HuIFN-α could therefore be a regulator of the immune response, affecting both circulating antigen levels and the expression of cellular immunity (*Texas Reports*, pp. 370–74). HuIFN is also known to enhance the activity of killer lymphocytes and antibody-dependent cell-mediated cytotoxicity (R. R. Herberman et al., "Augmentation By Interferon Of Human Natural And Antibody Dependent Cell-Mediated Cytotoxicity", *Nature*, 277, pp. 221–23 (1979); P. Beverley and D. Knight, "Killing Comes Naturally", *Nature*, 278, pp. 119–20 (1979); *Texas Reports*, pp. 375–80). Both of these species are probably involved in the immunological attack on tumor cells.

Therefore, in addition to its use as a human antiviral agent, HuIFN has potential application in antitumor and anticancer therapy (*The Interferon System*, pp. 319–21). It is now known that IFNs affect the growth of many classes of tumors in many animals (*The Interferon System*, pp. 292–304). They, like other antitumor agents, seem most effective when directed against small tumors. The antitumor effects of animal IFN are dependent on dosage and time but have been demonstrated at concentrations below toxic levels. Accordingly, numerous investigations and clinical trials have been and continue to be conducted into the antitumor and anticancer properties of IFNs. These include treatment of several malignant diseases such as osteosarcoma, acute myeloid leukemia, multiple myeloma and Hodgkin's disease (*Texas Reports*, pp. 429–35). In addition, HuIFN has recently been shown to cause local tumor regression when injected into subcutaneous tumoral nodules in melanoma- and breast carcinoma-affected patients (T. Nemoto et al., "Human Interferons And Intralesional Therapy of Melanoma And Breast Carcinoma", *Amer. Assoc. For Cancer Research*, Abs. nr. 994, p. 246 (1979)). Although the results of these clinical tests are encouraging, the antitumor and anticancer applications of IFN have been severely hampered by lack of an adequate supply of purified IFN.

Today, HuIFN-α is produced either through human cells grown in tissue culture or through human leukocytes collected from blood donors. $2.6\times10^9$ IU of crude HuIFN-α have been reported from 800 1 of cultured Namalva cells (P. J. Bridgen et al., supra). At very large blood centers, eg., the Finnish Red Cross Center in Helsinki, Finland, the production capacity is about $10^{11}$ IU of crude HuIFN-α annually. Since dosage is typically $3\times10^6$ IU per patient per day, these sources are not adequate to provide the needed commercial quantities of HuIFN-α. Therefore, production of HuIFN-α by other procedures is desirable. Because the specific activity of IFN-α is high, in the order of $4.0\times10^8$ to $10^9$ IU/mg, the amount of HuIFN-α required for commercial applications is low. For example, 100 grams of pure HuIFN-α would provide between 3 and 30 million doses.

Recent advances in molecular biology have made it possible to introduce the-DNA coding for specific nonbacterial eukaryotic proteins into bacterial cells. In general, with DNA other than that prepared via chemical synthesis, the construction of such recombinant DNA molecules comprises the steps of producing a single-stranded DNA copy (cDNA) of a purified messenger RNA (IRNA) template for the desired protein; converting the cDNA to double-stranded DNA; linking the DNA to an appropriate site in an appropriate cloning vehicle to form a recombinant DNA molecule and transforming an appropriate host with that recombinant DNA molecule. Such transformation may permit the host to produce the desired protein.

Several non-bacterial proteins and genes have been obtained in *E. coli* using recombinant DNA technology. These include a protein displaying rat proinsulin antigenic determinants (L. Villa-Komaroff et al., "A Bacterial Clone Synthesizing Proinsulin", *Proc. Natl. Acad. Sci. USA*, 75, pp. 3727–31 (1978)), rat growth hormone (P. H. Seeburg et al., "Synthesis Of Growth Hormone By Bacterial", *Nature*, 276, pp. 795–98 (1978)), mouse dihydrofolate reductase (A. C. Y. Chang et al., "Phenotypic Expression In *E. coli* Of A DNA Sequence Coding For Mouse Dihydrofolate Reductase", *Nature*, 275, pp. 617–24 (1978)), human somatostatin (K. Itakura et al., "Expression In *Escherichia coli* Of A Chemically Synthesized Gene For The Hormone Somatostatin", *Science*, 198, pp. 1056–63 (1977)); European patent applications 0,001,929, 0,001,930, and 0,001, 931 and cognate applications in other countries), the A and B polypeptide chains of-human insulin (D. V. Goeddel et al., "Expression In *Escherichia coli* Of Chemically Synthesized Genes For Human Insulin", *Proc. Natl. Acad. Sci. USA*, 76, pp., 106–10 (1979) and the European and related patent specifications, supra), antigens of human hepatitis B virus (C. J. Burrell et al., "Expression In *Escherichia coli*: Of Hepatitis B Virus DNA Sequences Cloned In Plasmid pBR322", *Nature*, 279, pp. 43–7 (1979) and M. iasek et al., "Hepatitis B Virus Genes And Their Expression In *E. coli*", *Nature*, 282, pp. 575–79 (1979).), human growth hormone (D. V. Goeddel et al., "Direct Expression In *Escherichia coli* Of A DNA Sequence Coding For Human Growth Hormone", *Nature*, 281, pp. 544–51 (1979)), SV40 t antigen (T. M. Roberts et al., "Synthesis of Simian virus 40 t Antigen In *Escherichia coli*", *Proc. Natl. Acad. Sci. USA*, 76, pp. 5596–600 (1979)), and human fibroblast interferon (HuIFN-β) (T. Taniguchi et al., "Construction And Identification Of A Bacterial Plasmid Containing The Human Fibroblast Interferon Gene Sequence", *Proc. Japan Acad.*, 55, Ser. B, pp. 464–69 (1979) together with personal communication 1980).

None of these recombinant DNA processes, however is directed, as is this invention, toward the synthesis of HuIFN-α. This is the problem to which the present invention is addressed. Its solution is not facilitated as were the above described recombinant DNA schemes by the availability of the sequence information required to prepare a synthetic gene (e.g., somatostatin) or of a cell type or virus rich in aparticular DNA sequence (e.g., hepititis viral antigen) or URNA species (e.g., rat insulin) which allows preparation and identification of bacterial clones containing the desired hybrid DNA, or of a system allowing the selection of *E. coli* hosts that express the desired protein (e.g., mouse dihydrofolate reductase). Neither is it aided by the report of a plasmid which is said to contain a DNA sequence that hybridizes to a mRNA from a poly(A) RNA, that mRNA producing HuIFN-β activity in oocytes (e.g., fibroblast interferon). Nor is the solution of the present invention addressed as is the apparent suggestion of Research Disclosure No. 18309, pp. 361–62 (1979) to preparing pure or substantially pure HuIFN-αmRNA before cloning of the HuIFN-α gene.

Finally, it should be recognized that the selection of a DNA sequence or the construction of a recombinant DNA molecule which hybridizes to d mRNA from. polyA RNA, that mRNA producing HuIFN activity in oocytes, is not sufficient to demonstrate that the DNA sequence or the hybrid insert of the recombinant DNA molecule corresponds to HuIFN. Instead, only the production of a polypeptide that displays an immunological or biological. activity of HuIFN can actually demonstrate that the selected DNA sequence or constructed recombinant DNA molecule corresponds to HuIFN. More importantly, it is only after HuIFN activity is shown that the DNA sequence, recombinant DNA molecule or sequences related to them may be employed to select other sequences corresponding to HuIFN in accordance with this invention.

It will therefore be appreciated from the foregoing that the problem of producing HuIFN-α with the use of recombinant DNA technology is much different than any of the above described processes. Here, a particular DNA sequence of unknown structure—that coding for the expression of HuIFN-α in an appropriate host—must be found in and separated from a highly complex mixture of DNA sequences in order for it to be used in the production of HuIFN-α. Moreover, this location and separation problem is exacerbated by the predicted exceedingly low concentration of the desired DNA sequence in the complex mixture and the lack of an effective means for rapidly analyzing the many DNA sequences of the mixture to select and separate the desired sequence.

DISCLOSURE OF THE INVENTION

The present invention solves the problems referred to by locating and separating DNA sequences that code for the expression of HuIFN-α in an appropriate host and thereby providing DNA sequences, recombinant DNA molecules and methods by means of which a host is transformed to produce a polypeptide displaying an immunological or biological activity of human leukocyte interferon.

By virtue of this invention, it is possible to obtain polypeptide(s) displaying an immunological or biological activity of HuIFN-α for use in antiviral, antitumor or anticancer agents and methods. This invention allows the production of these polypeptides in amounts and by methods hitherto not available.

As will be appreciated from the disclosure to follow, the DNA sequences and recombinant DNA molecules of the invention are capable of directing the production, in an appropriate host, of a polypeptide displaying an immunological or biological activity of HIFN-α. Replication of these DNA sequences and recombinant DNA molecules in an appropriate host also permits the production in large quantities of genes coding for these polypeptides. The molecular structure and properties of these polypeptides and genes may be readily determined. The polypeptides and genes are useful, either as produced in the host or after appropriate derivatization or modification, in compositions and methods for detecting and improving the production of these products themselves and for use in antiviral and antitumor or anticancer agents and methods.

This process is therefore distinguishable from the prior processes, above mentioned, in that this process, contrary to the noted prior processes, involves the preparation and selection of DNA sequences and recombinant DNA molecules which contain appropriate DNA sequences which code for at least one polypeptide displaying an immunological or biological activity of HuIFN-α.

It will be appreciated from the foregoing that a basic aspect of this invention is the provision of a DNA sequence which is characterized in that it codes for a polypeptide displaying an imunological or biological activity of HuIFN and is selected from the group consisting of the DNA inserts of Z-pBR322 (Pst)/HcIF-4c, Z-pBR322(Pst)/HcIF-2h, Z-pBR322(Pst)/HcIF-SN35, Z-pBR322(Pst)/HcIF-SN42, Z-pKT287(Pst)/HcIF-2h-AH6, DNA sequences which hybridize to any of the foregoing DNA inserts, DNA sequences, from whatever source obtained, including natural, synthetic or semi-synthetic sources, related by mutation, including single or multiple, base substitutions, deletions, insertions and inversions to any of the foregoing DNA sequences or inserts, and DNA sequences comprising sequences of codons which on expression code for a polypeptide displaying similar immunological or biological activity to a polypeptide coded for on expression of the codons of any of the foregoing DNA sequences and inserts and that these sequences permit the production of interferon and interferon-like polypeptides in hosts.

BRIEF DESCRIPTION OF THE DRAWINGS

FIGS. 8–10 display the positions of these restriction sites as determined by nucleotide sequence data.

FIG. 6 displays the partial nucleotide sequence of some cloning vehicles useful in accordance with this invention.

FIGS. 8–10 display the nucleotide sequence of a DNA insert to a recombinant DNA molecule of this invention. The sequence is numbered from the nucleotide following the polyG 5' tail to the nucleotide before the polyA residues and polyC 3' tails. Nucleotides 57–125 represent a signal sequence and nucleotides 126–626 represent the “mature” interferon and the stop codon. The amino acid sequence of the signal sequence is depicted above its nucleotide sequence in lower case letters and the amino acid sequence of the “mature” inteferon is depicted above its nucleotide sequence in upper case letters. Various restriction endonuclease recognition sites in this gene and also depicted in FIG. 8–10, these sites being determined by analysis of nucleotide sequence data.

FIGS. 12–16 display the nucleotide sequences of two DNA inserts of recombinant DNA molecules of this invention. The sequences are numbered from the nucleotide following the polyG 5' tail to the nucleotide before the polyA residues and polyC 3' tails. The amino acid sequence of the signal sequence for each of these inserts is depicted above its respective nucleotide sequence in lower case letters and the amino acid sequence of the "mature" interferon is depicted above its nucleotide sequence in upper case letters.

FIGS. 20–23 display the nucleotide sequence of the HchrIF-35HBα frament and the amino acid sequence derived from it.

FIGS. 29–32 display the nucleotide sequence and amino acid sequence encoded thereby for IFN-α4b and its signal sequence.

BEST MODE OF CARRYING OUT THE INVENTION

Figure 1:
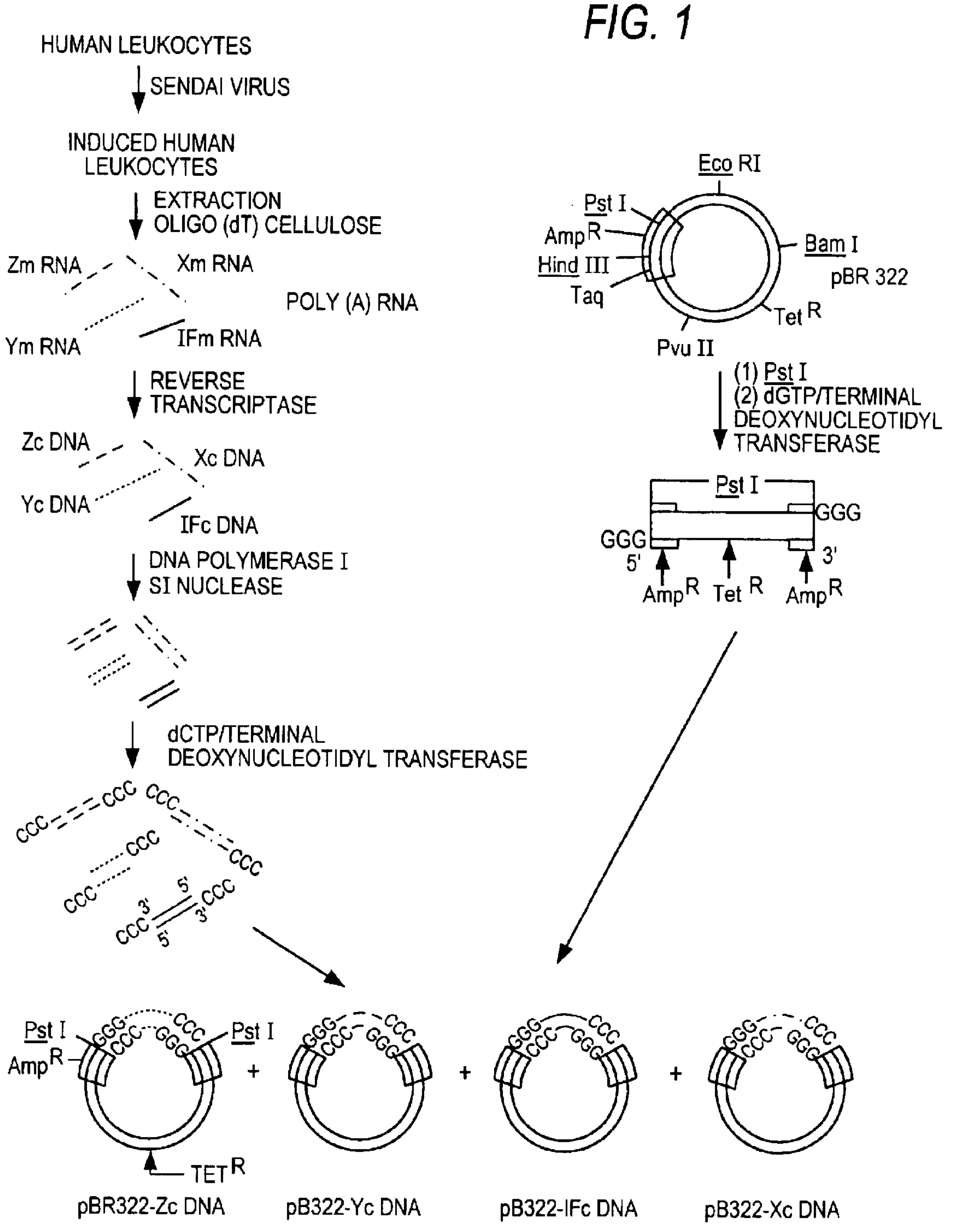
FIG. 1 is a schematic outline of one embodiment of a process of this invention for preparing a mixture of recombinant DNA molecules, some of which are characterized by inserted DNA sequences that code for polypeptides of this invention.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose). That combination of a base and a sugar is called a nucleoside. Each nucleotide is characterized by its base. The four DNA bases are adenine ("A"), guanine ("G"), cytosine ("C") and thymine (UT"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the sequence GCTGGTTGTAAG may be translated in three reading frames or phases, each of which affords a different amino acid sequence:

GCT GGT TGT AAG—Ala-Gly-Cys-Lys

G CTG GTT GTA AG—Leu-Val-Val

GC TGG TTG TAA G—Trp-Leu-(STOP)

Polypeptide—A linear array of amino acids connected one to the other by peptide bonds between the α-amino and carboxy groups of adjacent amino acids.

Genome—The entire DNA of a cell or a virus. It includes inter alia the structural genes coding for the polypeptides of the substance, as well as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the platmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cloning Vehicle—A plasmid, phage DNA or other DNA sequences which are able to replicate in a host cell, which are characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloninq—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

Expression Control Sequence—A sequence of nucleotides that controls and regulates expression of structural genes when operatively linked to those genes. They include the 1 system, the trp system, major operator and promoter regions of phage λ, the control region of fd coat protein and other sequences known to control the expression of genes of prokaryotic or eukaryotic cells and their viruses.

Referring now to FIG. 1, we have shown therein a schematic outline of one embodiment of a process for preparing a mixture of recombinant DNA molecules, some of which are characterized by inserted DNA sequences that codefor polypeptides having an immunological or biological activity of human leukocyte interferon.

Preparation of Poly(A) RNA Containing Human Interferon mRNA (IFN-αmRNA)

Human leukocytes were induced for 5 hours at 37° C. with Sendai virus and extracted to yield a poly(A) RNA mixture containing human leukocyte interferon mRNA ("HuIFN-αmRNA"). Induction was by the Cantell procedure (*The Interferon System*, pp. 130–31 and the references cited therein). The poly(A) RNA mixture is illustrated without regard to its actual proportions in FIG. 1. Induced leukocytes were harvested and $10^{11}$ cells were resuspended in 1 l of a solution containing 8 g NaCl, 0.2 g KCl, 1.15 g $Na_2HPO_4H_2O$ and 0.2 g $KH_2PO_4$ dissolved in 1 l of water ("PBS") and added slowly with vigorous stirring to 17 l 20 mM Tris-BCl (pH 7.5), 1 mM EDTA ("TE buffer"), 2% sodium dodecyl sulfate ("SDS") in a 50 l separatory funnel. Self-digested Pronase (Calbiochem) was added to 200 ua/ml and the solution sqtirre-d for 1 h at room temperature. $10^6$ counts/minute ("cpm") of $^{125}$I-globin mRNA were added as a marker for recovery of the poly(A) RNA and to control for mRNA degradation during subsequent steps. 2M Tris-HCl (pH 9) in an amount equal to 1/20 of the total volume ("1/20 vol") was added and the mixture extracted with vigorous stirring with 15 l of redistilled phenol for 10 min. Three 1 chloroform were added and the mixture stirred for 5 min. After allowing 30 min for phase separation, the aqueous phase was removed and extracted again with phenol and chloroform. The resultant aqueous phase, totalling 19.1 l, was combined with 60 g SDS. Nucleic acids were precipitated from the aqueous phase with 1/10 vol 3M sodium acetate (pH 5.5). and 2 vol ethanol.

After storage overnight at −20° C., the fibrous nucleic acid precipitate was removed by filtration through a plastic tea sieve. This material was then stirred with 200 ml TNE (50 mM Tris-SCl (pH 7.5), 100 mM NaCl, 5 mM EDTA) containing 0.5% SDS. It subsequently dissolved on addition of a further 350 ml of that solution. The non-fibrous precipitate was collected by centrifugation in 1 l Sorvall bottles in a Sorvall RC-3 centrifuge for 15 min at 5,000 rpm and dissolved in 350 ml TNE containing 0.5% SDS. The two TNE solutions were combined, extracted 3 times with 1 vol phenol, 3 times with ½ vol ether and 3 times with 1 vol ether. RNA recovery from the aqueous phase totalled 775 mg, as measured by absor- bance at 260 nm.

Isolation of the poly(A) RNA mixture was achieved by repeated batch adsorption to oligo(dT) cellulose (type 7, P-L Biochemicals, Inc.). 2.7 grams oligo(dT) cellulose were added to 500 ml, i.e., about half of the RNA-containing solution described above. After stirring for 1 h at room temperature to effect adsorption of the poly(A) RNA to the oligo(dT.) cellulose, the cellulose and the mixture of mRNAs bound to it were collected by centrifugation and washed once with 50 ml TNE and a second time with 15 ml TNE. The bound poly(A) RNA was then eluted by five successive washes with 2 ml B20. The yield was 860 μg poly(A) RNA as measured by optical density (Preparation A). The supernatant RNA solution from the first adsorption was subjected to two further adsorption cycles, exactly as described above. The second and third adsorptions yielded 600 μg and 170 μg RNA respectively and were combined (Preparation B).

RNA was assayed for HuIFN-αmRNA by injection into *Xenopus laevis* oocytes (*The Interferon System*, pp. 93–95): RNA was dissolved in 15 mM Tris-Hcl (pH 7.5), 88 mM NaCl ("TNK buffer") to give a concentration of about 1 mg/ml. Fifty nl of this solution were injected into each of 50 oocytes. The oocytes were incubated overnight at room temperature in Barth medium (Gurdon, *J. Embryol and Exper. Morph.*, 20, pp. 401–414(1968) and Barth, *J. Embryol and Exper. Morph.*, 7, pp. 210–222 (1959)). The incubated oocytes were then rinsed and homogenized with a Pasteur pipette in a 1.5 ml Eppendorf centrifuge tube in 0.5 ml 52 mM Tris glycine buffer (pH 8.9). The mixture was centrifuged for 2 min in an Eppendorf centrifuge and the supernatant was drawn off and frozen at −20° C. for assay. IFN-α activity was determined by the plaque reduction assay described by H. Strander and K. Cantell, "Production Of Interferon By Human Leukocytes In Vitro", *Ann. Med. exp. Fenn.*, 44, pp. 265–73 (1966). One unit IFN-α reduces virus plaques by 50%. The potency of an IFN-α preparation is expressed relative to the human reference HuIFN-α 69/19 (International Symposium on Standardization of Interferon and Interferon Inducers, 1969). Alternatively, the assay was based on the reduction of cytopathic effect, essentially as described by W. E. Stewart, II and S. E. Sulkin, "Interferon Production In Hamsters Experimentally Infected With Rabies Virus", *Proc. Soc. Exp. Biol. Med.*, 123, pp. 650–3 (1966), except that human CCL-23 cells were used and that challenge was with Mengo virus. The oocyte extracts had 300 IU of IFN-α activity per μg of RNA injected. In later assays incubation of injected oocytes was for 48 hrs and only the incubation medium was assayed because most of the interferon is excreted by the oocytes (A. Colman and J. Morser, "Export Of Proteins From Oocytes of *Xenopus laevis", Cell*, 17, pp. 517–26 (1979)). For further purification of the poly(A) RNA sufficient 0.5 M. ethylene diamine tetraacetic acid ("EPTA") was added to the poly(A) RNA Preparation A to bring the concentration to 5 mM EDTA. The resultant solution was extracted twice with an equal vol of TNE-saturated phenol and 5 times with an equal vol of ether. It was then passed through a 0.1-ml Chelex-100 Bio-Rad column, heated for 90 sec at 100° C. and layered onto a 13-ml 5–23% sucrose gradient containing 50 mM Tris-HC1 (pH 7.5), 1 mM EDTA, 0.2 M NaCl. 10,000 cpm of 5'-terminally $^{32}$P-labeled DNA fragments produced by simultaneous digestion of pBR322 with restriction enzymes HindIII and PstI (New England Biolabs), were added as size markers. Centrifugation was in an SW40 rotor at 10° and 35,000 rpm for 16 h. Fractions (0.6 ml) were collected with an ISCO gradient collector at 1 ml/min. The fractions were assayed for HuIFN-αmRNA as described above and their position relative to the $^{32}$P-DNA markers was noted for future reference. In subsequent centrifugations, HuIFN-αmRNA-containing fractions were identified relative to the markers. The fractions with HuIFN-αmRNA activity contained 80 μg of poly(A) RNA. They were mixed with 2 vol TNE containing 0.5% SDS and 0.02% polyvinyl sulfate (in later preparations polyvinyl sulfate was omitted) and applied to a 50-μl oligo(dT) cellulose column. After washing the column as described above, 40 μg of the RNA mixture were eluted with 4 washes of 0.6 ml sterile distilled water. After ethanol precipitation, the RNA was dissolved to 1 mg/ml in 0.5 mM EDTA.

An assay for HuIFN-αmRNA activity was carried out as described above on a portion of the poly(A) RNA precipitate. It had a specific activity of 3600 IU interferon/μg of RNA injected. Therefore, the sucrose gradient had enriched the poly(A) RNA about 10-fold in regard to HuIFN-αmRNA. In a subsequent, similar preparation about a 40-fold enrichment was obtained. Preparation B was purified similarly and, since it had a similar specific activity as Preparation A, the two were pooled.

At this point it should be recognized that even the poly(A) RNA product obtained from the sucrose gradient contains a very large number of different mRNA's. Except for the ZRNA specific for IFN-α, the other mRNAs are undesirable contaminants (FIG. 1). Unfortunately, these contaminant RNAs behave similarly to HuIFN-αmRNA throughout the remainder of the cloning process of this invention. Therefore, their presence in the poly(A) RNA will result in the ultimate preparation of a large number of unwanted bacterial clones which contain genes that code for polypeptides other than IFN-α. This contamination presents complex screening problems in the isolation of the desired IFN-α hybrid clones. In the case of IFN-α, the screening problem is further exacerbated by the lack of a sufficiently purified sample of HuIFN-αmRNA or DNA or portion thereof to act as a screening probe for the identification of the desired clones. Therefore, the screening process for the IFN-α clones is very time-consuming and difficulty. Further, because only a very small percentage of IFN-α clones themselves are expected to express IFN-α in a biologically active or immunologically active form, the isolation of an active clone is a "needle in a haystack" screening process.

Advantageously, we may use recombinant DNA technology to provide a purified sample of HuIFN-αmRNA or cDNA or a portion thereof. This purified mRNA or cDNA can be used to screen rapidly very large numbers of bacterial clones and thereby markedly increase the probability of isolating a clone which expresses IFN-α in an active form.

Synipesis of cDNA Moxture Containing HuIFN-αcDNA

The poly(A) RNA enriched for IFN-αmRNA (Preparation A+B) was used as a template to prepare single-stranded complementary DNA (cDNA) (FIG. 1) (Cf, A. Efstratiadis et al., "Full Length And Discrete Partial Reverse Transcripts Of Clobin And Chorion mRNAs", *Cell*, 4, pp. 367–78 (1975) and references cited therein). The 800-μl reaction mixture contained 40 mM Tris-HCl (pB 7.5), 30 mM NaCl, 5 mM $MgCl_2$, 0.5 MM DTT (Cal-Biochem), 20 μg/ml oligo(dT) 12–18 (P&L Biochemicals), 5 mM dGTP (Schwarz), dCTP (Laevosan) and dTTP (Sigma), 5 mM $^{32}$p-dATP (NEN, specific activity 100,000 cpm/nmole), 60 μg/ml poly(A) RNA and 280 units avian myeloblastosis virus (AMV) reverse transcriptase (a gift from Life Sciences, Inc., St. Petersburg, Fla.). After incubation for 1 h at 37° C., 0.5 M EDTA and 20% SDS (recrystallized) were added to 10 mM EDTA and 0.1% SDS. The mixture was extracted with 1 vol phenol (distilled). The phenol phase was washed with 200 μl 200 mM Tris-HCl (pH 7.5), 1 mM EDTA and 0.1% SDS, and the aqueous phases combined. These were extracted with an equal vol ether (Fluka, pro anal.) and chromatographed on a 5-ml Sephadex G-100 column in TNE. Fractions of 0.1 ml were collected at 0.3 ml/min. Fractions displaying radioactivity (as measured by cerenkov radiation) were combined and 3 M sodium acetate added to 0.3M. The nucleic acids were precipitated with 2.5 vol of ethanol. After storage overnight at −20° C., the samples were centrifuged and the supernatant discarded. The precipitate was dissolved in 180 μl distilled water and transferred to a siliconized Eppendorf tube. 20 μl 5M NaOH were added and the mixture kept at room temperature for 40 min. 20 μl of 5M sodium acetate, 100 μl distilled water and 500 μl ethanol were added. After cooling overnight at −20° C., the resulting precipitate was collected by centrifugation at a force equivalent to 10,000 times the force of gravity (10000×g) for 20 min at 0° C. The yield of single-stranded cDNA was 10 μg.

Again, it is to be understood that the single-stranded cDNA product prepared above is in reality a complex mixture of a large number of different cDNAs transcribed from the corresponding mRNAs present in the poly(A) RNA mixture (FIG. 1). Only a very few of these cDNAs are IFN-α related, i.e., HiIFN-αcDNAs. Another factor also acts to complicate the cDNA mixture—each mRNA species of the poly(A) RNA mixture is usually not transcribed completely. Instead, for each mRNA species the transcription process may stop before the end of the mRNA is reached. Therefore, a large variety of cDNA species may be produced from each mRNA species (not shown in FIG. 1). Each species will behave more or less similarly in the subsequent cloning process so that bacterial clones will be produced which contain recombinant DNA molecules having only a fragment of the gene for a particular protein. The presence of these fragment-containing clones even further complicates the final clone screening process.

The sizes of the various single-stranded cDNAs were determined by electrophoresis of a small aliquot on a alkaline 2% agarose gel using 30 mM NaOR, 2 mM EDTA as electrolyte (M. W. McDonell et al., "Analysis Of Restriction. Fragments Of T7 DNA And Determination Of Molecular Weights,By Electrophoresis In Neutral And Alkaline Gels", *J. Mol. Biol.*, 110, pp. 119–46 (1977)). The $^{32}$P-cDNA had a length of 600–1000 nucleotides, relative to single-stranded globin cDNA and $^{32}$P-labeled DNA fragments used as size markers.

Preparation of Double-stranded cDNA

The single-stranded cDNA may be rendered double-stranded by treatment with DNA polymerase I (T. Maniatis et al., "Amplification And Characterization Of A P-Globin Gene Synthesized In Vitro", Cell, 8, pp. 163–82 (1976)). The precipitated single-stranded cDNA from above was dissolved in 200 μl $H_2O$, heated at 100IC for 2 min and incubated in 500 μl 0.1 M heat denatured potassium phosphate buffer (pH 6.9), 10 mM $MgCl_2$, 10 mM DTT (Calbiochem), 1 mm each of dATP (Merck), dGTP (Schwarz) and dCTP (Laevosan), 1 mM $^3$H-dTTP (NEN, specific activity 100,000 cpm/nmole) and 150 units/ml of *E. coli* DNA polymerase I (Boehringer-Mannheim). After 6.5 h at 15° C., 0.5 MEDTA and 20% SDS were added to 10 mM EDTA and 0.1% SDS. The mixtre was then extracted with 500 μl phenol and the phenol phase was reextracted with 250 μl 20 mM Tris-EC1 (pH .7.5), 5 mM EDTA ("TE buffer"). The two aqueous phases were combined and chromatographed on a 5-ml Sephadex G-100 collon under the same conditions described previously. Sodium acetate (3M) was added to 0.3 M and 2.5 vol ethanol were mixed into precipitate the DNA. A total of 13 μg DNA was recovered.

The DNA was treated with nuclease $S_1$, prepared by the method of R. C. Wiegand et al. "Specificity of The $S_1$ Nuclease From *Asperlillus Oryzae, J. Biol. Chem.*, 250, pp. 8848–55 (1975). She pxkipitated DNA was dissolved in 250 μl $S_1$ buffer (0.2 N NaCl, 50 mM sodium acetate (pH 4.5), 10 mM zinc sulfate) and warmed at 37° C. for 30 min. 1.5 μl $S_1$ enzyme (11 units/μl) were added and the mixture incubated at 370° C. for 30 min. SDS and EDTA were added to 0.1% SDS and 5 mM EDTA, and the mixture was extracted with 250 μl phenol. The phenol phase was washed with 100 ul TE buffer. The aqueous phases were combined and chromatographed on a Sephadex G-100 (Pharmacia) column in TNE; 0.1-ml fractions were collected at 0.3 ml/min and the Cerenkov radiation of each fraction was determined. 8 $\mu$g of double-stranded cDNA were recovered after precipitation with ethanol and sodium acetate as above.

Again, it must be recognized that the double-stranded cDNA produced above is a miwture of a large number of cDNAs and fragments thereof, only a very few of which are HuIFN-αcDNA or its fragments (FIG. 1).

Cloning of Double-stranded DNA

A wide variety of host/cloning vehicle combinations may be employed in cloning the double-stranded cDNA prepared as above described. For example, useful cloning vehicles may consist of segments of chromosomal, non-chromosomal and synthetic DNA sequences, such as various known bacterial plasmids, e.g., plasmids from *E. coli* including col El, pCR1, pBR322 and their derivatives, wider host range plasmids, e, RP4, phage DNA, e.g., the numerous derivatives of phage λ, e.g., NM 989, and vectors derived from combinations of plasmids and phage DNAs such as plasmids which have been modified to employ phage DNA or other expression control sequences or yeast plasmids such as the 2$\mu$ plasmid or derivatives thereof. Useful hosts may include bacterial hosts such as strains of *E. coli*, e.g., *E. coli* EB 101*, E. coli* X1776*, E. coli* X2282*, E. coli* MRCI and strains of *Pseudomonas, Bacillus subtilis, Bacillus stearothermorhilus* and other bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the double-stranded.DNA. These sites are usually designated by the restriction endonuclease which cuts them. For example, in pBR322 the PstI site is located in the gene for β-lactamase, between the nucleotide triplets that code for amino acids 181 and 182 of that protein. This site was employed by Villa-Komaroff et al., supra, in their synthesis of protein displaying rat proinsulin antigenic determinants. One of the two HindII endonuclease recognition sites is between the triplets coding for amino acids 101 and 102 and one of the several Tag sites at the triplet coding for amino acid 45 of β-lactamase in pBR322. In similar fashion, the EcoRI site and the PvuII site in this plasmid lie outside of any coding region, the EcoRI site being located between the genes coding for resistance to tetracycline and ampicillin, respectively. This site was employed by Itakura et al. and Goeddel et al. in their recombinant synthetic schemes, supra. These sites are well recognized by those of skill in the art. It is, of course, to be understood that a cloning vehicle useful in this invention need not have a restriction endonuclease site for insertion of the chosen DNA fragment. Instead, the vehicle could be joined to the fragment by alternative means.

The vector or cloning vehicle and in particular the site chosen therein for attachment of a selected DNA fragment to form a recombinant DNA molecule is determined by a variety of factors, e.g., number of sites susceptible to a particular restriction enzyme, size of the protein to be expressed, susceptibility of the desired protein to proteolytic degradation by host cell enzymes, contamination of the protein to be expressed by host cell proteins difficult to remove during purification, expression characteristics, such as the location of start and stop codons relative to the vector sequences, and other factors recognized by those of skill in the art. The choice of a vector and an insertion site for a particular gene is determined by a balance of these factors, not all selections being equally effective for a given case.

Although several methods are known in the art for inserting foreign DNA into a cloning vehicle or vector to form a recombinant DNA molecule, the method preferred for a first construction in accordance with this invention is described in Villa-Komaroff et al., supra, and displayed in FIG. 1. This method is characterized by digesting the plasmid (in particular pBR322) with that restriction enzyme specific to the site chosen for the insertion (in particular PstI) and adding dGMP tails to the termini by terminal transferase. dGMP tails are added to the 5' termini of the cut plasmid to regenerate the PstI site and permit linkage to a cDNA fragment carrying the complementary tails. In similar fashion, the double-stranded cDNA is elongated by the addition of dCMP tails to the 3' termini to allow joining to the tailed plasmid. The tailed plasmid and cDNA are then annealed to insert the cDNA in the appropriate site of the plasmid and to circularize the hybrid DNA, the complementary character of the tails permitting their cohesion (FIG. 1). The resulting recombinant DNA molecule now carries a gene at the chosen restriction site (FIG. 1).

Of course, other known methods of inserting DNA sequences into cloning vehicles to form recombinant DNA is molecules are equally useful in this invention. These include, for example, direct ligation, synthetic linkers, exonuclease and polymerase-linked repair reactions followed by ligation, or extension of the DNA strand with DNA polymerase and an appropriate single stranded template followed by ligation.

It should, of course, be understood that the nucleotide sequences or cDNA fragment inserted at the selected site of the cloning vehicle may include nucleotides which are not part of the actual structural gene for the desired polypeptide or may include only a fragment of the complete structural gene for the desired protein. It is only required that whatever DNA sequence is inserted, a transformed host will produce a polypeptide having a biological or immunological activity of HuIFN-α or that the DNA sequence itself is of use as a hybridization probe to select clones which contain DNA sequences useful in the production of polypeptides having an immunological or biological activity of HuIFN-α.

The cloning vehicle or vector containing the foreign gene is employed to transform a host so as to permit that host to express, the protein or portion thereof for which the hybrid DNA codes. The selection of an appropriate host is also controlled by a number of factors recognized by the art. These include, for example, compatibility with the chosen vector, toxicity of proteins encoded by the hybrid plasmid, ease of recovery of the desired protein, expression characteristics, biosafety and costs. A balance of these factors must be struck with the understanding that not all hosts may be equally effective for expression of a particular recombinant DNA. molecule.

In the present synthesis, the preferred initial cloning vehicle is the bacterial plasmid pBR322 and the preferred initial restriction endonuclease site therein is the PstI site (FIG. 1). The plasmid is a small (molecular weight approx. 2.6 megadaltons) plasmid carrying resistance genes to the antibiotics ampicillin (Amp) and tetracycline (Tet). The plasmid has been fully characterized (F. Bolivar et al., "Construction And Characterization Of New Cloning Vehicles II. A Multi-Purpose Cloning System", *Gene*, pp. 95–113 (1977); J. G. Sutcliffe, "pBR322 Restriction Map Derived From The DNA Sequence: Accurate DNA Size Markers Up To 4361 Nucleotide Pairs Long", *Nucleic Acids Research*, 5, pp. 2721–28 (1978)). Insertion of the DNA product in this site provides a large number of bacterial clones each of which contains one of the DNA genes or fragments thereof present in the DNA product previously prepared. Again, only a very few of these clones will contain the gene for IFN-α or fragments thereof (FIG. 1). The preferred host for initial cloning in accordance with this invention is *E. coli* HB 101. Other experiments were conducted with *E. coli* X1776, a host described in British patent 1,516,458 and placed on deposit with the American Type Culture Collection, Rockville, Md., USA, where it has been assigned ATCC No. 31244.

1. Preparation of PstI-Cleaved, dGMP-elongated pBR322

Plasmid pBR322 (20 μg) was digested with 21 units PstI endonuclease (MRE Porton Downs or New England Biolabs) in 150 μl 10 mM Tris-HCl (pH 7.5), 6 mM $MgCl_2$, 50 mM NaCl, 6 mM 2-mercaptoethanol, 200 mg/μl bovine serum albumin ("BSA") (Calbiochem). After 2 h at 37° C., the mixture was extracted with 1 vol phenol-chloroform (1:1) and 1 vol ether and precipitated with ethanol.

Addition of homopolymeric dGMP tails (FIG. 1) by terminal deoxynucleotidyl transferase (TdT) (purified according to F. J. Bollum, "Deoxynucleotide Polymerizing Enzymes From Calf Thymus Gland", in *Methods in Enzymology*, (L. Grossman and K. Moldave, eds.), Academic Press, New York, 128, pp. 591–611 (1968)) was done in a 328-μl reaction volume containing 100 mM sodium cacodylate (pH 7.2), 10 mM NaH2PO4, 5 mM $MgCl_2$ 1 mM dGTP, 50 μμg/μl BSA, and 3–6 units of TdT (purified as above) per μg of DNA. Incubation was at 37° C. for 20 min. EDTA was added to 10 mM and the mixture extracted as above and dialyzed for 2 days against TNE buffer.

2. Preparation of dCMP-elongated DNA

Double-stranded DNA was elongated with dCMP residues by standard procedures (Eg., Villa-Komaroff et al., supra). 150 ng of the double-stranded cDNA described above were incubated in 8 μl 100 mM sodium cacodyiate (pH 7.2), 2.5 mM $CoCl_2$, 50 μg/μl BSA, 0.1 mM. dCTP containing 3–6 units of purified TdT per μg of DNA for 8 min at 27° C. and then frozen at −20° C. As before, the dCMP-elongated DNA is a mixture of different species, only a very few of which are IFN-related (FIG. 1).

3. Preparation of $Ca^{++}$-Treated *E. coli* X1776

A single colony of *E. coli* X1776 was inoculated into 100 ml tryptone medium (C. Weissmann and W. Boll, "Reduction Of Possible Hazards In The Preparation Of Recombinant Plasmid DNA", *Nature*, 261, pp. 426–29 (1976), supplemented with 100 μg/ml diaminopimelic acid (Xoch-Light Laboratories), 10 μg/ml nalidixic acid (Calbiochem) and 10 ug/ml tetracycline (Achromycin®, American Cyanamid). The culture was grown at 37° C. to an apparent optical density of 0.6 at 650 nm ($OD_{650}$) (as measured in a Beckman DB spectrophotometer) and chilled in ice for 30 min. The culture was then sedimented at 4000 rpm in a Sorvall H4 swinging bucket rotor, the cells washed with 50 ml 10 mM NaCl, repelleted by centrifugation, and resuspended in 20 ml 100 mM $CaCl_2$. The suspension was cooled in ice for 30 min, pelleted by centrifugation and resuspended in 4 ml of 100 mM $CaCl_2$ and kept on ice overnight for use. *E coli* EB101 was prepared for transformation by the method of M. Mandel and A. Higa, "Calcium-Dependent Bacteriophage DNA Infection", *J. Mol. Biol.*, 53, pp. 159–62 (1970). Aliquots (0.5 ml) were kept frozen at −70° C. and retained their activity for at least 3 months.

4. Annealing of dGMP-elongated pBR322 and dCMP-elongated DNA

The annealing of the tailed, PstI-cleaved pBR322 and tailed cDNA was as described in J. Van den Berg et al., "Comparison Of Cloned Rabbit And Mouse β-globin Genes Showing Strong Evolutionary Divergence Of Two Homologous Pairs Of Introns", *Nature*, 276, pp. 37–44 (1978). 8 ng of dCMP-elongated DNA product were mixed with 22 ng of dGMP-elongated PstI-cleaved pBR322 in 50 μl TNE buffer. Incubation was for 4 successive 1 h stages at 65° C., 46° C., 37° C. and 20° C. 20 μl 100 mM Tris-HCl (pH 7.5), 100 mM $CaCl_2$, 100 mM $MgCl_2$ and 50 μl TNE buffer were-added and the mixture cooled in ice for 20 min.

The product is, of course, a large mixture of different recombinant DNA molecules and some cloning vehicles without inserted DNA sequences. However, each recombinant DNA molecule contains a cDNA segment at the PstI site. Each such cDNA segment may comprise a gene or a fragment thereof. Only a very few of the cDNA segments code for IFN or a portion thereof (FIG. 1). The vast majority code for one of the other proteins or portions thereof whose mRNA's were part of the poly(A) RNA used in the process of this invention (FIG. 1).

S. Transfection Of *E. coli* X1776 with the Annealed Hybrid Plasmids

The transfection of *E. coli* X1776 with the mixture of recombinant DNA molecules was as described in J. Van den Berg et al., supra. P3 containment facilities were used for the transfection process and all subsequent steps in which the resulting transformed bacteria were. handled. The annealed pBR322 recombinant DNA molecules were added to 100 μl of $Ca^{++}$-treated *E. coli* Xl776,. prepared previously, and the mixture cooled in ice for 20 min, heated at 20° C. for 10 min, and 0.6 ml tryptone medium added. The mixture was plated onto.2 tryptone medium agar plates supplemented as above. Transfection efficiency was $3.3\times10^4$ colonies per μg of annealed pBR322 transfecting DNA; native pBR322 gave $3\times10^6$ colonies per μg.

Since plasmid pBR322 includes the gene for tetracycline resistance, *E. coli* hosts which have been transformed with a plasmid having that gene intact will grow in cultures containing that antibiotic to the exclusion of those bacteria not so transformed. Therefore, growth in tetracycline-containing culture permits selection of hosts transformed with a recombinant DNA molecule or recyclized vector.

After 48 h at 37° C., individual colonies were picked and suspended in 100 μl tryptone medium (supplemented as above) in the wells of microtiter plates (Dynatech). After incubation at 37° C. overnight, 100 μl 40% glycerol were mixed into each well. The plates were stored at −20° C. and a library of 100,000 individual clones of transformed *E. coli* X1776 was prepared.

Figure 2:
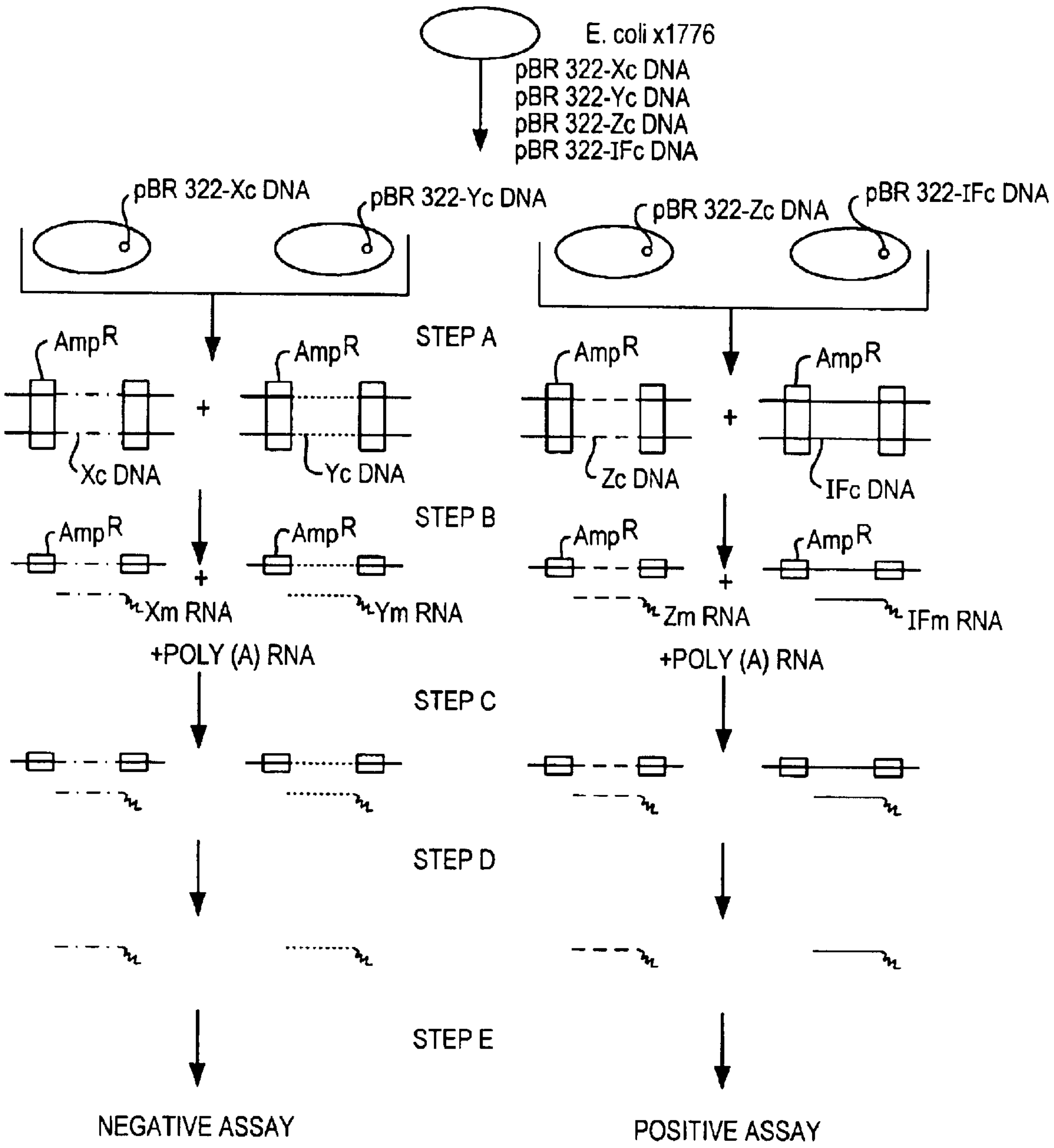
FIG. 2 is a schematic outline of the initial clone screening process of this invention.

These 100,000 clones contain a variety of recombinant DNA molecules representing complete or partial copies of the mixture of mRNAs in the poly(A) RNA preparation from IFN-producing leukocytes (FIG. 2). The majority of these will contain only a single recombinant DNA molecule. Only a very few of these recombinant DNA molecules are related to IFN. Accordingly, the clones must be screened to separate the IFS-related clones from the others.

Screening for a Clone Containing HuIFN-αcDNA

There are several approaches to screen for bacterial clones containing human leukocyte interferon cDNA ("HuIFN-αcDNA"). These include, for example, RNA selection hybridization (Alwine et al., infra), differential hybridization (T. P. St. John and R. W. Davis, "Isolation Of Galactose-Inducible DNA Sequences From Saccharomyces Cerevisiae By Differential Plague Filter Hybridization", *Cell*, 16, pp.

443–452 (1979); Hoeijmakers et al., infra), hybridization with a synthetic probe (B. Noyes et al., "Detection And Partial Seguence Analysis Of Gastrin mRNA By Using An Oligodeoxynucleotide Probe", *Proc. Natl. Acad. Sci. USA*, 76, pp. 1770–1774 (1979)) or screening for clones that produce the desired protein by immunological (L. Villa-Komaroff et al., supra) or biological (A. C. Y. Chang et al., supra) assays we have chosen RNA selection hybridization as being the most convenient and promising method for primary screening of clones con- taining IFN-αcDNA.

A. RNA Selection Hybridization Assay

1. Overview of the Initial Assay

Referring now to FIG. 2, recombinant DNA was isolated from a culture of a mixture of 512 clones from the above library of clones (two mixtures of 2 clones shown in FIG. 2) (Step A). The reason for selecting this batch size will be explained below. The recombinant DNA molecules were cleaved, denatured and hybridized to leukocyte poly(A) RNA containing IFN-αmRNA prepared as before (Step B). All recombinant DNA molecule-poly(A) RNA hybrids were separated from the non-hybridized poly(A) RNA (Step C). The poly(A) RNA was recovered from the hybrids and purified (Step D). The recovered RNA was assayed for IFN-αmRNA activity as above (Step E). If, and only if, the mixture of recombinant DNA molecules contains a recombinant DNA molecule having an inserted nucleotide sequence capable of hybridizing to the IFNmRNA in the poly(A) RNA under stringent hybridization conditions, will the mRNA released from that hybrid cause the formation of IFN-α in oocytes, because mRNA released from any other recombinant DNA molecule-poly(A).RNA hybrid will not be IFN-α-related. If a group of 512 clones gave a positive response, the clones were regrouped in 8 lots of 64, and each lot assayed as before. This process was continued until a single clone responding to this assay was identified.

There is no assurance that the recombinant DNA molecules and bacterial clone transformed therewith, which are thus identified, contain the complete IFN-αcDNA sequence of IFN-α or even that the DNA sequence actually codes for IFN-α. However, the recombinant DNA molecules will certainly contain extensive nucleotide sequences complementary to the IFN-αmRNA coding sequence. Therefore, the recombinant DNA molecule may at least be used as a source of a probe to screen rapidly other recombinant DNA molecules and clones transformed with them to identify further sets of clones which may contain an authentic and complete IFN-α nucleotide coding sequence.

2. Theoretical Considerations

The conditions for the hybridization (Step B) are critical. The absolute concentrations and the ratio of recombinant DNA molecule and poly(A) RNA must be chosen so as to take into consideration reaction rate and stoichiometry. The proper choice is difficult to make, because the proportion of IFN-αmRNA in the poly(A) RNA is not known. In order to assure controlled and adequate kinetics, the hybridization was carried out under conditions where the concentration of DNA sequences from the recombinant DNA molecules was in excess as compared to the estimated IFN-αmRNA concentration. In a mixture of 512 possible different recombinant DNA molecules, an IFN-a-related DNA sequence ("IFN-αR DNA") will either not occur (giving a negative assay), or it will constitute at least about 1/512 of the recombinant DNA molecules. The concentration of the recombinant DNA molecule mixture and therefore the concentration of the IFN-αR DNA, if any, can thus be adjusted in the hybridization step to ensure adequate hybridization rates. In addition, the amount of the IFN-αR DNA in the reaction mixture must be sufficient to bind enough IFN-αmRNA from the poly(A) RNA to allow detection of IFN-α after injection into oocytes of the mRNA recovered from the recombinant DNA molecule-poly(A) RNA hybrid.

In order to detect IFN-α by the assays available, its concentration should be 100 IU/ml or higher. Because 0.5 ml aliquots are required for replicate determinations, 50 IU should be generated in the oocytes. The poly(A) RNA from induced leukocytes, used previously, generates about 500 IU IFN-α upon injection of 1 μg into oocytes. Therefore, at least 0.1 μg poly(A) RNA has to be injected to generate the needed 50 IU. Model experiments with rabbit globin mRNA and rabbit β-globin cDNA clones showed that the overall recovery of $^{125}$I-globin mRNA in the oocyte relative to $^{125}$I-globin mRNA added to the hybridization mix was about 10%, and the recovery of mRNA activity about 5%. Therefore, at least 0.1/0.05 =2 μg of leukocyte poly(A) RNA should be used for the hybridization assay. To ensure an adequate safety margin, 12 μg of poly(A) RNA were used per assay.

To calculate how much DNA from the recombinant DNA molecules is required to bind the IFN-αmRNA in 12 μg of poly(A) RNA, the IFN-αmRNA content of poly(A) RNA was estimated. On μg of poly(A) RNA generates 500 IU of IF. The specific activity of IFN-α lies between $2\times10^8$ and $10^9$ IU/mg protein. 500 IU of IFN-α therefore correspond to between $500/2\times10^8=2.5\times10^{-6}$ mg (2.5 ng) and $500/10^9=5\times10^{-7}$ mg (0.5 ng) of interferon.

The relationship between the amount of IFN-αmRNA injected into an oocyte and the amount of IFN-α produced is unknown. In the case of β-globin mRNA, about 30 molecules of protein per molecule mRNA are produced per hour; this value is about 6 for β-globin (J. B. Gurdon et al., "Message Stability In Injected Frog Oocytes: Long Life of Mammalian And β-Globin Messages", *J. Mol. Biol*., 80, pp. 539–51 (1973)). Assuming an average value of 20 for IFS-α, molecular weight of 18000 for IFN-α and a molecular weight of 330,000 for IFN-αmRNA, then 26 mg (18000/330000×20×24) of IFN-α should be produced in 24 h per mg of IFN-αmRNA injected. If the specific activity of IFN-α is $2\times10^8$/mg ($2\times10^2$ IU/ng), then 1 ng IFN-αmRNA will yield $26\times2\times10^2=5.2\times10^3$ IU of IFN-α. If the specific activity is $10^9$/g ($10^3$ IU/ng), the amount of IFN produced would be $2.6\times10^4$ IU. Because 1 μg of leukocyte poly(A) RNA yields 500 IU of IFN-α, under the above assumed conditions, the concentration of IFN-αmRNA in 1 μg poly(A) RNA would fall between 0.1 ng to 0.02 ng and the proportion of IFN-αmRNA in leukocyte poly(A) RNA would lie between 1:10,000 and 1:50,000. Therefore, 12 μg of poly(A) RNA contains about 1.2 ng to 0.2 ng IFN-αmRNA.

Should the translation ratio of the IFN-αmRNA in the oocytes be lower by an order of magnitude than the average for globin mRNA, the IFN-αmRNA content of the poly(A) RNA would be 10 times higher than calculated above, or between about 1:1000 to 1:5000. And, 12 μg of poly(A) RNA would then contain about 12 ng to 2 ng of IFN-αmRNA. On the other hand, should the translation ratio of the IFN-αmRNA in the oocytes be higher by an order of magnitude than the average for globin mRNA, the IFN-αmRNA content of the poly(A) RNA would be 10 times lower t ancalculated above, or between about 1:100,000 and 1:500,000. And, 12 μg of poly(A) RNA would then contain 0.1 ng to 0.02 ng IFN-αmRNA.

Plasmid pBR322 has 4361 b.p. The complete cDNA of IFN-αmRNA would add about 800–1000 b.p. to pBR322 on formation of pBR322-IFN-αcDNA to a total of about 5200–5400 b.p. Its molecular weight would thus be about 12 times (2×5200/800) that of the IFN-αmRNA alone. Therefore, in order to bind the IFN-αmRNA calculated above to be present in 12 μg poly(A) RNA required for the assay, an amount of recombinant DNA molecules equal to 12 times the amount of the IFN-αmRNA will be required (stoichiometric amount).

Because the IFN-αmRNA content of the poly(A) RNA used to prepare the recombinant DNA molecules had been increased 10 to 40-fold over that of the crude poly(A) RNA, the group of 512 clones should have 10 to 40 times more clones containing the desired IFN-αmRNA than calculated from the above.

If IFN-αmRNA is 1 part in 1000 of the crude poly(A) RNA, then 12 μg of poly(A) RNA contain 12 ng IFN-αmRNA and the stoichiometric amount of IFN-αcDNA plasmid is 144 ng. Since a group of 512 clones will contain at least 5 with IFN-αcDNA inserts, the amount of total hybrid plasmid DNA required is 14.8 μg ($144\times512/5\times10^{-3}$). If IFN-αmRNA is 1 part in 10,000, then 12 μg of poly(A) RNA contain 1.2 ng IFN-αmRNA and the amount of IFN-αcDNA plasmid required is 14.4 ng. A group of 512 clones will contain either 0 or 1 IFN-αcDNA insert, so that the amount of total hybrid plasmid DNA required is 7.4 μg ($14.4\times512\times10^{-3}$). If IFN-αmRNA is 1 part in 100,000, then the amount of total hybrid plasmid DNA required is 0.74 μg ($1.44\times512\times10^{-3}$). In order to ensure that the hybridization reaction will proceed under DNA excess conditions (i.e., excess recombinant DNA as compared to poly(A) RNA), 20 μg of the mixture (about 1.4 to 30-fold excess) was chosen for the assay.

Hybridization must be conducted under conditions which ensure (a) that the hybridized portion of the poly(A) RNA is recovered intact and in a biologically active form, (b) that non-specific DNA-mRNA association is prevented, and (c) that the hybridization reaction goes to at least 75% completion. These conditions are most likely to be met by hybridization in 80% formamide, 0.4M NaCl (J. Casey and N. Davidson, "Rates Of Formation And Thermal Stability Of RNA:DNA And DNA:DNA Duplexes At High Concentrations Of Formamide", *Nucleic Acids Res*., 4, pp. 1539–52 (1977)). In this solution, hybridization can be conducted at about 40° C. (rather than the 60°–70° C. required when formamide is omitted). Lower temperatures are preferred to minimize damage to the poly(A) RNA. We chose a hybridization temperature of 56° C. This is about 3° below the $T_{1/2i}$ (J. Casey and N. Davidson, sudra) and about 10–13° below $T_{1/2d}$ (Hamaguchi & Geidushek, *J. Amer. Chem. Soc*., 84, p. 1329). Therefore, this temperature should not allow hybridization of sequences with less than about 87% homology, since a 1% mismatch lowers the $T_{1/2d}$ by 1° (T. F. Bonner et al., "Reduction In The Rate Of DNA Reassociation By Sequence Divergence", *J. Mol. Biol*., 81, pp. 123–35 (1973)).

In the present hybridization, self-hybridization of DNA is not a major problem because the mixture of DNA's being used consists of the same vector (pBR322) and a variety of cDNA inserts. Therefore, most of the DNA sequences will be heteroduplexes in which the inserts are available for hybridization to poly(A) RNA. It is very unlikely that complementary cDNA inserts which form part of different duplexes will interact because of topological constraints. In any event, DNA:DNA reassociation is minimized under the reaction conditions used (J. Casey and N. Davidson, supra).

To determine the hybridization time required to ensure at least 75% reaction, a second order rate equation was employed:

$$t = \frac{\ln\dfrac{Co - Ro + Ro\left(1 - \frac{R}{Ro}\right)}{\left(1 - \frac{R}{Ro}\right)Co}}{k_R(Co - Ro)} = 3.9\ h$$

where:

R=molar nucleotide concentration of hybridized RNA

Co=molar nucleotide concentration of initial DNA to be hybridized

Ro=molar nucleotide concentration of initial RNA to be hybridized $k_R$=rate constant for RNA-DNA hybridization t=time (sec)

and:

$$\frac{R}{Ro} = 0.75 \text{ (75\% reaction completion)}$$

$k_R$=472 ($k_R$=1/12$k_d$ (J. Casey and N. Davidson, supra)

where:

$k_d$=second order rate constant for DNA under the chosen conditions of hybridization and:

$k_d=1.7\times10^5\times L^{1/2}\times N^{-1}$ (J. R. Hutton and J. G. Wetmur, "Renaturation Of Bacteriophage 8×X174 DNA-RNA Hybrid: RNA Length Effect And Nucleation Rate Constant", *J. Mol. Biol*., 77, pp. 495–500 (1973))

L=900 (chain length in b.p.; about 900 are present in the full IFN-αcDNA insert)

N=900 (complexity in b.p. of the hybrid chain; here the complexity is 900 because the 900 nucleotides of the IFN-αmRNA join with the complementary 900 nucleotides of the IFN-αcDNA insert)

$Co=2.5\times10^{-7}$ (Based on a 40 μl solution containing the previously determined 20 μg of recombinant DNA molecules to be used in the assay, again assuming that the IFN-αcDNA insert will be 1/12 of a recombinant DNA molecule and will occur in at least 1 of the 512 clones, and assigning 662 as the average molecular weight of one DNA base pair)

$Ro=8.7\times10^{-8}$ (Based on a 40 μl solution containing the previously determined 12 μg of poly(A) RNA to be used in the assay, again assuming that the poly (A) RNA contains 1:10,000 parts IFN-αmRNA (given the large excess of DNA a different proportion will have little effect on the rate of hybridization) and assigning 343 as the average molecular weight of one ribonucleotide of RNA)

3. Execution Of The Initial Assay

Step A—Preparation and Cleavage of the Recombinant DNA Molecule Mixture

The desired number of bacterial clones was inoculated onto tryptone medium agar plates supplemented as above, by transferring to it an aliquot from each microtiter well with use of a mechanical device. After incubation at 37° C., each clone had given rise to a colony of several m diameter. All colonies were washed off the plate(s) and pooled to give an inoculum used to inoculate 1 l of tryptone medium supplemented as above in a 21 Erlenmyer flask. The culture was shaken at 37° C. to an apparent $OD_{850}$ of about 0.8 (estimated visually). One volume of supplemented tryptone medium and chloramphenicol to 170 μg/ml were added to the culture which was further shakez at 37° C. for 16 h. 20 ml chloroform were added and the culture shaken again for 10 min at 37° C. to kill the bacteria (C. Weissmann and W. Boll, supra). The culture was decanted from the chloroform and the cells were harvested by centrifugation (Sorvall GS3 rotor) for 15 min at 6000 rpm and 4° C. About 1–2 g of cells were obtained for each 1-liter preparation. The cells were suspended in 30 ml 20 mM Tris-HCl (pH 7.5), centrifuged for 20 min at 5000 rpm and 40° C. (Sorvall SW rotor) and resuspended in 30 ml 50 mM Tris-HCl (pH 7.5). 0.25 vol of lysozyme solution (10 mg/ml in 50 mM Tris-HCl (pH 7.5)) were added and after cooling for 10 min at 0° C. 0.33 vol (based on the vol of the original 50 mM Tris-HCl-culture suspension) 0.5 M EDTA (pH 8.0) were gently mixed in without shaking. After another 10 min at 0° C., 1/16 vol (again based on the original volume) of 2% Triton X-100 were added. After 60 min, the sample was centrifuged for 60 min at 10,000 rpm and 0° C. in a Sorvall SW rotor. The supernatant was transferred to a beaker containing a magnetic stirrer, and 3M NaOR was added with stirring until a pH of 12.5 was reached, as measured at 20° C., using a glass electrode and an Orion Research model 601 pH meter, standardized with Beckman pH 10 Carbonate Buffer Standard (No. 3505). After stirring 10 min at 20° C., the pH was adjusted to 8.5. After 3 min further stirring 1/6 vol 5 M NaCl and 1 vol phenol (distilled and equilibrated with 9.5 M NaCl) were added and vigorous stirring continued for 5 min. The phases were separated by centrifugation (GSA Sorvall rotor) at 10,000 rpm and 0° C. for 10 min. The supernatant containing Form I DNA (circular double-stranded DNA). was carefully removed from the interphase (which contact single-stranded DNA) and extracted 3 times with chloroform. (Phenol must be largely removed at this step). The Form I DNA fraction will contain those recombinant DNA molecules (pBR322-cDNA insert) originally used in transforming those host cells which form part of the 512 clones chosen for assay.

Pancreatic RNAase A (5 mg/ml, preheated 10 min at 85C) was added to the Form I DNA to a concentration of 20 μg/ml and the mixture incubated 60 min at 37° C. 1/5 vol 5 M NaCl were added and the mixture adjusted with 30% polyethylene glycol 6000 (Union Carbide, autoclaved 20 min at 120° C.) up to a final concentration of 7.5% PEG. After 2–16 h at −10° C., the precipitate was collected in a Sorvall SW Rotor for 20 min at 8,000 rpm and 0° C., dissolved in 0.075 M NaCl, 0.007 M Na-citrate to an absorbance of 20 at 260 nm, and adjusted to 0.5% SDS. The solution was incubated for 30 min at 37° C. with 0.5 mg/ml Pronase (self-digested at 20 mg/ml, 2h at 37° C.). and extracted 3 times with 1 vol distilled phenol and 2 times with 1 vol chloroform. The sample (up to 2 ml of a 1 mg/ml DNA solution) was centrifuged through a 5 to 23% sucrose gradient in 50 mM Tris-HCl (pH 7.5), 1 mM EDTA for 15 h at 21,000 rpm and 15° C. using an SW 27 Beckman Rotor. Fractions were collected and the $OD_{280}$ monitored. DNA-containing fractions were pooled and the DNA precipitated with sodium acetate and ethanol. 20 to 100 μg of the Form I DNA mixture were recovered by centrifugation.

Twenty μg of purified Form I DNA were digested in 150 μl 10. mM Tris-HCl (pH 7.5), 6 mM $MgCl_2$, 50 mm NaCl, 6 mM 2-mercaptoethanol, 200 μg/ml BSA or gelatin and 20 units HindIII (New England Biolabs). The HindIII restriction enzyme cleaves the Form I DNA at a site within the pBR322 moiety (It is unlikely that the cDNA moiety is also cleaved, but if it is, the assay should not be substantially affected). After 2 h at 37° C., an aliquot (1%) was analyzed by electrophoresis through a 1% agarose gel in 50 mM Tris-αcetate (pH 7.8), 2 mM EDTA for 1 h at 50 mA to ascertain whether digestion was complete. If digestion was not complete, more HindIII was added and incubation continued for 2 h. When the Form I DNA was converted totally to linear molecules, Pronase (Calbiochem),. EDTA and SDS were added to 0.5 mg/ml, 10 mM and 0.5% respectively. After 30 min at 37° C., the solution was extracted with 30 μl phenol-chloroform (1:1). The organic phase was washed with 50 μl 20 mM Tris-HCl (pH 7.5), 1 mM EDTA, and the combined aqueous phases extracted 3 times with ether, filtered through a 0.1-ml Chelex column, collected in an EDTA-boiled Pyrex® tube and precipitated with 1/10 vol 3M sodium acetate and 2.5 vol ethanol. After standing overnight at −20° C., the DNA was collected by centrifugation.

Step B—Hybridization of the DNA with Poly(A) RNA

Two hybridization mixtures were prepared. Mixture I contained 4 μl of 10-fold concentrated hybridization buffer (4M NaCl, 0:1 PIPES (pH 6.4, 1,4 piperazine-diethane sulfonic acid, Sigma), 50 mM EDTA, 0.5 μl (about 5 ng $^{125}$I-globin mRNA (5000 cpm) and 6 μl induced leukocyte poly(A) RNA (2 μg/μl), an amount sufficient to generate 6000 IU of IFN when injected into oocytes. Mixture II contained 10 μg of the HindIII digested Form I DNA from above and 0.1 μg of PstI-digested Z-pBR322(H3)/RcβG-4.13 (a pBR322 derivative that contains the β-globin sequence in the HindIII site) (Mantei et al., "Rabbit β-globin mRNA Production In Mouse L Cells Transformed With Cloned Rabbit β-globin Chromosomal DNA"., *Nature*, 281, pp. 40–46 (1979).). The $^{125}$I-globin mRNA in mixture I and the β-globin DNA in mixture II serve as internal positive controls for the hybridization assay. Both mixtures were dried in a stream of nitrogen gas. 40 μl of 80% formamide were added to the residue of mixture II and the solution was denatured for 10 min at 100° C. and chilled quickly in ice. The denatured solution was used to dissolve the residue of mixture I and the resulting solution incubated at 56° C. for 4 h.

Step C.—Separation of Hybridized Poly(A) RNA-DNA from Non-Hybridized Poly(A) RNA After dilution to 1 ml with cold 0.9 M NaCl, 0.09 M Na-citrate and formamide (100%) to 4% (by volume) the solution was filtered at 0.5 ml/min through a Millipore filter (0.45 μm pore size), the filter having been first tested for its capacity to retain RNA-DNA hybrids, because not all filters obtained from the manufacturer were equally efficient.

Step D—Purification of Hybridized Poly(A) RNA

The above filter, with poly(A) RNA hybrids attached, was immersed in 1 ml 0.15 M NaCl, 0.015 M Na-citrate, 0.5% SDS for 10 min at 37° C., rinsed with 50 mM Tris-HCl (pH 7.5), 10 mM $MgCl_2$, 2 mM $CaCl_2$ and placed in 0.6 ml of fresh buffer. After the addition of 5 μl iodoacetate-treated DNAase (5mg/ml) (S. B. Zimmermann and G. Sandeen, *Anal Biochem*., 14, p. 269 (1966); P. A. Price et al., "Alkylation Of A Histidine Residue At The Active Site Of Bovine Pancreatic Deoxyribonuclease", *J. Biol. Chem*., 244, pp. 924–32 (1969)), the filter was incubated at 37° C. for 10 min.

The filter was removed and the solution extracted with lvolphenol and 1 vol ether and passed through a 0.1-ml Chelex column. 5 μg of carrier RNA (purified yeast RNA) were added to the solution and the RNA precipitated with sodium acetate and ethanol. The precipitate was collected by centrifugation at 10,000 ×g, dissolved in 100 μl 1 mM EDTA, heated for 90 sec at 100° C., and TNE and SDS added to 2×TNE and 0.5% SDS. The RNA was adsorbed to a 100-μl oligo(dt) cellulose column, eluted with four washes of 0.3 ml distilled water and precipitated with sodium acetate and ethanol. After 16 h at −20° C. the precipitated. RNA was separated by centrifugation and dissolved in 2 μl TNK buffer.

Step E—Determination of IFN-αmRNA Activity

The poly(A) RNA solution from above was injected into 40 oocytes (about 50 nl per oocyte). The occytes were incubated at 23° C. for 24–48 hours, homogenized and centrifuged (or the incubation medium recovered) and assayed as described previously for IFN-α.

4. Subsequent Assay—Hybridization to Filter-bound DNA

Most subsequent assays of a recombinant DNA molecule from a single clone were carried out with DBM or DPT paper-bound DNA, because the assay conditions were no longer critical and the assay is more convenient. DPT paper gave lower backgrounds and was used preferentially. DBM paper was prepared as described (J. C. Alwine et al., "Method For Detection Of Specific RKAs In Agarose Gels By Transfer To Diazobenzyl oxymethyl-Paper And Hybridization With DNA Probes", *Proc. Natl. Acad. Sci. USA*, 14, p. 5350–54 (1977)). APT paper was prepared by a procedure of B Seed (pers. commun.): Sheets of Whatman 540 paper (20 g) were agitated for 16 h at 20° C. with a mixture of 70 ml 0.5 M NaOH, 2 mg/ml NaBE4 and 30 ml 1,4-butanediol diglycidyl ether. The paper was then transferred to a solution of 10 ml 2-aminothiophenol in 40 ml acetone and agitated for 10 h. The paper was exhaustively washed with acetone, 0.1 N HCI, HCl, $H_2O$, 0.1 N HCl, $H_2O$ and dried. APT paper was diazotized to DPT paper as described for the conversion of ABM to DBM paper (Alwine et al., supra).

DNA (up to 15 μg) was bound to 50 $mm^2$ diazotized ABM (DBM) or diazotized APT (DPT) paper as described by J. H. J. Hoeijmakers et al. "The Isolation Of Plasmids Containing DNA Complementary To Messenger RNA. For Variant surface Glycoproteins Of Trypanosoma Bruceill", *Gene*, in press, 1980) and set forth below.

Hybrid plasmid DNA was digested with endonucle- ase PstI, treated with 500 μg Pronase per ml, 0.5% SDS, and 10 mM EDTA for 30min at 37° C., extracted with phenol and ether, passed through a 0.1-ml Chelex column, and precipitated with ethanol. The heat-denatured DNA (up to. 5 μg, with a small amount of $^{32}$P-DNA added astracer) was incubated overnight at 0° C. with 1 $cm^2$ DBM or DPT paper in 200 μl 25 mM potassium phosphate buffer (pH 6.5). Filters were washed three times for 5 min at room temperature with 50 mM potassium phosphate buffer (pH 6.5), 1% glycine and three times with 99% recrystallized formamide. A further incubation with 99% formamide for 2 min at 68° C. was followed by three washes in 50 mM potassium phosphate buffer (pH 6.5) at 20° C. and two washes in 0.4 M NaOH at 37° C. for 10 min. About 40–60% of the radioactivity was retained on the filters. The filters were incubated for 3 h at 38° C. in pre-hybridization medium A, supplemented with 1% glycine, using 330 μl per filter. Medium A contains 50% formamide, 5×SSC, 0.04% polyvinyl pyrrolidone, 0.04% Ficoll (Pharmacia), 0.1% SDS, 25 μg poly(A) (P & L) and 100 μg yeast RNA (BDH, extracted six times with phenol and precipitated with ethanol). The filters were washed twice in medium A and then hybridized for 16 h at 38° C. with poly(A) RNA as indicated (usually 5–8 μg) in medium A under paraffin oil. The RNA was added as follows: one wet DNA filter was blotted and put in a sterile Petri dish, 20–40 μl of the RNA solution were pipettedon this filter and a second DNA filter (either a duplicate or a control) was put on top and the sandwich was covered with a sterile paraffin oil. After the hybridization the filters were successively washed in medium A (2 times), in a solution containing 1×SSC, 0.2% SDS, 1 mM EDTA (3 times, 10 min at 20° C. each), medium A (2 h at 38° C.) and in 50% formamide, 5×SSC, 0.1% SDS (3 times, 10 min at 20° C.). Hybridized RNA was eluted by heating for 1 min at 100° C. in 200 μl 10 nM Tris-ECl (pH 7.4), 1 mM EDTA and 0.1% SDS. The elution step was repeated twice, the eluates were combined and the RNA was precipitated with ethanol after addition of 2 μg yeast RNA (purified as above). The washed pellet was vacuum dried, dissolved in 3 μl $H_2O$ and injected into oocytes. IFN-α activity was assayed as above.

5. Results of the RNA Selection Hybridization Assay

The assays from 8 groups of 512 clones (i.e., groups T, Y, j, K, •, O, ε and π were negative. The assays from 4 groups of 512 clones (i.e., groups I, δ, N and λ) were positive, albeit not consistently. The positive assays are reported in the following format: IU/ml of IFN-α produced by the RNA released from poly(A) RNA-DNA hybrid (assay from control hybridization using Z-pBR322(H3)/Rcβ G-4.13, supra); the assays in which the experimental results were higher than the background control are underscored.

| Group | IU/ml |
|---|---|
| I | <60 (<60); 110 (<20); <110 (<110); <110 (<110); <35 (<35) |
| δ | 20 (<20) |
| N | 35 (<20); <110 (<110); 200 (<110) |
| λ | <60 (<60); 60 (<20); <110 (<110); <110 (<110) |

Group λ was subdivided into 8 subgroups of 64 clones and hybridized and assayed as before. The subgroups gave the following results, presented in the same format as above:

| Subgroup | IU/ml |
|---|---|
| λ-I | <35 (<35); <35 (<35) |
| λ-II | 130 (<30); <45 (<45) |
| λ-III | 225 (<35); 35 (<30); 35 (<30); 600 (<30); <20 (<20) |
| λ-IV | 85 (<35); <25 (<25) |
| λ-V | <35 (<35) |
| λ-VI | <35 (<35) |
| λ-VII | <35 (<35) |
| λ-VIII | <35 (<35) |

subgroup λ-III was subdivided into 8 sets of 8 clones, and hybridized and assayed:

| Set | IU/ml |
|---|---|
| λ-III-1 | <20 (<20); <20 (60); 35 (<30) |
| λ-III-2 | <35 (<35); <30 (<30); 150 (<20); 600 (<35); 110 (60) |
| λ-III-3 | <25 (<25); <30 (<30) |
| λ-III-4 | 30 (<30); <20 (<20); <20 (60) |
| λ-III-5 | 30 (?) (<35); <20 (<20); <35 (60) |
| λ-III-6 | <30 (<30); <20 (<20) |
| λ-III-7 | <30 (<20) |
| λ-III-8 | <30 (<20) |

Because the first positive result was achieved with the set λ-III-4, the individual colonies of this set (designated A to B) were hybridized and assayed:

| | |
|---|---|
| λ-III-4-B | <35* (<35): <20 (60) |
| λ-III-4-C | 35 (60); <u>60</u>* (<35); <u>111</u>* (<11); 11* (<11); <u>20</u> (<20) |

*The DBM paper method was used in this assay.

Therefore, clone λ-III-4-C contains a recombinant DNA (molecule capable of hybridizing IFN-αmRNA.

The recombinant DNA molecule in this clone is designated: Z-pBR322(Pst)/HcIF-4C ("Hif-4C"), and the bacterial strain containing it: *E. coli* X1776 (Z-pBR322 (Pst)/HcIF-4C) ("*E. coli* Hif-4C"). This nomenclature indicates that the recombinant DNA molecule originated in Zurich (Z) and is plasmid pBR322 containing at the PstI site a HIFN-αcDNA ("HcIF"); the particular recombinant DNA molecule being derived from clone λ-III-4-C ("4C").

Recloning and Characterization of Z-pBR322(Pst)/HcIF-4C

Since primary clones of transformed cells occasionally contain more than one species of recombinant DNA molecule (Efstratiadis et al., "The Primary Structure Of Rabbit β-globin mRNA As Determined From Cloned DNA", Cell, 10, pp. 571–85 (1977)), Hif-4C was isolated from *E. coli* X1776 (Hif-4C) clones and purified as described above. Samples of Hif-4C and pBR322 were digested with PstI and analyzed by electrophoresis on a 1% agarose gel. Hif-4C gave two bands, one with the mobility of Pst-cleaved pBR322, the other with a mobility corresponding to about 320 b.p.

*E. coli* HB101 was transformed with the isolated Hif-4C as described above. Six clones of tetracycline-resistant, transformed bacteria were picked, small cultures prepared and Form I DNA purified and analyzed by PstI cleavage and agarose gel electrophoresis as before. All samples showed cleavage patterns identical to Hif-4C. One of these recloned-recombinant DNA molecules was designated Z-pBR322 (Pst)/HcIF-4c ("Hif-4c") and used for further experimentation. The lower case "C" designates a recloned DNA molecule.

To determine the capacity of Hif-4c and its cDNA insert to hybridize to IFN-αmRNA, Hif-4c (115 μg) was digested to completion with 125 units of PstI, extracted with phenol and chloroform, and precipitated with ethanol as described above. An aliquot (10 μg) was 5' terminally labeled (to serve as a tracer in subsequent steps) by dissolving it in 100 μl 50 mM Tris-HCl (pH 7.5), passing it through a 0.1-ml1 Chelex 100 column and treating it with 0.6 units bacterial alkaline phosphatase for 1 h at 65° C. Tenfold concentrated TNE (40 μl) was added and the solution extracted 3 times with 1 vol phenol and 3 times with 1 vol chloroform. The DNA was precipitated with 2 vol ethanol at −20° C. overnight and collected by centrifugation. For further purification, the sample in 0.5 ml TNA was adsorbed to 0.25-ml DEAE cellulose (Whatman DE52, prewashed with 2 ml 150 mM NaCl, 50 mM Tris-HCl (pH 7.5), 2 mM EDTA) ("NET-buffer"), washed with 2 ml of NET buffer, eluted with 0.4 ml 1.5 M NaCl, 20 mM Tris-HCl (pH 7.5), 2 mM EDTA and precipitated with ethanol as above. The DNA was incubated with $\gamma$-$^{32}$P-ATP (specific activity about 5000 Ci/mmole) and polynucleotide kinase, (A. M. Maxam and W. Gilbert, "A New Method For Sequencing DNA", *Proc. Natl. Acad. Sci. USA*, 74, pp. 560–564 (1977)) and purified by chromatography on a 3-ml Sephadex-G50 column in TNE. The eluted fractions were pooled and the $^{32}$P-DNA precipitated with ethanol as above; yield, about $10^7$ dpm.

The unlabeled PstI-cleaved Hif-4c DNA (90 μg) was mixed with 6x$10^5$ dpm of $^{32}$P-labeled PstI cleaved Hif-4c DNA from above and electrophoresed through a 10x20x0.7 cm, 2% horizontal agarose gel in 50 mM Tris-acetate buffer (pH 7.8) using a 2.5 cm slot. An x-ray film was exposed to the gel and the position of the 320-bp fragment determined. The gel strip containing the radioactive band (1.3x$10^5$ dpm) was cut out, crushed by pressing through a plastic 2-ml syringe and extracted overnight at 4° C. by agitation with ten times the gel vol of NET buffer. The DNA was adsorbed to a 0.1-ml hydroxy-apatite column (prewashed with 1 ml NET buffer). The column was washed with 1 ml 0.1 M K-phosphate buffer (pH 7.5) and the DNA eluted with 0.2 ml 1 M K-phosphate, buffer (pH 7.5). The eluate was diluted 10-fold with sterile distilled $H_2O$ and the DNA adsorbed to and eluted from DEAE and precipitated with ethanol as described above. This DNA is called "Hif-4c fragment".

The Hif-4c fragment (120 ng) was bound to DPT paper (0.5x0.5 cm) as described above. As a control, 120 ng β-globin cDNA fragment excised with HindIII from the hybrid plasmid Z-pBR322(H3)RcβG-4.13 (F. Meyer et al., "Transposition Of AT-linked, Cloned DNA From One Vector To Another", *Experimentia*, 35, p. 972 (1979); N. Mantei et al., supra) and processed similarly. Hybridization of duplicate filters to poly(A) RNA (in 20 μl)., washing of the filters and recovery of the RNA from the filters were asdescribed above. After injection into oocytes the following IZN-α activities were detected:

| DNA fragment | amount of leukocyte poly(A) RNA* (μg) | time of hybridi-zation | IFN-α activity (IU/ml)** (duplicate assay) |
|---|---|---|---|
| Hif-4c | 2.5 | 16 h | 250; 100 |
| β-globin cDNA | 2.5 | 16 h | 4; 1 |
| Hif-4c | 7.5 | 16 h | 3000; 1000 |
| β-globin cDNA | 7.5 | 16 h | 4; 30 |
| Hif-4c | 7.5 | 5 h | 1000; 1000 |
| β-globin cDNA | 7.5 | 5 h | 10; 1 |

*1 μg of this RNA gave 4600 IU/ml.
**Oocyte supernatant after 48 h incubation, assayed by cytopathic effect reduction (W. E. Stewart, II and S. E. Sulkin, supra).

Thus, Hif-4c contains an insert capable of hybridizing to IFN-αmRNA.

Figure 3A:
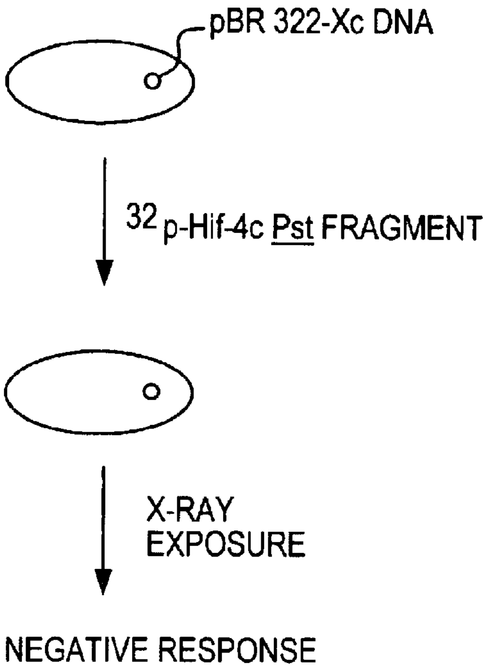
FIG. 3 is a schematic outline of one embodiment of a clone screening process using DNA sequences prepared in accordance with the invention.
Figure 3B:
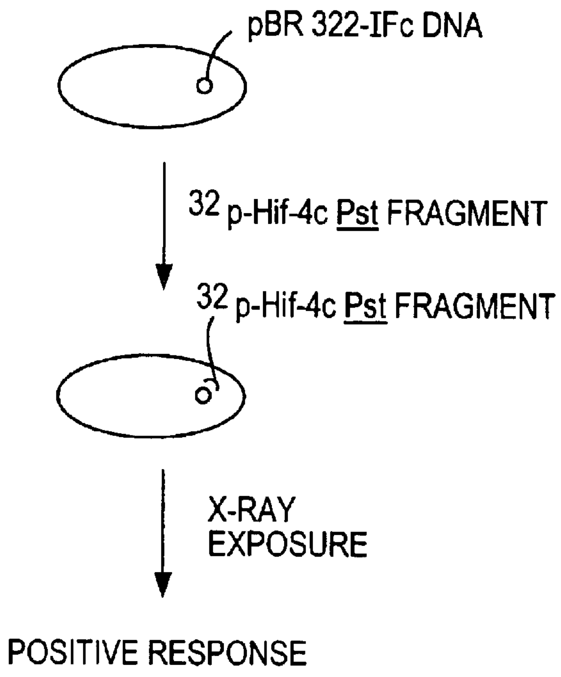

Identification of Clones of *E. COLI* Containing Recombinant DNA Molecules Cross-hybridizing to the Insert in Hif-4c Since the cDNA insert in recombinant DNA molecule Hif-4c was only about 320 b.p., or a third of the estimated size of IFN-αmRNA, the purified Hif-4c fragment described above was used as a probe to screen for bacterial clones containing recombinant DNA molecules having related hybrid DNA inserts (FIG. 3).

The 64 bacterial clones constituting subgroup λ-III described above were stamped onto a Millipore membrane (8 cm diameter), placed on an agar plate (supplemented with diaminopimelic acid, nalidixic acid and tetracycline, as above) and incubated for 24 h at 37° C. The filter was placed onto a 0.75 ml drop of 0.5 M NaOH and after 2–3 min transferred onto a paper towel to remove excess liquid; the step was repeated. The filter was neutralized, using 1 M Tris-HCl (pH 7.5), and washed with 1.5 M NaCl-0.5 M Tris-HCl (pH 7.4) in a similar fashion as above and air dried. The filter was dipped in. 0.3 M NaCl, air dried and heated at 80° C. for 2 h in a vacuum.

Hif-4c Pst fragment (30 ng) was $^{32}$P-labeled by nick translation (A. J. Jeffreys and R. A. Flavell, "The Rabbit β-Globin Gene Contains A Large Insert In The Coding Sequence", *Cell*, 12, pp. 1097–1108 (1977)) using β-$^{32}$P dATP and α-$^{32}$p dCTP (specific activity, 40 Ci/mmole each). The filter bearing the λ-III colonies was-prehybridized in 4×SET (SET is 0.15 M NaCl, 30 mM Tris-HCl (pH 8.0), 1 mM EDTA), 0.1% (w/v) Ficoll,-0.1% polyvinylpyrrolidline, 0.1% (w/v) BSA, 0.5% SDS, and 200 μg/ml denatured, fragmented salmon sperm DNA for 7 h at 68° C. and hybridized with 2×10$^5$ cpm of $^{32}$P-labeled Hif-4c fragment in 4×SET, 0.02% (w/v) Ficoll, 0.02% polyvinylpyrrolidine, 0.02% w/v BSA, 0.5% SDS and 200 μg/ml denatured salmon sperm DNA at 68° C. for 16 h. The filter was rinsed with SET-0.5% SDS at room temperature, washed with 2×SET-0.5% SDS for 5 h at 68° C., replacing the solution once, and with 3 mM Trizma base at room temperature for 4 h, replacing the solution once. After drying the filter, an x-ray film was exposed to the filter for 80 h using a screen. Three colonies gave a strong positive response, namely λ-III-7D, λ-III-2H and λ-III-4C, and 2 colonies a weak one, namely λ-III-1E, λ-III-3D.

Small cultures were prepared from the Hif-4c related clones, Form I DNA was purified, cleaved with PstI and analyzed by agarose gel electrophoresis as described above. All Form I DNAs gave rise to a large fragment (plasmid pBR322 moiety.) and a small one (hybrid insert). The recombinant DNA molecule from λ-III-2H released the largest insert, namely about 900 b.p. This recombinant DNA molecule was designated Z-pBR322(Pst)/HcIF-2H ("Hif-2H") and its insert "Hif-2H fragment".

Hif-2H was tested for its capacity to bind IFN-αmRNA by binding it to DPT paper (4 μg/100 mm$^2$) and hybridizing it to poly(A) RNA (0.3 μg/μl), all as described above, for 16 h and determining IFN-αmRNA activity:

| DNA sample | IFN-α activity (IU/ml)* |
|---|---|
| Hif-2H | 250 ± 50 (average of 4 determinations) |
| Z-pBR322 (H3)/RcβG-4.13 | 30 (average of 2 determinations) |
| pBR322 | 20 |

*Assayed by cytopathic effect reduction.

Hif-2H was recloned as described for Hif-4C and designated Hif-2h.

In a further experiment an additional set of *E. coli* clones containing recombinant DNA molecules was prepared and colonies hybridizing to the labeled Hif-4c fragment were identified. In order to ensure a high yield of plasmids with long cDNA inserts, part of the double-stranded $^{32}$P-labeled leukocyte cDNA prepared enzymatically from leukocyte poly(A) RNA. (the same cDNA preparation as described above) was fractionated by size by centrifuging through a sucrose density gradient, using the same procedure described for the centrifugation of the poly(A) RNA. The fractions containing the cDNA with a sedimentation velocity corresponding to a 600 b.p. DNA fragment or greater were pooled and the cDNA recovered after ethanol precipitation. The cDNA was elongated with dCMP residues, hybridized to dGMP-elongated Pst I-cleaved pBR322 and the hybrid DNA used to transform *E. coli* as before, except that *E. coli* EB101 was used. The bacteria were distributed onto B-cm diameter Millipore filters, placed on Tryptone medium agar plates (containing 10 μg/ml tetracycline) and grown until small colonies appeared. A replica filter was prepared by pressing a fresh, moist Millipore filter onto the colony-bearing filter, peeling it off, placing it face upward on an agar plate containing 4.4% glycerol and incubating it until small colonies appeared. This colony-bearing filter was covered with a further Millipore filter, frozen at −55° C. and stored (D. Hanahan and M. Meselson, "A Protocol For High Density Plasmid Screening", Sept. 1978, personal communication). Eighteen filters, bearing a total of about 5000 colonies were prepared. One replica of each filter was used for hybridization to the $^{32}$P-labeled, Pst I-excised Hif-4c DNA fragment, exactly as described above. About 185 positive colonies were identified on an autoradiogram, recloned on Millipore filters and identified once more by hybridization. 95 clones giving the strongest hybridization response were designated Z-pBR322(Pst)/HcIF-SN1 to SN95 and used for further investigation.

It is, of course, evident, given the ability of Hif-2h to produce a polypeptide displaying an immunological or biological activity of HuIFN (era), that Hif-2h and other DNA sequences related to it, e.g. Hif-4c, may be employed in this method of clone screening equally well on other clones containing DNA sequences arising from recombinant DNA technology, synthesis, natural sources or a combination thereof or clones containing DNA sequences related to any of the above DNA sequences by mutation, including single or multiple, base substitutions, insertions, inversions, or deletions to select other DNA sequences and clones which also code forHuIFN. Therefore, such DNA sequences and their identification also fall within this invention (e.g., infra). It is also to be understood that DNA sequences, which are not screened by the above DNA sequences, yet which as a result of their arrangement of nucleotides code on expression for the polypeptides coded for by the expression of the above DNA sequences also fall within this invention.

Further Characterization of Hif-2h DNA Insert

As described above recombinant DNA molecule Hif-2h contains an insert of about 900 b.p., and hybridizes to human leukocyte interferon mRNA. The following additional characteristics were determined.

1. Hybrid Arrested Translation

If mRNA is hybridized to a cloned, complementary cDNA, the translation of the mRNA is inhibited, however is heat denaturation of the hybrid releases translatable mRNA (B. M. Paterson et al., "Structural Gene Identification And Mapping By DNA-mRNA Hybrid-Arrested Cell-Free Translation", *Proc. Natl. Acad. Sci. USA*, 74, pp. 4370–74 (1977)). 2.2 μg Pst I-cleaved Hif-2h, and as a control 2 μg HindIII-cleaved Z-pBR322(H3)/RcβG-4.13 ("RcβG") were denatured in 10 μl 80% (vol/vol) deionized formamide −20 mM PIPES buffer (pH 6.4) for 10 min at 80° C. The solution was added to an Eppendorf tube into which leukocyte poly(A) RNA (5 μg), NaCl (4 μmoles) and EDTA (10 nmoles) had been dried down. The mixture was heated for 7 h at 48° C. under a layer of paraffin oil, cooled and diluted with 200 μl $H_2O$. The two samples were divided into equal parts, and one of each was heated at 100° C. for 30 sec. The nucleic acids were precipitated with ethanol, dissolved in 3 μl $H_2O$ and assayed for IFN-αmRNA activity in oocytes as above:

| DNA | Le poly(A) RNA input | Treatment | IFN-α (IU/ml)* |
|---|---|---|---|
| Hif-2h (1.1 μg) | 2.5 μg | hybridized | 400 |
| Hif-2h (1.1 μg) | 2.5 μg | hybridized and denatured | 2000 |
| RcβG (1 μg) | 2.5 μg | hybridized | 3000 |
| RcβG (1 μg) | 2.5 μg | hybridized and denatured | 3000 |
| Hif-2h (0.5 μg) | 1 μg | none | 2000 |
| — | 1 μg | none | 3000 |
| — | 1 μg | none | 2000 |

*The oocyte medium was assayed after 48 h by the cytopathic effect inhibition method.

Therefore, Hif-2h, when hybridized with poly(A) RNA, inhibited the translation of the IFN-αmRNA in the poly(A) RNA; after denaturing the hybrid, the IFN-αmRNA was again translatable. This experiment confirms that Hif-2h contains sequences complementary to IFN-αmRNA.

2. Analysis By Restriction Enzyme Cleavage And Determination of Nucleotide/Amino Acid Sequences and Restriction Map Digestions of Hif-2h with various restriction enzymes (New England Biolab) were carried out, and the resulting products analyzed by agarose gel electrophoresis. The underlined fragments are not common to pBR322 and Hif-2h:

| Restriction enzyme | Fragment sizes | |
|---|---|---|
| | Hif-2h** | pBR322*** |
| PstI | 885 ± 20, 4361 | 4361 |
| EcoRI | 1426, 3820 | 4361 |
| BglII | 5246 | not cleaved |

Figure 8:
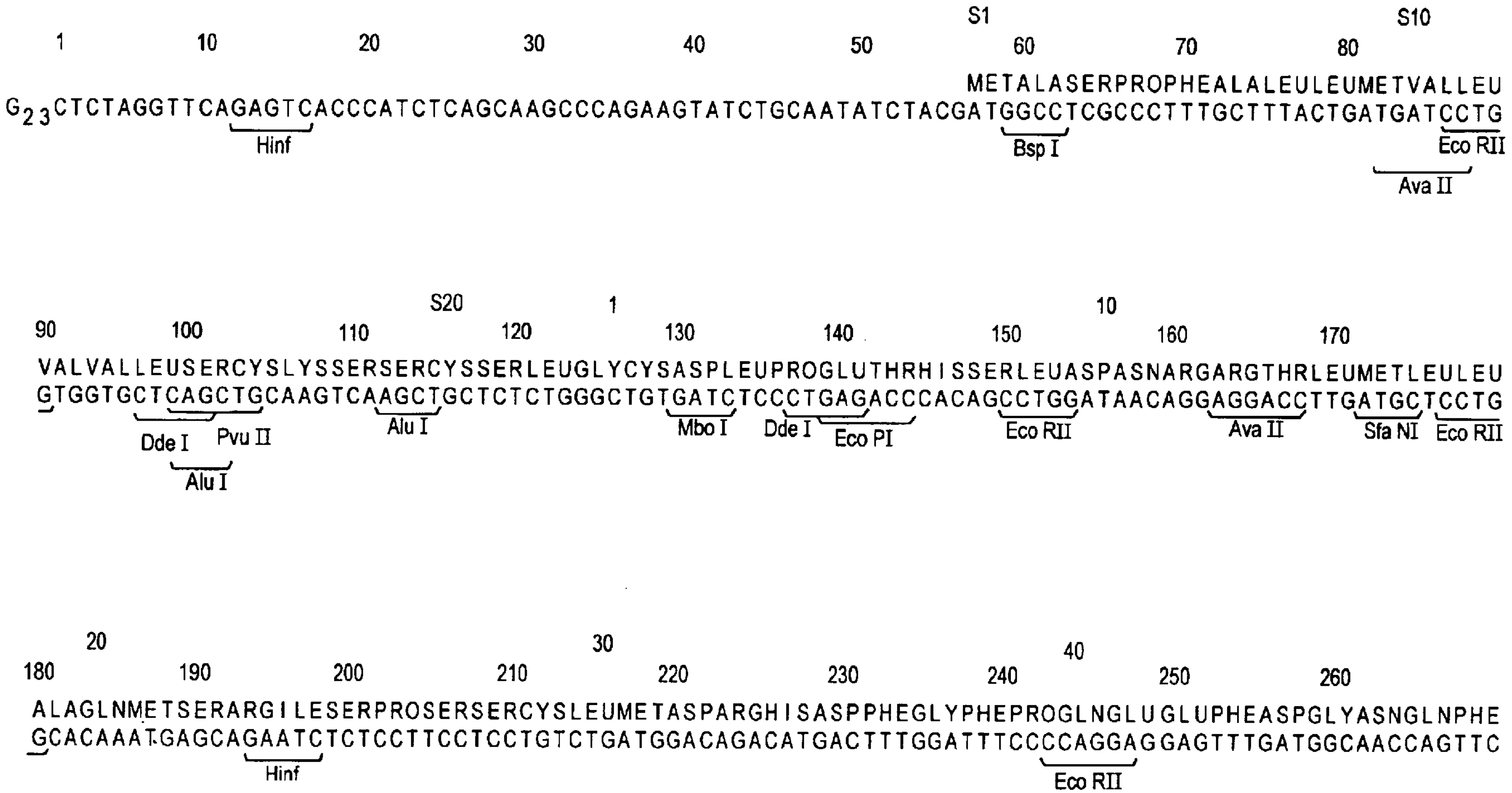

FIGS. 8–10 display the respective fragment sizes as determined by nucleotide sequence data.

| Restriction enzyme | Fragment sizes | |
|---|---|---|
| EcoRI + BglII | 336, 4960 | 4361 |
| EcoRI + PstI | 209, 676, 748 3611 | 748, 3611 |
| BspI | 921, 587, 540, 504, 457, 434, 2 × 231, +14 fragments 200 bp | 587, 540, 434, 267, 234 +14 fragments 200 bp |
| MboII | 1616, 884 and others | not done |

In addition, 5' terminally $^{32}$P-labeled PstI cleaved Hif-2h was cleaved with several restriction enzymes and the sizes of the radioactive fragments derived from the cDNA insert in that recombinant DNA molecule were determined:

| Restriction enzyme | $^{32}$P-fragments* |
|---|---|
| EcoRI | 676, 209 |
| HindIII | no cleavage |
| BspI | 799, 86 |
| HpaII | no cleavage |
| HhaI | no cleavage |
| BamHI | no cleavage |

-continued

| Restriction enzyme | $^{32}$P-fragments* |
|---|---|
| Hinf | 210, 62 |
| BglII | 545, 340 |

Figure 4:
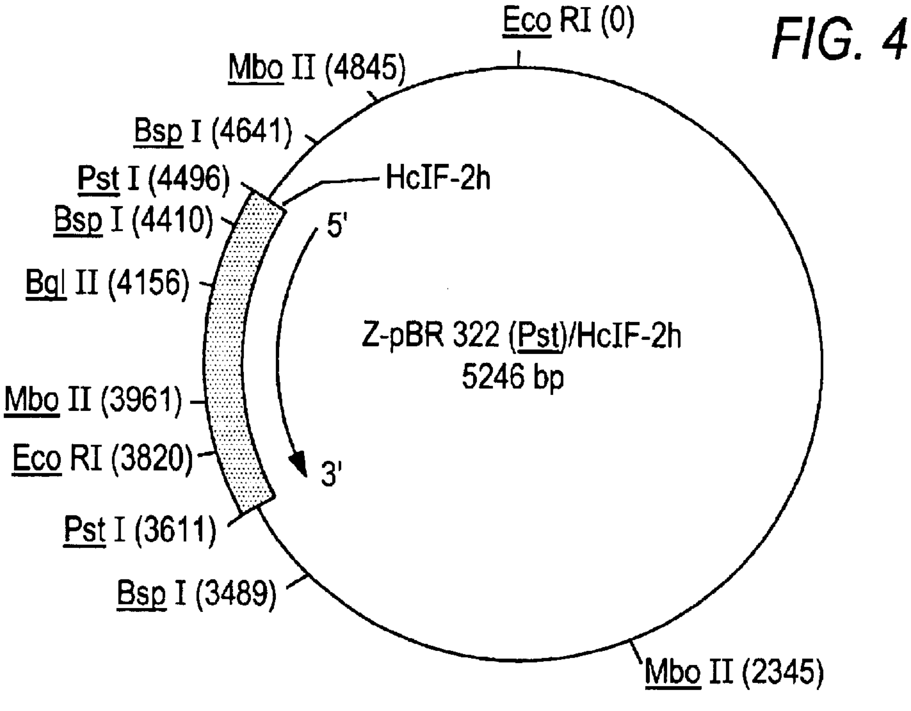
FIG. 4 is a restriction map of one of the clones of the invention, the positions of the restriction sites are based on fragment sizing by agarose gel electrophoresis.

The positions of the restriction sites in FIG. 4 are based on fragment sizing by agarose gel electrophoresis and may also be From these data a restriction map of Hif-2h was deduced (FIG. 4). Incomplete in regard to MboII sites within the insert. Only the sites closest to the insert are given within the pBR322 moiety. The arrow indicates the orientation of the IFN-αcDNA coding strand.

Although the actual structure of the Hif-2h fragment or other inserts in clones of this invention or the amino acid sequence or structure of the polypeptides coded therefrom is not required for one of skill in the art to make and use the invention described and claimed herein, the above data and restriction map were included in the original application hereto as the best available information on the structure of fragment at the time of filing the original application. Since that time, as expected (supra, p. 9, lines 27–29), these data and restriction map for the Hif-2h fragment have been refined using well-known techniques of nucleotide sequencing and restriction analysis. Eg., A. M. Maxam and W. Gilbert, 37 A New Method For Sequencing DNA", *Proc. Natl. Acad. Sci. USA*, 74, pp. 560–64 (1977). Plasmid DNA was prepared by Method B (N. M. Wilkie, et al., "Hybrid Plasmids Containing An Active Thymidine Kinase Gene Of Herpes Simplex Virus 1", Nucleic Acids Research, 7, pp. 859–77 (1979)) and restricted by various restriction enzymes essentially as recommended by the supplier, except that 2.00 μg/ml gelatin replaced the bovine serum albumin in the enzyme buffers. (EcoRI was a gift from W. Boll, BspI a gift from A. Kiss and other enzymes were obtained from New England Biolabs.)

Restricted DNA (20 μg) was extracted with phenol, precipitated with ethanol, dissolved in 0.05 M Tris-HCl (pH 8), and passed over a small column of Chelex-100. Fragments with flush or 5'-overhanging ends were dephosphorylated by treatment with 0.2 units calf intestinal alkaline phosphatase (Boehringer) per pmol DNA 5' ends in 200 μl 0.05 M Tris-HCl (pH 8) for 60 min at 37° C. The enzyme was inactivated by heating 60 min at 65° C. For DNA fragments with 3' overhanging ends, bacterial alkaline phosphatase (Worthington) was used as described (A. M. Maxam and W. Gilbert, supra) except that incubation was at 65° C. for 30 min. The dephosphorylated DNA was purified by adsorption to and elution from DEAE-cellulose (W. Muller et al., "Site-Directed Mutagenesis In DNA: Generation Of Point Mutations In Cloned B-Globin Complementary DNA At The Positions Corresponding To Amino Acids 121–123", *J. Mol. Biol.*, 124, pp. 343–58 (1978)) or subjected to polyacrylamide gel electrophoresis where required (see below). Fragments recovered from a polyacrylamide (or agarose) gel in 0.15 M Nacl, 0.05 M Tris-HCl (pH 8) were adsorbed to a 0.1-ml hydroxyapatite (Biorad HTP) column, washed 4 times with 1 ml 0.1 M potassium phosphate buffer (pH 7) and eluted with 0.3 ml 1 M potassium phosphate buffer (pH 7). The solution was diluted tenfold and the DNA adsorbed to DEAE cellulose and recovered as described (W. duller et al., supra).

After ethanol precipitation, the DNA was 5'-terminally labeled with [γ$^{32}$P] ATP (12–34 μCi per pmol DNA 5' ends) and polynucleotide kinase (New England Biolabs or P-L Biochemicals Inc.) essentially as described by A. M. Naxam and W. Gilbert, supra, except that the DNA was not denatured before the kinase reaction. Specific activities of 1–1.5 μCi [$^{32}$P] phosphate per pmol DNA 5' ends were obtained.

For sequencing, labeled fragments were cleaved with a second restriction enzyme and the products separated by electrophoresis through a 5% polyacrylamide gel in tris-borate-EDTA buffer. The desired fragments were extracted from the gel and purified (Muller et al., supra). The various fragments for sequencing were prepared as follows (the number indicates the nominal fragment chain length in base pairs, the labeled site is indicated by an asterisk):

(1) cleavage of Hif-2h with BspI, isolation of BspI-BspI-232 and BspI-BspI-949 by 5% polyacrylamide gel electrophoresis in Loening's buffer (U. E. Loening "The Fraction Of High Molecular weight Ribonucleic Acid By Polyacrylamide Gel Electrophoreses", *J. Biochem.* p. 102 (1967));

(2) cleavage of Hif-2h with BspI, labeling, cleavage with PstI, isolation of BspI*-PstI-83 and BglII*-PstI-570;

(3) cleavage of Hif-2h with BglII, labeling, cleavage with PstI, isolation of BglII*-PstI-336 and BglII*-PstI-570;

(4) cleavage of Hif-2h with MboII, labeling, digestion with PstI end HindII (to cleave an interfering 350 bp pBR322 fragment), isolation of MboII*-PstI-519 and MboII*-PstI-351;

(5) cleavage of Hif-2h with EcoRI, labeling, cleavage with PstI, isolation of EcoRI*-PstI-708 and EcoRI*-PstI-198;

(6) cleavage of Hif-2h with PstI, labeling, cleavage with BglII, isolation of PstI*-BglII-570 and PstI*-BglII-336;

(7) cleavage of Hif-2h with AvaII, labeling, cleavage with PstI and BglII, isolation of AvaII*-PstI-186 and AvaII*-BglII-147;

(8) cleavage of Hif-2h with PvuII, labeling, cleavage with PstI and BglII, isolation of PvuII*-PstI-486.

The fragments were degraded according to the method of A. M. Maxam and W. Gilbert, supra, with the modifications described in protocols provided by the same authors in September 1978. The products were fractionated on 0.1×25×36 cm 12% polyacrylamide gels (acrylamide/bisacrylamide=18/1) in 50 mM tris-borate, 1 mM EDTA (pH 8.3), with runs of 2, 8, 18 and 26 h at 900 V following a 6 h prerun at 700 V. Best results were obtained when the gels were kept at room temperature 2–3 days before use.

Each stretch of the cDNA insert was sequenced from both strands and each restriction site which served as labeled terminus was sequenced using a fragment spanning it. The nucleotide sequence thus obtained is depicted in FIGS. 8–10. As is to be expected the positions of the various restriction sites in this insert are more absolutely located than those determined by restriction enzyme cleavage alone and depicted in FIG. 4.

Referring now to FIGS. 8–10, the heteropolymeric part of the insert is flanked by 23G residues at the 5' end and by 7α residues (probably reflecting the poly(A) terminus of the mRNA) followed by 15C residues at the 3' terminus. For reference, the insert is numbered from the first nucleotide following the dG tail to the last nucleotide before the polyA residues. An ATG initiation triplet in position 57–59 and a TAA termination triplet at position 624–626 define a reading frame uninterrupted by nonsense codons. Both other reading frames in this region of the insert contain 18 and 12 nonsense codons respectively. Moreover, the only other sequences, i.e., in different reading frames, flanked by an ATG or GTG and a termination signal, which code for a polypeptide of 25 amino acids or more, are located between nucleotides 226 and 304, 640 and 778 and 683 and 743, respectively. Therefore, the region between nucleotides 57 and 626 most likely includes the nucleotide sequence of the Hif-2h fragment that codes for a polypeptide displaying a biological or immunological activity of IFN-α in accordance with this invention.

It should of course be understood that cloned cDNA from polyA RNA by the usual procedures (A. Efstratiadis et al., supra) lacks 5' terminal nucleotides and may even contain artifactual sequences (R. I. Richards et al., "Molecular Cloning And Sequence Analysis Of Adult Chicken B-Globin cDNA", *Nucleic Acids Research*, 7, pp. 1137–46 (1979)). Therefore, it is not certain that the ATG located at nucleotides 57–59 is in fact the first ATG of authentic mRNA. However, for the purposes of the following description, it is assumed that the ATG at nucleotides 57–59 is the first ATC of authentic mRNA.

By comparing the polypeptide coded by this region of the insert with that sequence of 35 amino terminal amino acids of authentic human lymphoblastoid interferon —SerAspLeuProGlnThrHisSerLeuGlyAsnArgArgAla LeuIleLeuLeuAlaGlnMetGlyArgIleSerLeuPheserCysLeu LysAspArgEisAsp—determined by K. C. Zoon et al., supra and M. Hunkapiller and L. Hood, sudra, it appears that the chosen reading frame is correct and that nucleotides 57–124 may code for a signal sequence which precedes the nucleotide sequence coding for the "mature" polypeptide because alignment of the published sequence with the determined sequence (from the 24th amino acid onward) displays extensive coincidence (i.e., 26 of 35 amino acids).

In eukaryotic mRNAs the first AUG triplet from the 5' terminus is usually the initiation site for protein synthesis (M. Kozak, "Now Do Eukaryotic Ribosomes Select Initiation Regions In Messenger RNA", Cell, 15, pp. 1109–25 (1978)). The codon in the Hif-2h fragment corresponding to the first amino acid of lymphoblastoid interferon is 22 codons from the first AUG (and 14 codons from the second one) indicating that the sequence coding for interferon may be preceded by a sequence determining a signal peptide of 23 (or less likely 15) amino acids. The longer of the presumptive signal sequences contains an uninterrupted series of 11 hydrophobic amino acids (and the shorter one, one of 6 hydrophobic amino acids). This accumulation of hydrophobic residues is characteristic of signal'sequences (cf., B. D. Davis and P. C. Tai, "The Mechanism Of Protein Secretion Across Membranes", *Nature*, 283, pp. 433–38 (1980))

The nucleotide sequence apparently corresponding to "mature" IFN-α polypeptide comprises 498 nucleotides, which code for 166 amino acids. Assuming that there is no carboxytermial processing, eolecular weight of the interferon polypeptide 19,388. The base composition of the coding sequence is 50% GC. The codon usage within the interferon coding sequence is in reasonable agreement with that compiled for mammalian mRNAs in general (R. Grantham, et al., "Codon Catalog Usage And The Genome Hypothesis", *Nucleic Acids Research*, 9, pp. 49–62 (1980)). Any deviations observed may be ascribed to the small numbers involved.

The structure of the polypeptide depicted in FIGS. 8–10 for the Hif-2h fragment, of course, does not take into account any modifications to the polypeptide caused by its interaction with in vivo enzymes, e.g., glycosolation. Therefore, it must be understood that this structure may not be identical with IFN-α produced in vivo, but it still has very similar, if not identical, biological and immunological properties. Neither, does this structure exclude the likelihood that other modifications such as mutations, including single or multiple, base substitutions, deletions, insertions, or inversions or chemical derivatizations of this structure will not produce compounds that also display IFN-α activity.

3. Determination of the Plus Strand of the Inserted IFN-αcDNA

Figure 5A:
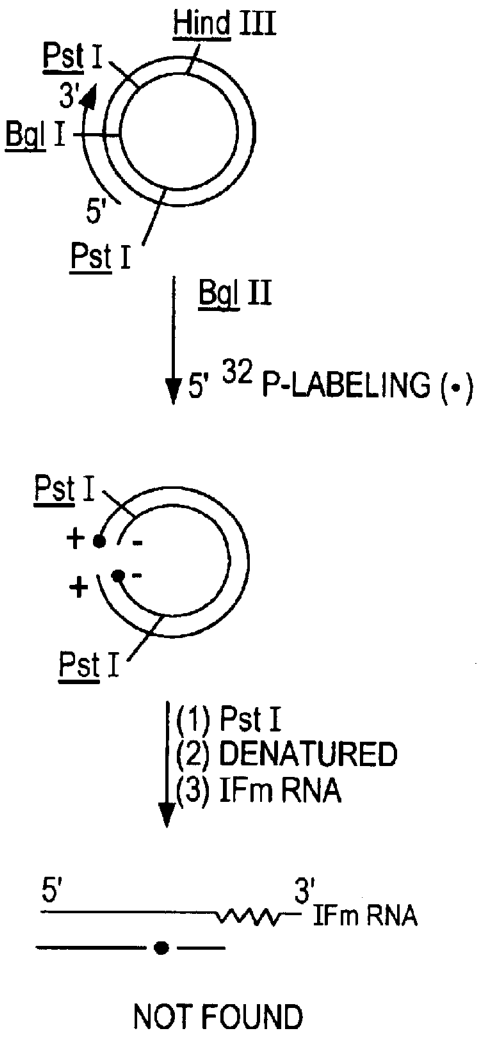
FIG. 5 is a schematic outline of the process of determining the orientation of a DNA insert in one recombinant DNA molecule of this invention.
Figure 5B:
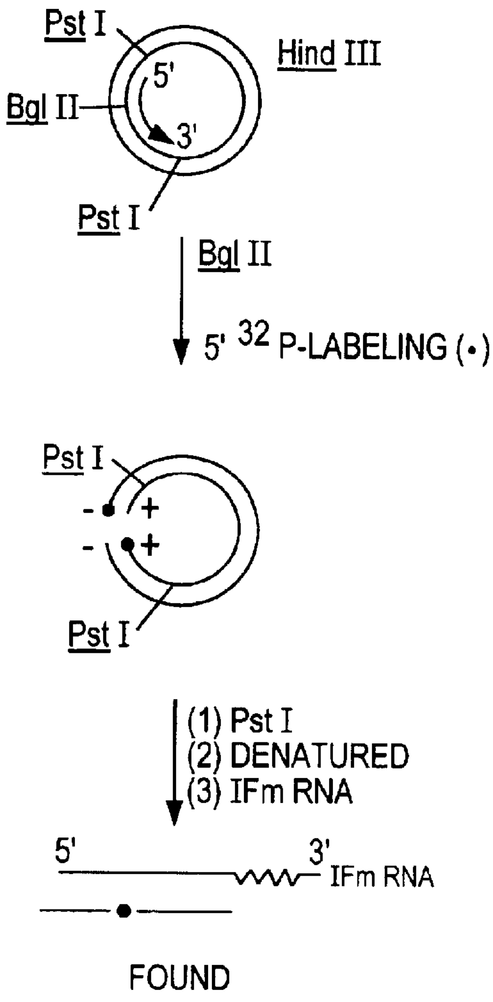

The DNA strand that has the same sequence as the mRNA is designated as plus strand, and its complement as minus strand. The plus strand of the IFN-αcDNA insert was identified as outlinedin FIG. 5 Hif-2h DNA was. cleaved with the restriction enzyme BglII, the termini labeled with $^{32}$P-phosphate (as described above for PstI-cleaved termini) and the DNA digested with PstI, to give longer (545 b.p. (570 b.p. as determined in the more refined analysis reported above)) and shorter 340 bp (336 bp as determined in the more refined analysis reported above)) radioactive fragments. These fragments were denatured and hybridized to poly(A) RNA from induced leukocytes in 80% formamide, 0.4 M NaCl, i.e., under conditions where DNA-DNA reassociation does not occur (supra). The nucleic acids were digested with nuclease S1, which degrades all single-stranded nucleic acids, in particular the non-hybridized $^{32}$P-DNA, and the products were separated on a polyacrylamide gel (R. F. weaver and C. Weissmann, "Mapping Of RNA By A Modification of The Berk-Sharp Procedure", *Nucleic Acid Research*, 7, pp. 1175–93 (1979)). An autoradiogram showed that only the shorter-nucleotide fragment had been hybridized and protected by the poly(A) RNA, identifying the 5'-labeled shorter-nucleotide strand as the minus strand. The orientation of the plus strand is therefore as given in FIG. 4 and FIG. 5 (right hand side).

4. Demonstration that Poly(A) RNA from Non-Induced Human Leukocytes does not Hybridize to Hif-2h DNA An experiment identical to that described in the preceding section was carried out, however the poly(A) RNA was from non-induced human leukocytes, prepared by the same procedure as in the case of Sendai virus-induced leukocytes. No detectable amount of labeled DNA was protected. By comparison to the results of the preceding section the poly(A) RNA from non-induced cells contains less than about 1/20 the amount of mRNA hybridizable to Hif-2h than does poly(A) RNA from induced cells.

Synthesis of a Polypeptide with Interferon Activity by *E. COLI* Containing Recombinant DNA Molecules Related to Z-PBR322(Pst)/HcIF-4c The PstI site of pBR322 lies within the β-lactamase (penicillinase) gene. Therefore, when a coding DNA segment (e.g., a cDNA comprising all or part of a gene) is ligated into the position in the proper orientation and proper reading frame, a fused protein may result. The protein would consist of the amino-terminal portion of β-lactamase followed by the amino acid sequence for which the inserted DNA sequence codes (L. Villa-Komaroff et al., supra). If the inserted DNA segment comprises a DNA sequence containing its own initiation signal, and has a sequence preceding it with a termination signal in phase with the β-lactamase sequence, termination and re-initiation may occur at the second initiation signal and a non-fused, active protein may result (A. C. Y. Chang et al., supra). To ensure that the DNA insert related to Hif-4c was inserted in the proper reading frame for expression within the β-lactamase gene, a set of derivatives of pBR322, namely pKT279, pKT280and pKT287 (constructed by K. Talmadge, personal communication, 1979) was employed. Each of these derivatives has a PstI site located such that a DNA insert ligated into that site will be in a different reading frame from an insert at the PstI site of the other derivatives of the set (FIG. 6). Therefore, the set permits the insertion of DNA into the β-lactamase gene in all three reading frames. The PstI-excised insert from Hif-2h was prepared as described for the fragment Hif-4c. The Hif-2h Pst fragment (10 ng) was mixed with PstI-cleaved pBR322, pKT279, pKT280 or pKT287 (10 ng in each case) in 20 μl of 10 mM Trig-HCl (pg 7.5), 6 mM $MgCl_2$, 100 mM NaCl, 6 mM β-mercaptoethanol, 200 μg/ml gelatin and 0.1 mM ATP and incubated with 0.1 units $T_4$ DNA ligase (New England Biolabs) for 16 h at 10° C. The resulting recombinant DNA molecules are designated Z-pBR322(Pst)/HcIF-2h, Z-pKT279(Pst)/HcIF-2h, Z-pKT280(Pst)/HcIF-2h and Z-pKT2B7(Pst)/HcIF-2h. *E. coli* EB101 was transformed with each of these recombinant DNA molecules and transformed colonies were selected on tetracycline-containing agar plates as described previously. Since tetracycline-resistant clones of transformed bacteria may also contain the recyclized vector, bacterial colonies of each set were grown on Millipore filters and colonies hybridizing to $^{32}$P-labeled Hif-4c fragment were identified and selected as described above. These strains were designated as follows,

*E. coli* HB101 (Z-pBR322(Pst)/HcIF-2h-AH1) to (-AH3);
*E. coli* HB101 (Z-pKT279(Pst)/HcIF-2h-AH1) to (-AH8);
*E. coli* HB101 (Z-pKT280(Pst)/HcIF-2h-AH1) to (-AH8);
*E. coli* HB101 (Z-pKT287(Pst)/HcIF-2h-AH1) to (-AH8).

Extracts of some of the above strains as well as of some of the strains Z-pBR322(Pst)/HcIF-SN1 to 95 were tested for IFN-α activity. Bacteria were grown in Tryptone medium to stationary phase, harvested, washed with 1/20 vol (based on the vol of the culture) 50 mM Tris-HCl (pH 8), 30 mM NaCl and frozen. After thawing, the cells were resuspended in the volume indicated below of the previous buffer and lysozyme was added to 1 mq/ml. After 60 min at 0° C. the suspensions were frozen (in an ethanol-dry ice bath) and thawed (at 37° C.) 5 times, and centrifuged 10 min at 12,000 rpm in a GSA Sorvall rotor. In some cases part of the supernatant (S30) was further centrifuged at 100,000×g in a Type 65 Spinco rotor and the supernata ts (S100) recovered. Such supernatants were screened for IFNα activity by the cytopathic effect reduction assay (Expt.1). The colonies showing a positive response in Expt. 1 were reassayed as well as 49 clones from the set Z-ptR322/HcIF-SN-1 to SN-95 described above at a lower dilution (Expt. 2).

| Source of extract: *E. coli* HB 101 transformed by: | Preparation | IFN-α activity (IU/ml) |
|---|---|---|
| Expt. 1* | | |
| Z-pBR322(Pst)/HcIF-2h | S30 | ? |
| Z-pBR322(Pst)/HcIF-2h-AH-1 to 3 | S30 | ? |
| Z-pKT279(Pst)/HcIF-2h-AH-1 to 7 | S30 | ? |
| Z-pKT279(Pst)/HcIF-2h-AH-8 | S30 | positive |
| Z-pKT280(Pst)/HcIF-2h-AH-2, 6, 7 | S30 | ? |
| Z-pKT280(Pst)/HcIF-2h-AH-1, 3, 4, 5 | S30 | positive |
| 2-pKT287(Pst)/HcIF-2h-AH-1, 2, 3, 4, 5, 8 | S30 | ? |
| Z-pKT287(Pst)/HcIF-2h-AH-6, 7 | S30 | positive |
| Expt. 2** | | |
| Z-pKT279/HcIF-2h-AH-8 | S30 and S100 | 300 |
| Z-pKT280/HcIF-2h-AH-1, 3, 4, 5 | S30 and S100 | 300 |
| Z-pKT287/HcIF-2h-AH-6 and 7 | S30 and S100 | 300 |
| Z-pBR322(Pst)/HcIF-SN-4, 5, 7, 9, 10, 11, 13, to 16 | S30 | neg (<10) |
| Z-pBR322(Pst)/HcIF-SN-18 to 22, 24, 25, 27, 30 to 34 | S30 | neg (<10) |

-continued

| Source of extract: E. coli HB 101 transformed by: | Preparation | IFN-α activity (IU/ml) |
|---|---|---|
| Z-pBR322(Pst)/HcIF-SN-38 to 41, 43 to 48 | S30 | neg (<10) |

*Expt. 1: Extracts assayed at 1:150 final dilution
**Expt. 2: Extracts assayed at 1:6 final dilution

| | | |
|---|---|---|
| Z-pBR322(Pst)/HcIF-SN-1 to 3, 6, 8, 12, 17, 23, 26 | S30 | 10 |
| Z-pBR322(Pst)/HcIF-SN-28, 29, 36, 37, 49 | S30 | 10 |
| Z-pBR322(Pst)/HcIF-SN-35, 42 | S30 | 200 |

Some of the more active producers from above were examined in more detail. Cultures were grown to late log phase (apparent $OD_{660}$ about 0.9)* and the cells lysed as above, in 1/50 of the culture volume. The following activities were found, using Z-pBR322(Pst)/HcIF-SN32 as a negative control:

* Three thousand liters or larger cultures of INF-α can be grown without loss of IFN activity.

| Source of extract: E. coli HB101 transformed by: | Preparation | IFNα activity** (IU/ml) (dup. assays) |
|---|---|---|
| Z-pKT279(Pst)/HcIF-2h-AH8 | S30, S100 | 100; 300 |
| Z-pKT280(Pst)/HcIF-2h-AH3 | S30, S100 | 1000; 1000 |
| Z-pKT287(Pst)/HcIF-2h-AH6 | S30, S100 | 200; 200 |
| Z-pBR322(Pst)/HcIF-SN35 | S30, S100 | 1000; 1000 |
| Z-pBR322(Pst)/HcIF-SN42 | S30, S100 | 300; 100 |
| Z-pBR322(Pst)/HcIF-SN32 | S30, S100 | 0; 0 |

**It is to be understood that the above reported expression may reflect interferon production by genes under the control of the penicillinase expression control sequence.

It is to be understood that the actual protein produced by these strains has not been analyzed structurally to determine whether or not it is produced fused to amino acids unrelated to IFN or with all or part of IFN's signal sequence. However, whatever protein is produced, it displays an immunological or biological activity of IFN. Therefore, the protein as expressed is useful. Most importantly, the activity of the protein demonstrates that the DNA sequence which codes for it is a DNA sequence related to HuIFN-α. It there is within the skill of the art to employ that DNA sequence as is demonstrated herein to select other like HuIFN-α related DNA sequences and to provide tie basis for other constructions that will express mature interferon or other variants thereof or will improve the yield of the particular protein expressed.

The level of production of a protein is governed by two major factors: the number of copies of its gene within the cell and the efficiency with which those gene copies are transcribed and translated. Efficiency of transcription and translation (which together comprise expression) is in turn dependent upon nudleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences' and fuse them instead to other known expression control sequences so as to favor higher levels of expression. This having been achieved, the newly engineered DNA fragment may be inserted into a multicopy plasmid or a bacteriophage derivative in order to increase the number of gene copies within the cell and thereby further to improve the yield of expressed protein.

Several expression control sequences may be employed as described above. These include the operator, promoter and ribosone binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phage λ ($O_LP_L$ and $O_RP_R{}^I$) the control region of the phage fd coat protein, or other sequences which control the expression of genes of prokaryotic or eukaryotic cells and their viruses. Therefore, to improve the production of a particular polypeptide in an appropriate host, the gene coding for that polypeptide may be prepared as before and removed from a recombinant DNA molecule containing it and reinserted into a recombinant DNA molecule closer to its former expression control sequence or under the control of one of the above expression control sequences. Such methods are known in the art.

Further increases in the cellular yield of the desired products depend upon an increase in the number of genes that can be utilized in the cell. This is achieved, for illustration purposes, by insertion of recombinant DNA molecules engineered in the way described previously into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al., "Lambdoid Phages That Simplify The Recovery Of In Vitro Recombinants", *Molec. gen. Genet.* 150, pp. 53–61 (1977) and N. E. Murray et al., "Molecular Cloning Of The DNA Ligase Gene From Bacteriophage T4", *J. Mol. Biol.*, 132, pp. 493–505 (1979)) and the recombinant DNA molecule produced by incubation with DNA ligase. The desired recombinant phage is then selected as before and used to lysogenise a host strain of *E. coli.*

Particularly useful A cloning vehicles contain a temperature-sensitive mutation in the repression gene cI and suppressible mutations in gene S, the product of which is necessary for lysis of the host cell, and gene E, the product which is the major capsid protein of the virus. With this system the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsidated it remains available for further transcrip- tion. Artificial lysis of the cells then releases the desired product in high yield.

In an initial attempt to increase the yield of polypeptide, displaying a biological or immunological activity of human leukocyte interferon, produced from hosts transformed with Z-pBR322(Pst)/HcIF-SN35 by the processes above described, a restriction map of the DNA insert in the hybrid was determined. This mapping revealed that as compared to Hif-2h, Hif-SN35 was lacking a PstI site flanking the 3' end of the sequence, part of the is signal sequence was missing (up to and including codon 7) and the AvaII site in the signal sequence had been replaced by a BspI site. Therefore, Hif-SN35 is likely a polymorphic or allelic varient of Hif-2h.

The plasmid Hif-SN35 was opened with PstI and the resulting DNA strand chewed back at both ends using standard procedures and the LAC-Alu fragment (infra) inserted therein and the plasmid reclosed. The actual structure of the modified plasmid, identified as Z-pBR322(Pst)/HcIF-SN35-AHL6, and the amino acid sequence at the amino terminal end of the protein produced in *E. coli* have been determined. The nucleotide sequence of this construction reveals that the LAC-Alu fragment was attached one amino acid away from the first amino acid of IFN-α1 (SN35). The amino acid sequence of the amino terminal portion of the protein expressed in *E. coli* revealed that a fused protein was produced having six amino acids fused to the IFN-α1 (SN35) sequence. However, hosts transformed with the modified plasmid produce about 100 times more polypeptide displaying a biological or immunological activity of human leukocyte interferon as compared to hosts transformed with unmodified Z-pBR322(Pst)/HcIF-SN35.

Figure 25:
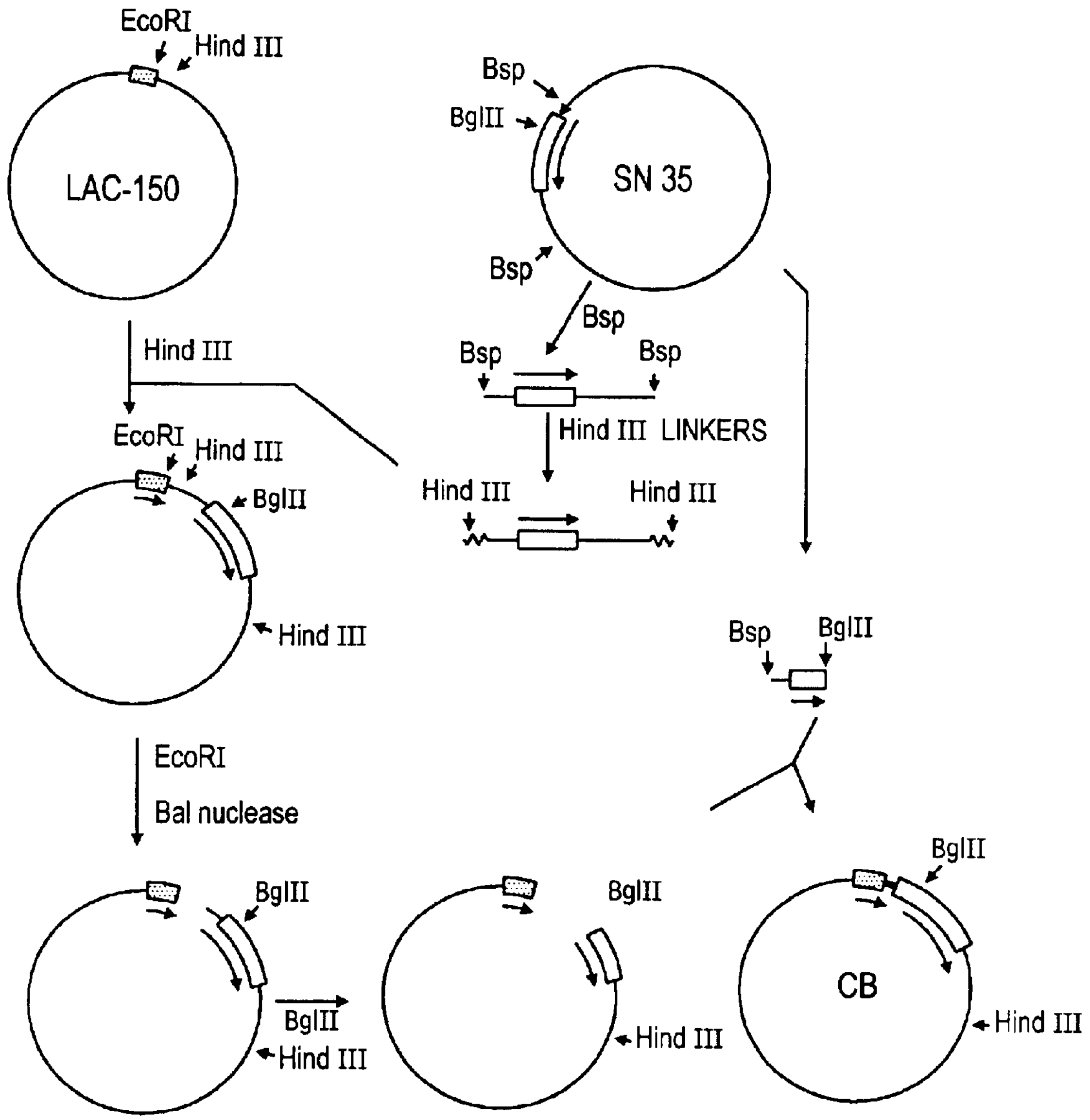
FIG. 25 is a schematic outline of the construction of plasmid C8-IFN-α1.

Referring now to FIG. 25, another attempt to improve the yield of polypeptide, displaying an immunological or biological activity of human leukocyte interferon, produced by hosts transformed with Z-pBR322(Pst)/HcIF-SN35 (SN35 in FIG. 25) is depicted. The hybrid plasmid was cleaved using standard procedures with BspI (a gift of Dr. Kiss). After heat inactivation (65° C., 30 min) of the restriction enzyme, the mixture was adjusted to 50 mM Tris-HCl (pH 8) and heated (37° C., 30 min). Following extraction with phenol and ether, the largest, α1cDNA fragment was isolated on low temperature gelling agarose (0.8%) and HindIII linkers attached. The modified fragment was then joined to Hinder-cleaved plasmid HS-pBR322(Eco)/lacUV5–150 ("LAC-150")* ( a gift of H. Schaller) by melting the fragment-containing gel pieces (about 20 μl each) at 65° C., cooling to 37° C. and adding 20U per μl T4 DNA ligase. After 16 h at 15° C., ligation occurred in the solidified gel (H. Lehrach, personal communication 1980). One tenth vol 100 mM Tris-Hcl (pH 7.5), 100 mM $CaCl_{2,\ 100}$ mM $MgCl_2$ were added to the sample and it was heated 5 min at 65° C. and cooled to 37° C. The samples were then used to transform $Ca^{+2}$ treated *E. coli* HB101, incubated at 0° C. for 20 min, heated at 42° C. for 1 min and for 10 min at 20° C. After addition of 1 mol tryptone medium, the samples were incubated 60 min at 37° C. and plated on to agar plates containing ampicillin. Plasmid DNA was separated from these cultures, as before, and the hybrid plasmid containing the IFN-α1 insert with its 5' end adjoining the LAC fragment identified by restriction analysis. The plasmid was then cleaved with EcoRI using conventional procedures and digested with exonuclease BAL-31 (0.06 U/ml, 2–4 min at 30° C.) to remove the over-hanging EcoRI tail of the LAC fragment and to shorten the β-galactosidase coding segment.

* This plasmid contains the lac promoter HaeII-202 bp fragment (W. Gilbert et al., "Lactose Operator Sequences And The Action Of Lac Repressor" in *Protein Ligand Interactions*, H. Sund and G. Blauer, eds. (Berlin, Walter de Gruyter), pp. 193–206 and K. Backman et al., "Maximizing Gene Expression On A Plasmid Using Recomrbnation In Vitro", *Cell*, 13, pp. 65–71 (1978)) flanked by an EcoRI linker at its 3' end.

To ensure that the treated plasmid contained the complete IFN-α1 coding sequence, the plasmid was then cleaved with BglII, using conventional procedures, worked up as before and the largest fragment separated on agarose gel (0.8%). This fragment was then combined with a BspI-BglII fragment from Z-pBR322(Pst)/HcIF-SN35 and the resulting hybrid plasmid used to transform *E. coli* HB101 as before. The transformed colonies were screened for IFN activity and one clone having a high level of IFN activity was selected. This clone was designated *E. coli* HB101 (C8-IFN-α1) and its hybrid plasmid C8-IFN-α1.

DNA sequence analysis of C8-IFN-α1 revealed that the coding sequence following the initiator triplet determined the first seven amino acids of β-galactosidase, a Pro residue generated by the fusion, amino acids 16 to 23 of the IFN-α1 signal sequence and the IFN-α1 (SN35) sequence. *E. coli* minicell strains (DS410)transformed with hybrid plasmid C8-IFN-α1 produce about 50 million units IFN per liter or about 2500 times more polypeptide displaying an immunological or biological activity of HuIFN as compared to minicells transformed with unmodified Z-pBR322(Pst)/Hif-SN35. Amino acid sequencing of the polypeptide produced by plasmid C8-IFN-α1 confirms that the product is a fused protein having seven amino acids from β-galactosidase, one amino acid generated from the fusion and amino acids 16–23 of the IFN-α1 signal sequence fused to IFN-α1.

Further, examples of various constructions to improve the protein yields in accordance with this invention are discussed in connection with other forms of 1FN-α (infra).

Properties of Interferon Activity Produced by *E. coli* Transformed with Hybrid Plasmids 1. sensitivity of IFN-α Activit to Trypsin 50 μl samples of authentic HuIFN-α (specific activity, $1.2\times10^6$ U/mg; 50U), and the S100 extracts described above of *E. coli* HB101 (Z-pKT287(Pst)/HcIF-2h-AH6) ("Hif-2B7-6 extracts") (200 U/ml, 10 U) and of *E. coli* HB101 (Z-pBR322(Pst)/HcIF-SN35) ("Hif-35 extracts") (1000 U/ml; 50 U) were incubated with various amounts of trypsin, as indicated below, for 30 min at 37° C. Since the S100 extracts have a high protein content, while the HuIFN-α does not, a mixture of HuIFN-α and the control S100 extract Hif-32 was tested in parallel:

| IFN-α preparation | Trypsin (μg) | IFN-α activity (units) |
|---|---|---|
| HuIFN-α (50 units in 50 μl | 0 | 50 |
| Hif-32 S100 extract) | 0.1 | 50 |
| | 1 | 50 |
| | 10 | 5 |
| | 50 | 0 |
| Hif-287-6 S100 extract (10 units) | 0 | 15 |
| | 0.1 | 15 |
| | 1 | 5 |
| | 10 | 1 |
| | 50 | 0 |

Therefore the IFN-α of the extracts is sensitive to trypsin and hence a protein.

| | | |
|---|---|---|
| Hif-35 S100 extract (50 units) | 0 | 30 |
| | 0.1 | 20 |
| | 1 | 20 |
| | 10 | 2 |
| | 50 | 0 |

2. Behavior on Chromatography on Sephadex G-100

Figure 7:
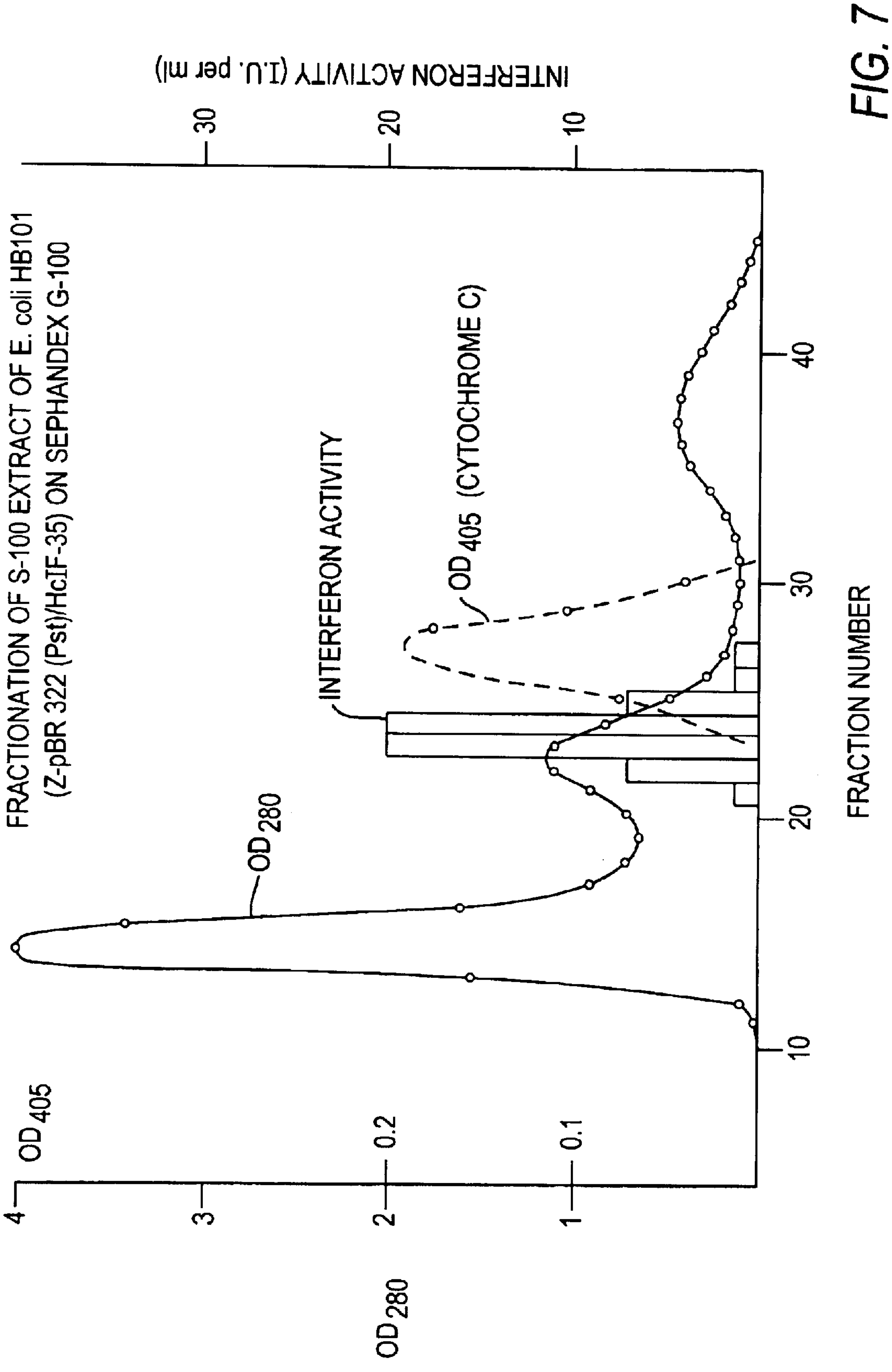
FIG. 7 displays the results of a Sephadex G-100 fractionation of supernatant prepared from a bacterial culture of this invention.

Extract Hif-35 (1lml) and the S100 extract of *E. coli* HB101 (Z-pBR322(Pst)/HcIF-SN32) ("Hif-32 extracts") were chromatographed on a 32-ml Sephadex G-100 column at 4° C. in 50mM K-phosphate buffer (pH.7.4). Cytochrome c (0.2 mg) was added as an internal marker. The flow rate was 2 ml/hr and 1.0 ml fractions were collected. The absorbance at 280 nm, and 405 nm (cytochrome c), and the IFN-α activity were determined. As shown in FIG. 7, the IFN-α activity of Hif-35 extracts was eluted before cytochrome c, with a $k_D$ value of about 0.45. Therefore, the apparent molecular weight of the substance was between about 20,000 and 30,000; no activity was detected in the fractions of control extract Hif-32.

* The molecular weight determined by nucleotide sequencing and assuming no carboxyterminal processing is 19,388.

3. Inhibition of the Interferon Activity of Hif-35 and Hif-287–6 by Antibody Against Euman Leukocyte Interferon.

HuIFN-α (specific activity $1.2. \times 10^6$ IU/mg), and the Hif-35/Hif-287–6 S100 extracts were incubated with various dilutions of sheep antiserum against HuIFN-α (prep. K. Cantrll, Feb. 24, 1976, specific activity 450, 000 units/ml) in 100 µl Modified Eagles Medium (MmM) with 10% calf serum for 30 min at 37° C. and 45 µl were assayed for IFN-α activity by the cytopathic effect reduction assay. (The antibody itself did not cause a cytopathic effect):

| IFN-α Preparation (units) | Anti-leukocyte-interferon antibody (units) | Residual IFN-α activity (IU) |
|---|---|---|
| IFN-α (10) | 0 | 5 |
| | 0.18 | –0.5 |
| | 9 | <0.1 |
| | 450 | <0.1 |
| Hif-35 extract (25) | 0 | 15 |
| | 0.18 | 15 |
| | 9 | <0.1 |
| | 450 | <0.1 |
| Hif-287-6 extract (25) | 0 | 15 |
| | 0.18 | 15 |
| | 9 | <0.1 |
| | 450 | <0.1 |
| none | 0 | <0.1 |
| | 450 | <0.1 |

To show that the action of the antibody was not due to an unspecific effect:, such as proteolytic degradation, a similar experiment was performed with the mouse interferon system:

| IFN Preparation (Units) | Anti-leukocyte-interferon antibody (units/ml) | IFN activity (units/ml) mouse system |
|---|---|---|
| mouse preparation (100 units) | 4500 | 100 |
| | 90 | 100 |
| | 18 | 100 |

Thus, antibodies directed against HuIFN-α specifically inhibit the IFN-α activity of polypeptides produced in *E. coli* transformed with certain recombinant DNA molecules containing the HcIF-2h DNA sequence. The apparently lower affinity of the antibody for the IFN-α produced in *E. coli* may reflect structural differences between the latter and natural HuIFN-α, for example, absence of carbohydrate moiety, presence of signal sequence, or fusion to part of the β-lactamase sequence.

4. Reduced Activity of Hif-35 and Hif-287–6 Extracts on Mouse Cells

Human CCL23 cells or Mouse L929 cells were treated with *E. coli* extracts, HuIFN-α (prep., K. Cantell, specific activity $1.2 \times 10^6$ units/mg) or mouse IF (N. I. H. standard), were challenged with virus (Mengo virus in the case of human cells and VSV in the case of mouse cells) and the IFN-α activity determined by the cytopathic effect reduction assay:

| | IFN activity (units/ml) | |
|---|---|---|
| Addition | human system | mouse system |
| mouse - interferon (120 units/ml) | — | 120 |
| Hif-35 extracts | 100 | 13 |
| | 1000 | 120 |
| Hif-287-6 extracts | 30 | 4 |
| | 300 | 40 |
| HuIFN-α (100 units/ml) | 100 | 4 |
| HuIFN-α (1000 units/ml) | 1000 | 40 |

These results show that Hif-35 and Hif-287–6 extracts have a protective action on human cells and only a slight effect (~10%) on mouse cells, as is typical for human interferon.

5. Effect on Some Cell Function

Extracts from *E. coli* Hl101 (Z-pBR322(Pst)/Hif-SN35-ARL6) were compared with authentic IFN for its effect on some cell functions. The *E. coli* made INF-αdisplayed the following properties of natural INF-α: (1) it enhances natural killing activity of human lymphocytes; (2) it enhances antibody-dependent cell-mediated cytotoxicity; (3) it suppresses antigen- and mitogen-induced leukocyte migration inhibition; and (4) it inhibits growth of IFN-sensitive Burkitt lymphoma cells. These properties are indicia of *E. coli* synthesized IFN-α1's activity against human tumors and cancers.

6. Activity of IFN-α without Amino-terminal Sequences

IFN-α without amino-terminal sequences has also been made in *E. coli* and shown to display activity consistent with IFN activity.

To construct the appropriate recombinant DNA molecule, plasmid Hif-2h (supra) was partially digested with EcoRI and BamHI and the fragment containing the ZEN-α1 coding sequence separated on agarose gel and Combined with the non-IFN-α1 coding sequence obtained from an EcoRI/BamHI restriction of plasmid Hif-SN35 which is missing a PstI site adjacent the 3' end of the hybrid insert as compared to Hif-2h (supra). The resulting plasmid was then restricted with PstI/BglII to remove a portion of the amino terminal part of the IFN-α1 coding sequence. Inserted in its place were a series of IFN-α1 fragments prepared by digestion of plasmid Hif-2h with PvuII, treatment with Bal exonuclease, attachment of PstI linkers and restriction with BglII. The resulting plasmids thus contained a series of IFN-α1 coding sequences which lacked various portions of their amino terminal sequences. One of these (plasmid 2H-M8) was digested with PstI and its nucleotide sequence determined sequencing revealed that the plasmid 2H-M8 contained several nucleotides between the Pst site and the first codon (CYS) of IFNα1. Therefore, the PstI digested plasmid 2H-M8 was treated with T4 polynuclease/dATP, S1 exonuclease and digested with SalI. This procedure generated a series of fragments whose IFN-α1 coding sequences were missing portions of their amino terminal end. These fragments were then placed under LAC control by operatively linking them to a GUA-LACfragment prepared fromplasmid Lac3VS by digestion with EcoRI, treatment with exonuclease SI and digestion with SalI. The resulting series of plasmids thus had IFN-α1 coding sequences lacking various portions of their amino terminal ends attached in a counterclockwise direction via an AUG to a fragment containing the LAC promoter.

Some of these plasmids were sequenced. One began at the fifth amino acid of IFN-α1 and one at the tenth amino acid of IFN-α1. In *E. coli* minicells (DS410) both of these plasmids produced polypeptides that displayed IFN activity. Therefore, not all of the IFN-α1 protein is required for IFN activity.

Identification of Clones of *E. COLI* Containing Recombinant DNA Molecules Whose DNA Inserts Weskly Cross-hybridize to the Insert in Hif-4c and have a Different Restriction Map than the Hif-2h Fragment The comparison of the first 35 amino acids of authentic lymphoblastoid interferon (Zoon et al., sudra, and M. Hunkapiller and L. Hood, supra) and the sequence deduced from Hif-2h fragment shows 9 differences. In all cases, the codons for the differing amino acids could be related by one-base changes. The amino acid compositions determined directly for authentic lymphoblastoid interferon on the one hand and deduced from the sequence of the Hif-2h fragment on the other, also show striking differences in regard to their content of Gly, Pro, Cys and Met. These differences are too large to be explained by polymorphism. Instead, they most likely reflect the existence of at least two non-allelic genes, because the degree of divergence of the two proteins (26% mismatch) is similar to that between, for example, human and sheep B-globin (23% mismatch). Accordingly, the clones that displayed weak hybridization to fragment Hif-4c, identified previously (supra), were examined and a clone *E.coli* HB101 (Z-pBR322(Pst)/HcIF-II-206) was identified.

Figures 11A, 11B:
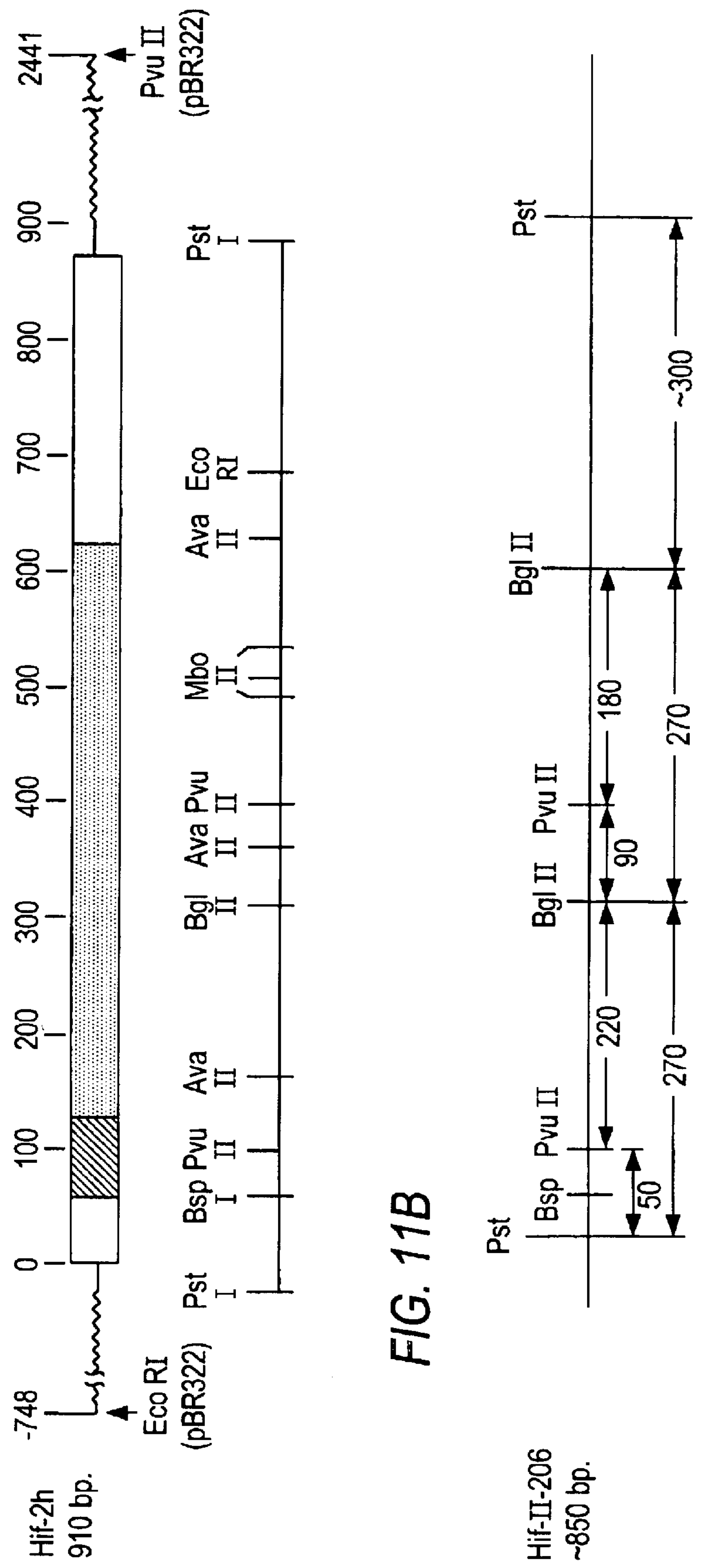
FIG. 11 is a schematic comparison of the restriction maps of two DNA inserts of recombinant DNA molecules of this invention.

The hybrid plasmid Z-pBR322(Pst)/HcIF-II-206 ("HcIF7II-206") of this clone and its DNA insert "Hif-II-206 fragment" are weakly hybridizing to Hif-4c and Hif-2h fragment. *E. coli* transformed with plasmid Hif-II-206 produces polypeptides displaying a biological or immunological activity of HuIFN-α. Hif-II–206 fragment has a restriction map that is distinct from that determined for the Hif-2h fragment. A comparison of the two restriction maps is set forth in FIG. 11. Again, the absolute location of the restriction sites in the Hif-II-206 fragment is not determined by restriction mapping alone. However, sequencing of the nucleotide sequence of this insert, using the standard procedure described above, permits more absolute determination of these locations. However, because of the differences in the restriction map of the Hif-II-206 fragment as compared to the Hif-2h fragment, it is clear that the interferon genes of the two inserts have different nucleotide sequences.

Referring now to FIGS. 12–16, the nucleotide sequences of the inserted DNA sequence—Hif-II-206 fragment—of culture HcIF-G and the inserted DNA sequence—Hif-2h fragment—of culture HcIF-E (infra), determined previously, and the corresponding amino acid sequences of the proteins coded for by those nucleotide sequences are displayed. The nucleotide sequence of the Hif-II-206 fragment—the Pst I fragment (790 bp) of the plasmid DNA isolated using the procedure of Method B as described by N. M. Wilkie et al., *Nucl. Acids Res.*, 7, pp. 859–77 (1979) from culture HcIF-G—was determined using the standard procedure of A. M. Maxam and W. Gilbert, supra. The sequencing strategy employed is shown in FIG. 17.

Restricted DNA (usually about 10 μg) was 5' terminally labelled as described by N. Mantei et al., *Gene*, 10, pp. 1–10 (1980). Labeled fragments were cleaved with a second restriction enzyme, the products separated by electrophoresis through a 5% polyacrylamide gel in Tris-borate-EDTA buffer (A. C. Peacock and C. w. Dingman, *Bioch.*, 6, pp. 1818–27 (1967)), extracted from the gel, and purified as described by w. Muller et.al., *J. Mol. Biol.*, 124, pp. 343–58 (1978).

Figure 17:
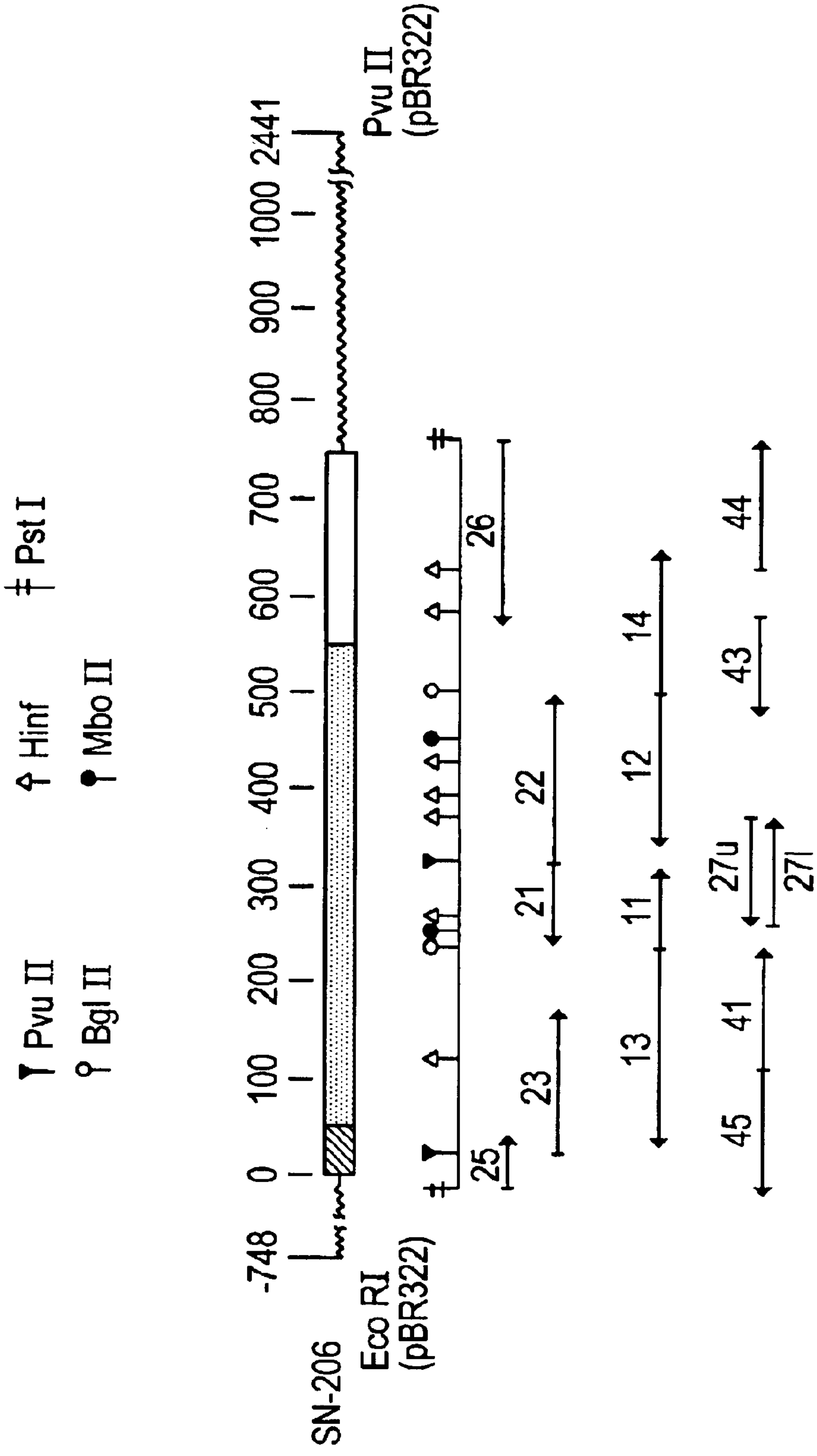
FIG. 17 displays a partial restriction map of Z-pBR322 (Pst)/HcIF-II-206 and the sequencing strategy employed to determine the nucleotide sequence of the Hif-II-206 fragment displayed in FIGS. 12–16.

Referring now to FIG. 17, the various fragments for sequencing were prepared as follows:

25 and 26 —cleavage of Hif-II-206 with PstI, labelling, cleavage with BglII, isolation of a PstI*-BglII fragment (257 bp) ("25") and a PstI*-BglII fragment (279 bp) ("26");

21, 22 and 23—cleavage of Kif-II-206 with PvuII, labelling, cleavage with BglII, isolation of a PvuII*-BglII fragment (88 bp) ("21"), a PvuII*-BglII fragment (176 bp) ("22") and a PvuII*-BglII fragment (214 bp) ("23");

11, 12, 13, and 14—cleavage of Hif-II-206 with BglII, labelling, cleavage with PstI, isolation of a BglII*-PstI fragment (279 bp) ("14") and a comigrating mixture of a BglII*-PstI fragment and a BglII*-BglII* fragment. Cleavage of the mixture with PvuII and isolation of a BglII*-PstI fragment (257 bp) ("13"), a BglII*-PvuII fragment (176 bp) ("12") and a BglII*-PvuII fragment (88 bp) ("11").

27L, 27U, 41, 43, 44 and 45—cleavage of Hif-II-206 with HinfI, labelling, isolation of precursor fragments: Hinfl*-HinfI*.(113 bp) ("27P"), HinfI*-HinfI* (146 bpl ("128P"), HinfI*-Hinfl* (159 bp) ("30P"), Hinfl*-Hinfl* (397 bp) ("31P") and HinfI*-HinfI* (1522 bp) ("132P"). Cleavage of 28P with Mboll and isolation of a fragment Hinfl*-MboII (112 bp) ("41"). Cleavage of 30P with Mboll and isolation of a fragment Hinfl*-MboII (126 bp) ("43"). Cleavage of 31P with PstI and isolation of a fragment HinfI*-PstI (llbp) ("44"). Cleavage of 32P with PstI and isolation of a fragment HinfI*-PstI (139 bp) ("45"). Strand separation of 27P to yield two strands ("127U" and "27L").

All segments, except 27U and 27L, were sequenced on both strands and across the restriction sites that served as orgins for sequencing, except for the BglII site at position 185.

From a comparison of the amino acid sequence coded for by the two inserts it is apparent that the Hif-II-206 fragment codes for an interferon-like protein having one less amino acid than does the Hif-2h fragment (amino acid 44 (Asp) present in Hif-2h is missing in Hif-II-206). Moreover, 10% of the nucleotide positions and 17% of the derived amino acid residues of the two fragments are different.

In addition, when compared to the 35 amino acids determined for the amino terminus of lymphoblastoid interferon (K. C. Zoon et al., *Science*, 207, pp. 527–28 (1980)), the insert Hif-II-206 codes for a protein that differs in 5 residues from the 35 amino acid residues determined by Zoon et al., supra. Therefore, at least three different IFN genes of the leukocyte type (a type) must exist—Hif-2h fragment, Hif-II-206 fragment and the gene coating for Zoon's IFN. In accordance with the newly proposed nomenclature for interferon, hereinafter the proteins coded for by these genes will be identified as follows:

| IFN Gene Source | Protein |
|---|---|
| Hif-2h | IFN-α1 |
| Hif-II-206 | IFN-α2 |
| IFN from lymphoblastoid cells (Zoon et al. (supra) | IFN-α3 |

The differences between IFN-α1 and IFN-α2 are also reflected in their varying activities on human CCL23 and bovine embryonic kidney (BEK) cells:

| | Relative IFN Activity* | | |
|---|---|---|---|
| Extract | CCL23 | BEK | Ratio |
| Hif-II-206 (IFN-α2) | 1.7 | 1.0 | 1.7:1 |
| Hif-SN35** (IFN-α1) | 0.05 | 1.0 | 1:20 |

**E. coli* HB101 containing the hybrid plasmid were grown in tryptone medium with shaking to an $OD_{650}$ of about 1–2. The cells were harvested, weighted, resuspended in 1/100 or 1/20 of the original cultrue volume and lysed by the lysozyme-freeze-thaw method (S. Nagate et al., Nature, 284, pp. 316–20 (1980)). The S-30 supernatants were tested by CPE reduction assay in microtiter plates. Extracts from control cells were negative (<1 I.U./ml). Human CCl23 cells and bovine embryonic kidney (BEK) cells (FLOW) were grown in MEM-10% fetal calf serum. Exposure to IFN-containing extracts was for 24 h. The cells were challenged with an appropriate dilution of Mengo virus and stained 24 h later. Values were estimated visually relative to partially purified leukocyte IFN (preparation PIF, a gift of K. Cantell) of known titer. This preparation was about 3× more active on human than on bovine cells.
**The comparison of the restriction maps of Hif-SN35 and Hif-2h suggest that they are polymorphic variants of each other (supra).

Therefore, IFN-α1 is about 30 times less active on human cells than IFN-α2. Yet, they are both about equally active on bovine cells. Therefore, IFNs may, in addition to -their use as antiviral and antitumor or anticancer agents in humans, also be useful in treating these conditions in cattle. For example, preparations of HuIFN-α could be employed in a standard manner (supra) in treating FMDV and other well known viral infections of cattle. This is even more particularly true for IFN-α1 since its activity on bovine cells is about 20 times greater than its activity on human cells.

Because of the improved yield attained in the case of IFN-α1 with construction C8 (supra), a similar construction was made for IFN-α2. Z-pBR322(Pst)/Hif-II-206 was cleaved completely with BspI and partially with PvuII (at P1) (FIG. 28) and the 867 bp fragment was isolated from a 6% polyacrylamide gel. This fragment was then ligated to a 2590 bp PvuII fragment of C8-IFN-α1.* The resulting hybrid plasmid was used to transform *E. coli* HB101 and the clones screened for IFN activity. One clone displaying a high activity was selected and designated *E. coli* EB101 (C8-IFN-a2).

Figure 28:
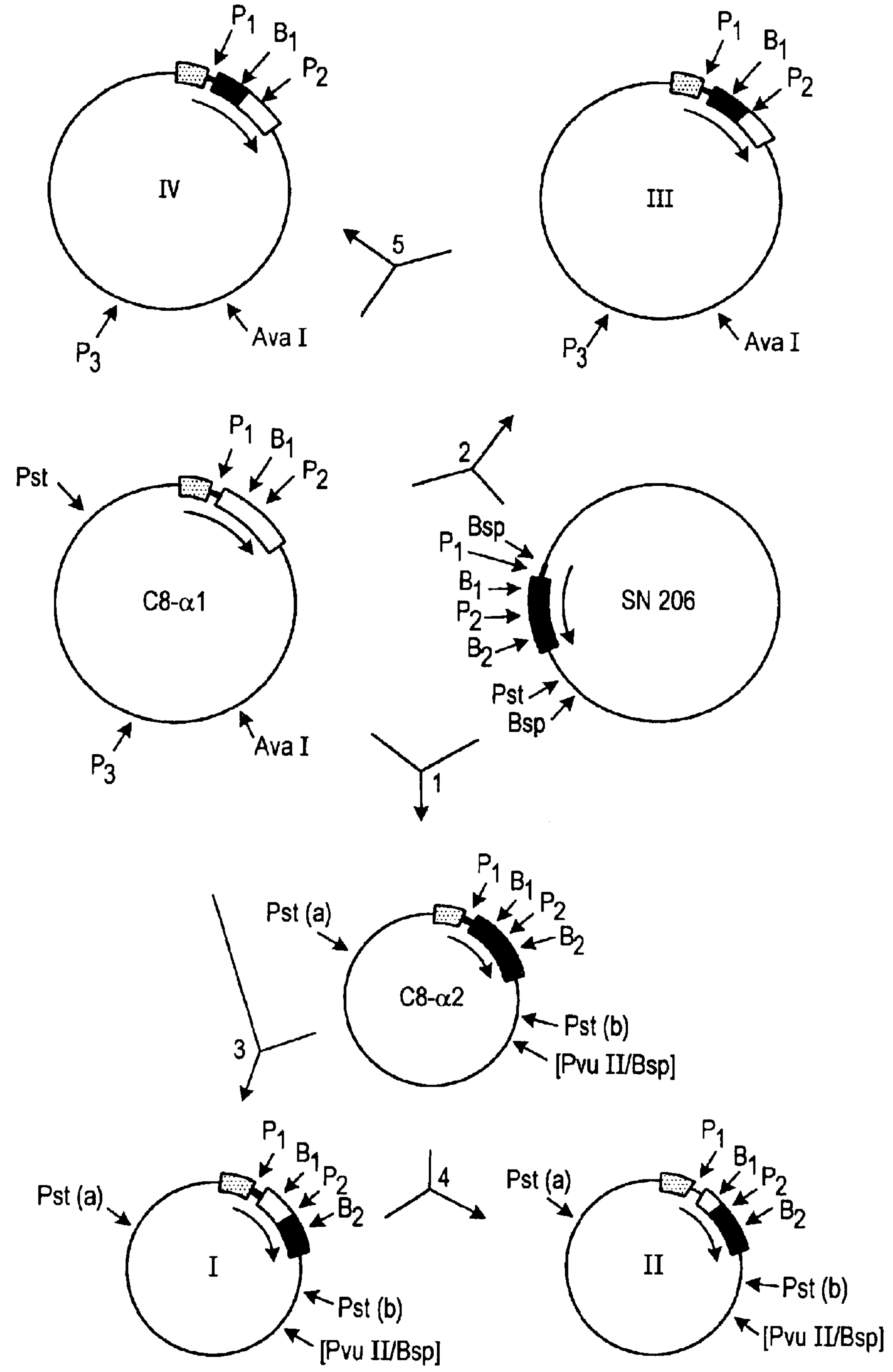
FIG. 28 is a schematic outline of the construction of plasmid CB-IFN-α2 and the hybrid molecules I, II, III and IV.

* C8-IFN-α1 has three PvuII restriction sites (FIG. 28). The 2590 bp fragment is between $P_1$ and $P_3$.

DNA sequencing of hybrid plasmid C8-IFN-α2 revealed that it like C8-IFN-α1 had a coding sequence following the initiator triplet that determined the first seven amino acids of β-galactosidase, a Pro residue generated by the fusion and amino acids 16 to 23 of the IFN-α2 signal sequence. Therefore, again a fused protein containing IFN-α2 is likely to be expressed.

Minicells transformed with this plasmid gave 100–200 million units per 1 of IFN or 20000 to 40000 times higher yields of IFN-α2 than minicells transformed with unmodified Z-pBR322(Pst)/Sif-II-206.

A comparison of the relative yields of C8-IFN-α1 (~50×$10^6$ units/liter) and C8-IFN-α2 (~100–200 million units per liter) is at first surprising because IFN-α2 has been shown to be about 30 times more active than IFN-α1 on human cells (supra). However, quantitative analysis of the amount of the two proteins made by minicells transformed with the two C8 plasmids revealed that in C8-IFN-α1 about 5 to 6 times more protein than in C8-IFN-α2 was being made. Therefore, the yields measured on the basis of IFN activity had been skewed by the much greater amount of protein made in the case of C8-IFN-α1.

Figure 26:
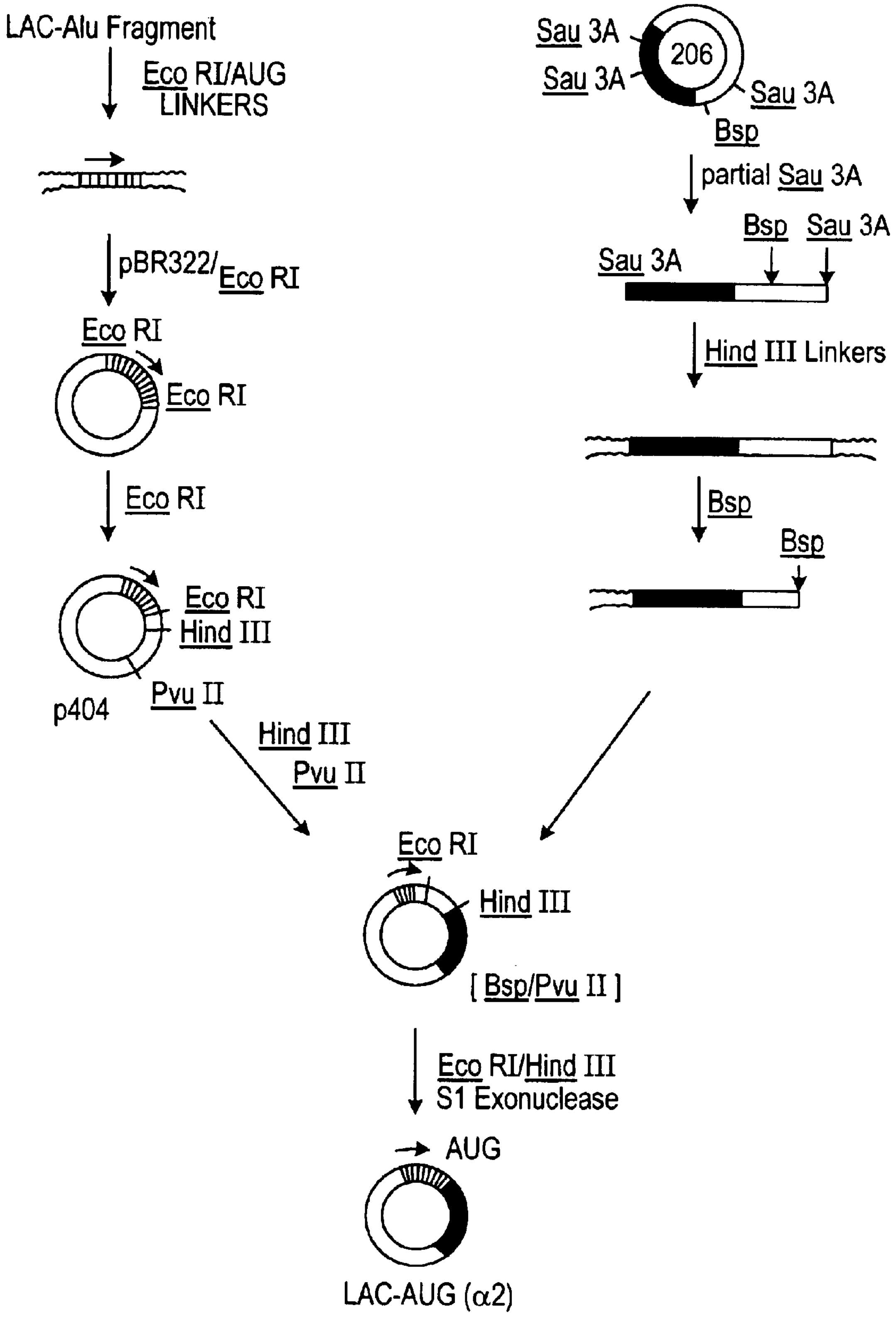
FIG. 26 is a schematic outline of the construction of plasmid LAC-AUG(α2).
Figure 27:
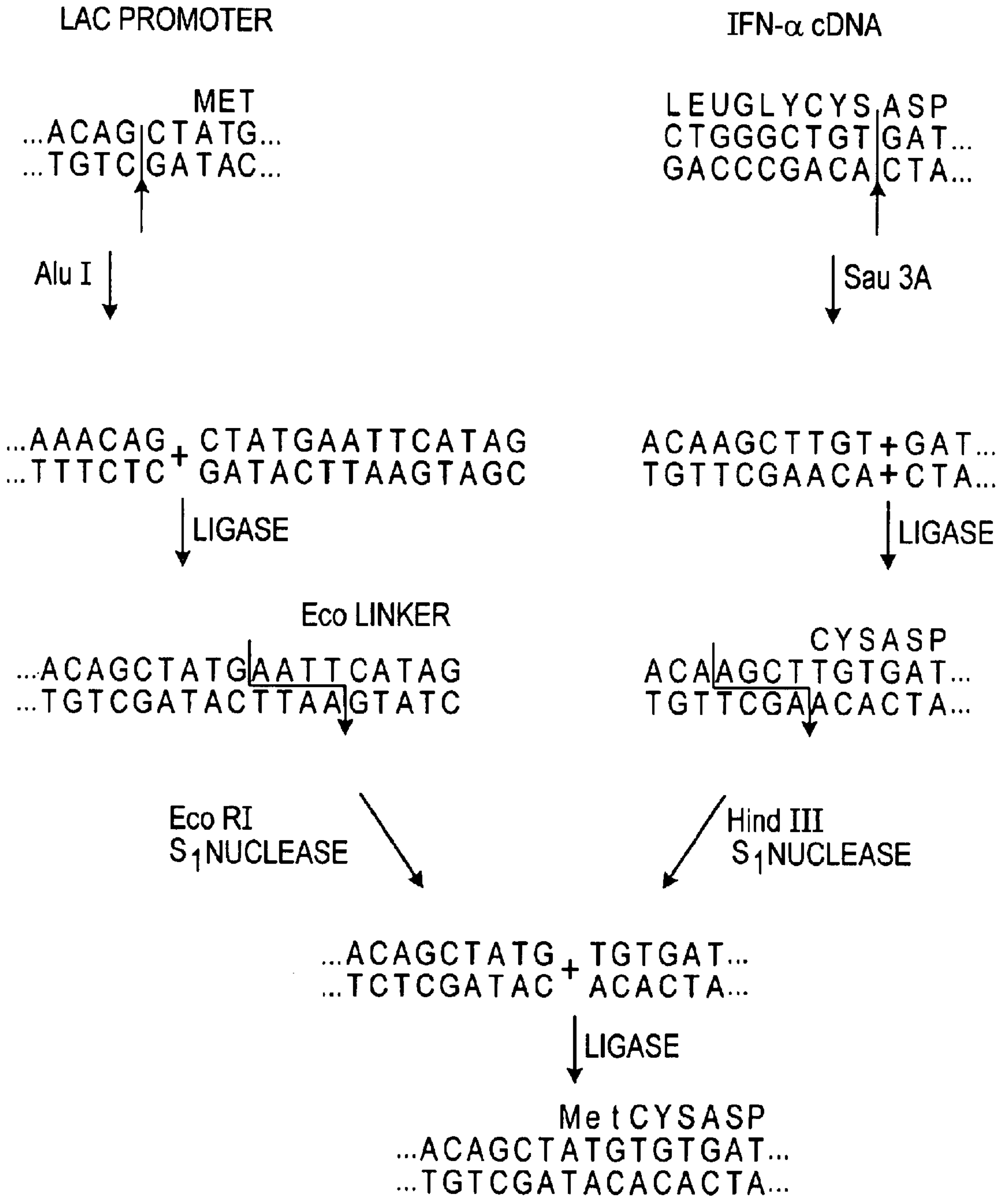
FIG. 27 displays the reconstruction of the AUG initiation codon and the CYS initial codon in the construction of LAC-AUG(α2).

Referring now to FIG. 26, another construction in an attempt to improve the yield of IFN-α2 is described. First, an expression plasmid containing the LAC Alu fragment was prepared by restricting the known lac promoter with AluI and extending the fragment as shown (for one termini) in FIG. 27 with EcoRI linkers (prepared by collaborative research). The extended fragment was then inserted into pBR322 at the EcoRI site and a small EcoRI-EcoRI fragment deleted from the construction. The resulting plasmid, designated 404 in FIG. 26 was cleaved with HindIII and PvuII for insertion of the ItN-α2 containing fragment. That IFN-α2 fragment was prepared by partial Sau3A restriction of Z-pBR322(Pst)/HcIF-II-206 ("206" in FIG. 26), extension of the Sau3A fragment with HindIII linkers (FIG. 27) and cleavage with BspI. After insertion of this fragment into the SindIII-PvuII cleaved plasmid 404, the resulting plasmid was restricted with HindIII and EcoRI, treated with sl nuclease to bring the LACpromoter closer to the IFN-α2 gene and religated. This construction identified as plasmid LAC-AUG(α2) has the IFN-α2 DNA sequence under the control of the LAC promoter. Moreover, the IFN-α2 sequence immediately follows the initiating AUG codon of that promoter (see FIG. 27). Therefore, at least a portion of the IFN produced by these plasmids will be mature IFN, e.g., IFN without any amino acids from the signal sequence. In minicells the yield of IFN-α2 obtained with plasmid LAC-AUG(α2) was 5–10 million units per liter.

Another IFN-α2 construction based on similar linking principles has also been made. Here, the penicillinase expression control sequence of pBR322 has been connected via an AUG initiator codon to the IFN-α2 gene from Hif-II-206.* This plasmid designated as β-lac-AUG(α2) when used to transform host cells affords the production of IFN-α2 without fusion to other protein sequences. In minicells, yields of 50–100 million units per liter have been observed. This plasmid is the most preferred plasmid. for use in accordance with this invention. It is also preferred for use with the other IFN-α genes disclosed herein. The preferred host in accordance with this invention is *E. coli* DS410 (ara azide TonA lac y Tsx min a min b gal λ xyl step$^R$). This strain has been deposited together with an example of the preferred plasmid β-lac-AUG(α2) as HcIF-K.

* This construction could most effectively be made by partial digestion of pBR322 with NboII, treating with S1, attaching EcoRI linkers as before and reinserting the fragment into the EcoRI site of pBR322 and deleting one EcoRI site. The resulting plasmid ("β-lac-AUG plasmid") could then be combined with an Sl treated (mild) HindII linker-BsRI fragment of 206 described previously. After cleavage with EcoRI and treating with S1 and phosphatase, the expression plasmid β-lac-AUG(α2) is isolated. Constructions with other genes could be done in a similar fashion by merely utilizing the constructed β-lac-AUG plasmid for insertion of other genes or constructions or more preferably by using the Sau3A site in plasmid β-lac-AUG(α2) itself.

Other constructions using various promoter sequences, ribosome binding sites, Shine-Dalgarno'sequences and DNA sequences between the promoter and the AUG initiator codon and using various of the IFN-α genes disclosed herein can also be constructed using similar methods and principles. These constructions are of course envisioned by this invention and are within the scope thereof.

Hybrid Molecules of IFN-α1 and IFN-α2

A number of hybrid molecules of IFN-α1 and IFN-α2 have been constructed. surprisingly these hybrid constructions have quantitatively different properties and activities as compared either of their parents —IFN-α1 or IFN-α2.

Referring now to FIG. 28, a schematic outline of the construction of four of these hybrid molecules is displayed.

For convenience these hybrid molecules are designated as plasmids I, II, III and IV. In these constructions digestions with restriction enzymes (obtained from Biolabs, with the exception of BspI, a gift of Dr. Kiss) were carried out essentially as recommended by the suppliers. Partial DNA cleavages were carried out with decreased amounts of enzyme. After heat inactivation (65° C., 30 min) of the restriction enzyme, the samples 10 were adjusted to 50 mm Tris-HCl (pH 8) and if required calf intestine alkaline phosphatase (Boehringen) (1 vol per μg DNA) were added. After30 min at 37° C., the samples were extracted with phenol and ether. In most cases the DNA fragments were separated on low temperature gelling agarose (0.8%). For ligation the fragment containing gel pieces (about 20 μl each) were melted at 65° C., cooled to 37° C. and 20 U per μl T4 DNA ligase was added. The mixture was kept at 15° C. for 16 hrs and ligation occurred in the solidified gel (H. Lehrach, personal communication (1980)). One tenth vol of 100 mm Tris-HCl (pH 7.5), 100 mM $CaCl_2$, 100 mM $MgCl_2$ was added, the sample heated 5 min at 65° C. and cooled to 37° C. The samples were then added to $Ca^{+2}$ —treated mini cells, incubated at 0° C. for 20 min, heated 1 min at 42° C. and 10 min at 20° C. and 1 ml tryptone medium added. After incubation for 60 min at 37° C., the cultures were plated on to agar plates containing the appropriate antibiotics. All of the plasmids were characterized by nucleotide sequence analysis across the joint in the IFN sequence.

Hybrid molecule I, an α-1(PvuII)α-2 hybrid, was constructed by partially cleaving C8-IFN-α1 (supra) (CB-α1 in FIG. 28) with PvuII, dephosphorylated, cleaved with PstI and the PstI-PvuII($P_2$) 1346 bp fragment isolated. This fragment was ligated to a 2135 bp PstI(a)-PvuII($P_2$) fragment prepared by totally cleaving C8-IFN-α2 (supra) (C8-α2 in FIG. 28) with PvuII and partially cleaving it with PstI.

Hybrid molecule II, an α-1(BglII)α-2 hybrid, was constructed by cleaving hybrid molecule I with BglII. After dephosphorylation, the large BglII fragment was isolated and ligated to the small BglII fragment of C8-IFN-α2. After cloning, the hybrid plasmid having the small BglII fragment in the correct orientation was identified by restriction analysis.

Hybrid molecule III, an β-2(?PvuII)α-1 hybrid, was constructed by partially cleaving C8-IFN-α1 with PvuII, dephosphorylating, cleaving with AvaI and isolating the 1686 bp PvuII($P_2$)-AvaI and 3233 bp PvuII($P_1$)-AvaI fragments. These fragments were then ligated to the 300 bp PvuII($P_1$)-PvuII($P_2$). fragment of the HcIF-II-206. (supra) (SN206 in FIG. 2B) and the plasmid containing the small PvuII fragment identified by assaying transformed *E. coli* strains for IFN-α activity.

Hybrid molecule IV, an α-2(BglII)α-1 hybrid, was constructed by cleaving C8-IFN-α1 with BglII and AvaI and the 1776 bp fragment isolated. This fragment was then ligated to the 3543 bp BglII-AvaI fragment of hybrid molecule III.

The biological activities of the different interferon species relative to each other were also determined. Cultures of minicells (DS410) transformed with the various plasmids were grown and the bacteria harvested by centrifugation, washed with PBS, suspended in PBS (about 1/20 of the original vol), incubated for 60 min at 0° C. with 1 mg/ml lysozyme, 10 mM EDTA, freeze thawed four times, sheared by passing five times through a syringe and cleaved by centrifugation.

The activities on human, mouse, guinea pig and bovine cells were as follows:

| | Human | Relative IFN Activity | | |
|---|---|---|---|---|
| Protein Source | (FS4) | Bovine (BEK) | Mouse (L) | Guinea Pig |
| C8-IFN-α2 | 1 | 1 | 0.01 | 0.03 |
| C8-IFN-α1 | 0.03 | 1 | 0.3 | 0.03 |
| Hybrid I | 0.001 | 1 | 0.003–0.008 | 0.003–0.01 |
| Hybrid II | 0.001 | 1 | 0.001 | 0.01 |
| Hybrid III | 1 | 1 | 1 | 0.3 |
| Hybrid IV | 0.1 | 1 | 2 | 0.1–0.005 |
| Negative Control | — | — | — | — |

Surprisingly, all of the interferons have about the same activity on bovine cells, yet IFN-α1 and the two hybrid IFN's (I and II) which have the amino terminal moiety of IFN-α1 have about a 10– to 1000-fold lower activity on human cells than IFN-α2 and the two hybrid IFN's (III and IV) having the amino terminal moiety of IFN-α2. It is even more striking that the two hybrid IFN's (I and II) with the amino terminal part of IFN-α1 have more than a 10-fold lower activity on human cells than IFN-α1 itself. Yet, one of the hybrids (III) with the amino terminal part of IFN-α2 has about the same activity on human cells as IFN-α2.

Identification of Chromosomal Genes for INF-α

Figure 18:
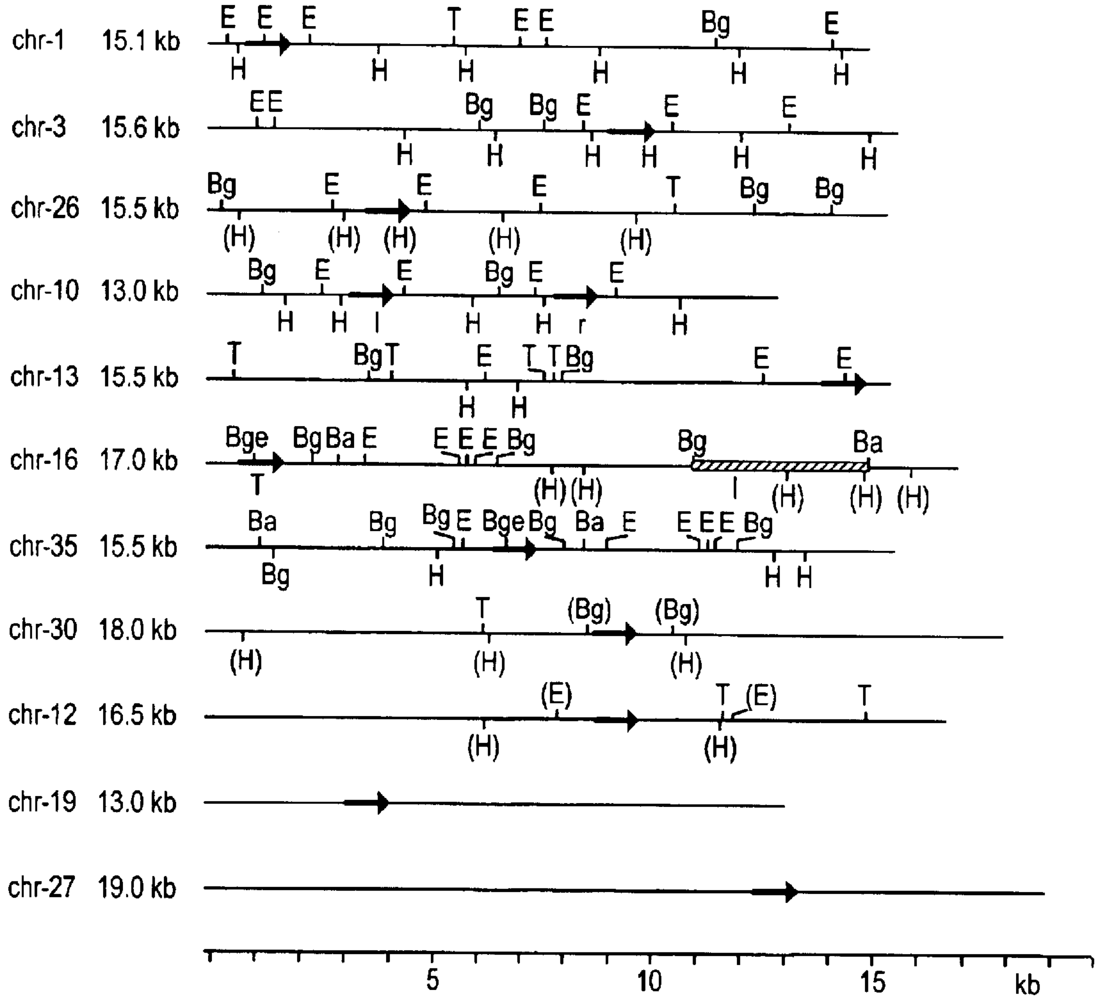
FIG. 18 displays the partial restriction maps of a series of hybrid phages which hybridize to the Hif-2h fragment.

A collection of hybrid phage derived from fragments of fetal human chromosomal DNA which had been generated by partial cleavage with HaeIII and AluI, and joined with EcoRI linkers to λ Charon 4A arms has been prepared by R. M. Lawn et al., *Cell*, 15, pp. 1157–74 (1978). This gene bank was screened by an "in situ" procedure (W. D. Benton and R. W. Davis, Science, 196, pp. 180–82 (1977); T. Maniatis et al., Cell, 15, pp. 687–701 (1978)) using as a probe the $^{32}P$-labelled IFN-αlcDNA insert excised from pBR322(Pst)/Hif-2h. Sixteen hybridization-positive phage clones were isolated from 240,000 plaques by repeated plaque purification (T. Maniatis et al., supra). Ten of the hybrid phage DNA preparations were cleaved with HindIII, TacI, HhaI, BamHI, EcoRI and BglII, respectively, and the fragments separated by electrophoresis on an agarose gel, transferred to a Millipore membrane (E. M. Southern, *J. Mol. Biol.*, 98, pp. 503–17 (1975)) and hybridized with the $^{32}P$-labelled Hif-2h cDNA insert. FIG. 18 summarizes the results in. the form of partial restriction maps and various tables. As displayed there, for each hybrid phage DNA preparation at least a few characteristic restriction sites were established and the region(s) hybridizing to the IFN-α1 gene probe delineated (black arrow).*

Figure 24A:
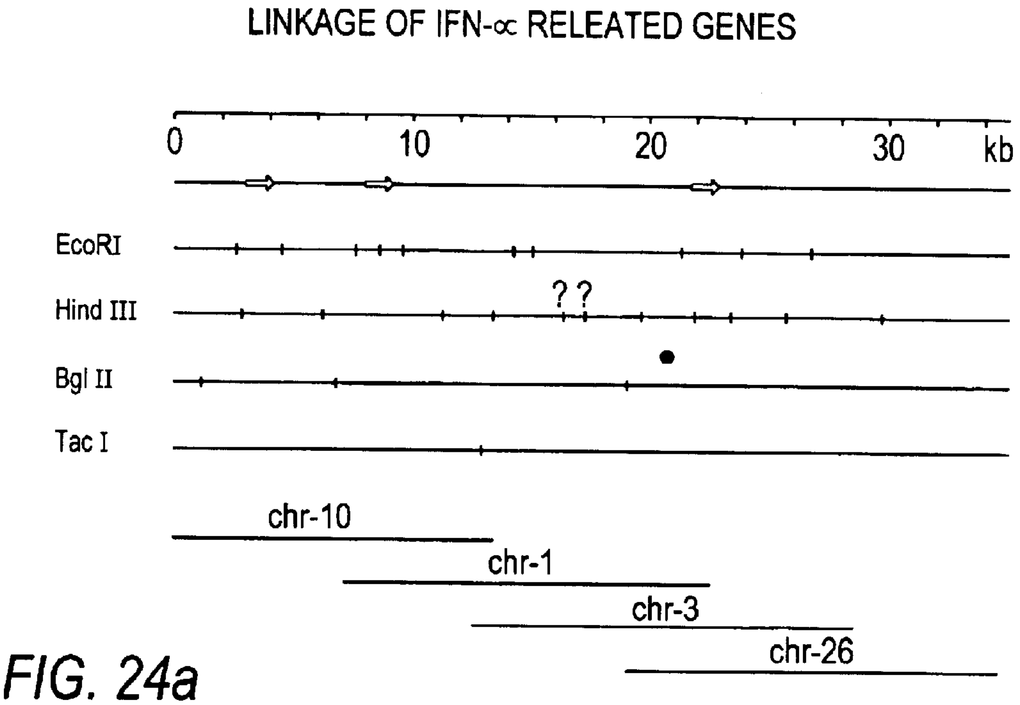
FIG. 24 displays partial; linkage maps for HuIFN-α related genes. The arrows show regions which form R-loops with induced leukocyte poly(A) RNA. The hatched box (chr-16) indicates the sequence which was inferred from blotting experiments, but was not revealed by R-loop mapping.
Figure 24B:
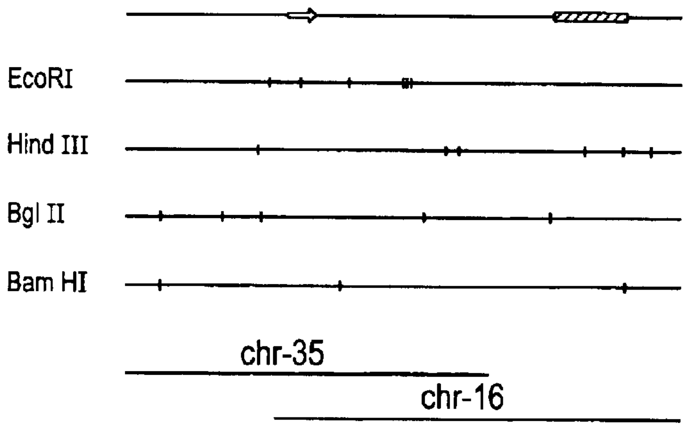

*The shaded area on chr-16 in FIGS. 18 and 24 represents a sequence which hybridizes weakly to Hif-2h cDNA but did not display R-looping.

Referring now to FIGS. 18 and 24, it can be seen that clones chr-3 and chr-26 may represent DNA segments which overlap over much of their length because they have several EcoRI and HindIII fragments in common.

In addition, the hybridizing portion of chr-1 and one of the hybridizing portions of chr-10 may be the same because the HindIII—HindIII and EcoRI-EcoRI fragments, which hybridize with the Hif-2h probe have the same length (3.2 kb and 0.95 kb, respectively). It also appears that the "right-hand" hybridizing portion of chr-16 (labelled "r" in FIG. 18) may be identical with the hybridizing portion of chr-35, although orientated in the opposite direction, inasmuch as each of the two clones yields a 1.4 kb BglII—BglII fragment and a 2 kb EcoRI-EcoRI fragment which hybridize with the Hif-2h cDNA probe. Therefore, most likely the chr-16 and chr-35 inserts overlap.

Accordingly, it appears that the 13 hybridizing portions of the 11 hybrid chromosomal DNAs fall intonot 25 less than 10 distinct classes—chr-1, chr-3, chr-12, chr-13, chr-16 (left hand, labelled “1” in FIG. 18) chr-26, chr-30, chr-35, chr-19 and chr-27.

Referring now to FIG. 24, the overlapping of chr-1, chr-3, chr-10 and chr-26 and that of chr-16 and chr—35 are displayed.

The above data suggests that the genome of an individual human contains not less than 10 different DNA sequences that cross-hybridize to Hif-2h. This conclusion is reinforced by the fact that the proportion of fragment Hif-2h-related sequences detected in the clone bank is about 1 in 16,000. Assuming a value of $3\times10^9$ bp for the haploid human genome, the expected value for a single gene copy with an average DNA fragment size of 16 kb (the average value of the clones examined) is about 1:190,000. Therefore, the frequency of Hif-2h related fragments is 12 times higher than expected for a single gene.

In comparison to these data, when Lawn et al (supra) screened 300,000 plaques from the same gene bank with a β-globin cDNA probe, only 2 positive clones were identified—the expected value being 1.6:300,000. Therefore, there may be 10–15 distinct chromosomal DNA segments in the human genome that cross-hybridize to the Hif-2h fragment or IFN-α1cDNA.

Further Characterization of Hif-chr35

As an illustration only, the hybridizing sequence of chr-35 (“Hif-chr 35”) was further characterized. It is to be understood that the hybridizing portions of the previously described chromosomal hybrid phages could similarly be characterized and handled without departing from the scope of this invention.

The hybridizing portion of chr-35 (“Hif-chr35”) (and the right-hand segment of Hif-chrl6 to which it is most likely identical, supra) is the only hybridizing chromosomal DNA portion with a BglII site. Since IFN-α1 and IFN-α2 cDNA’s have 1 and 2 BglII sites, respectively, within their coding sequences, it seems likely that Hif-chr35 is a counterpart to one of the two previously cloned interferon genes. Hif-chr35’s strong hybridization to the 3' terminal Hif-2h cDNA fragment (containing only the 3' non-coding region) compared to the weaker hybridization of the other of the chromosomal DNAs to this probe supports a likely correspondence of Hif-chr35 and Hif-2h (F. Kafatos et al., *Proc. Natl. Acad. Sci USA*, 74, pp. 5618–22 (1977)).

To analyze the Hif-chr35 fragment further, a HindIII—BamHI fragment was excised from chr-35. This fragment (3.4 kb) contains the hybridizing portion (“Hif-chr35”) of chr-35. This fragment was subcloned into the PstI site of pBR322 using the well-known dC-dC tailing procedures (L. Villa-Komaroff et al., supra) and *E.coli* HB101 transformed with the resultant recombinant DNA molecule using well-known procedures (e.g., S. Nagata et al., *Nature*, 284, pp. 316–20 (1980)).

Clones of these transformants were screened by in-situ colony hybridization (D. Hanahan and M. Meselson, *Gene*, 10, pp. 63–67 (1980)) with the $^{32}$P-labelled Hif-2h fragment (supra) and plasmid DNA—Z-pBR322(Pst)/HchrIF-35HB “EchrIF-35HB”—was the separated from the positive clones (N. M. Wilkie et al., *Nucleic Acids Res.*, 7, pp. 859–77 (1979); Method B). The orientation of the hybrid insert “EchrIF-35EB fragment” in the plasmid with respect to the β-lactamase gene of pBR322 was determined by EcoRI cleavage and sizing of the resulting fragments. The insert orientated to coincide with that of β-lactamase was designated a and the opposite orientation β.

Cultures of these positive clones were grown to an apparent $OD_{650}$=0.8 and the bacteria harvested and lysed by the lysozyme-freeze-thaw method described in S. Nagata et al., supra. Seven of the 10 clones examined showed IFN-α activities of 75 to 500 units/g of cells (cytopathic effect reduction assay).

The DNA insert of one of these 7 IFN-producing clones—*E. coli* BB 101 (Z-pBR322(Pst)/HchrIF-35HBα)—was further characterized by restriction analysis and nucleotide sequence determinaton. Plasmid DNA (HchrIF-35HBα) was prepared from the clone as described previously and the restriction sites determined by Smith-Birnstiel mapping (H. O. Smith and M. L. Birnstiel, *Nucl. Acids Res.*, 3, pp. 2387–98 (1976)): HchrIF-35HBα was digested with EcoRI, labelled at the 5' termini and digested with BglII (and PstI to cleave an undesired fragment of about 1 kb). The 1.04 kb EcoRI—BglII (3' proximal) and the 0.96 kb EcoRI—BglII (5' proximal) fragments were isolated by agarose gel electrophoresis as described by A. C. Peacock and C. W. Dingman, *Biochemistry*, 6, pp. 1818–27 (1967)). Both fragments were partially cleaved with HinfI, BspI and MboII respectively and the products separated on a 1% agarose gel in Tris-αcetate buffer (ph 7.8) containing 1 μg/ml ethidium bromide. After staining, the radioactive bands were visualized by autoradiography. The BstNI and HgiAI sites were similarly determined on the 1.04 kb (31 proximal) fragment. The results of the analysis is shown in FIG. 19.

For nucleotide sequence determination, HchrIF-35HBα was cleaved with various restriction enzymes, the products separated by electrophoresis through a 5% polyacrylamide gel in Tris-borate-EDTA buffer (A. C. Peacock and C. W. Dingman, supra) and extracted from the gel and purified as described by w. Moller et al., *J. Mol. Biol.*, 124, pp. 343–58 (1978).

Figure 19:
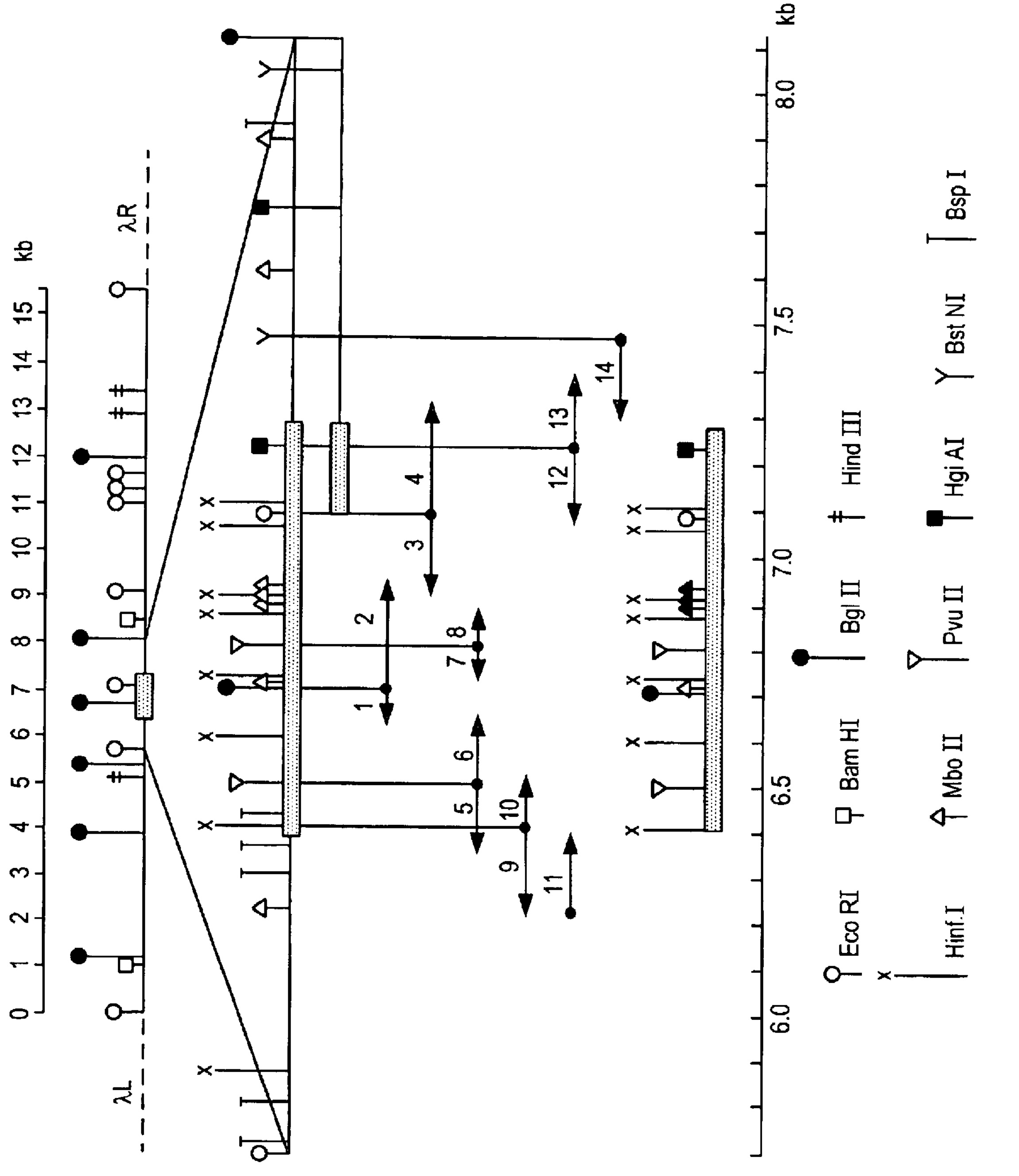
FIG. 19 displays a partial restriction map of the hybrid insert of Z-pBR322Pst/HchrIF-35HBα and the sequencing strategy employed to determine its nucleotide sequence.
Figure 20:
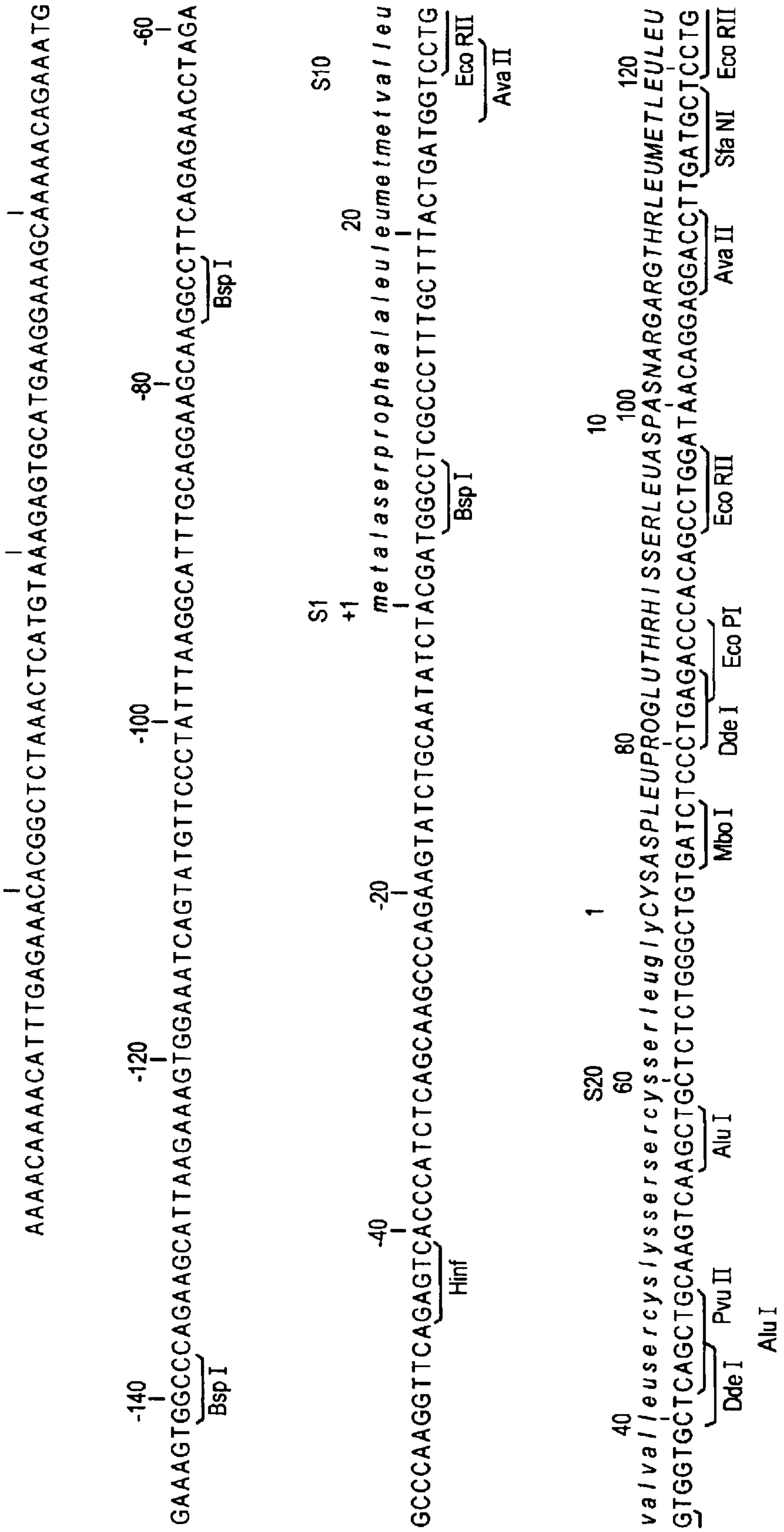
Figure 21:
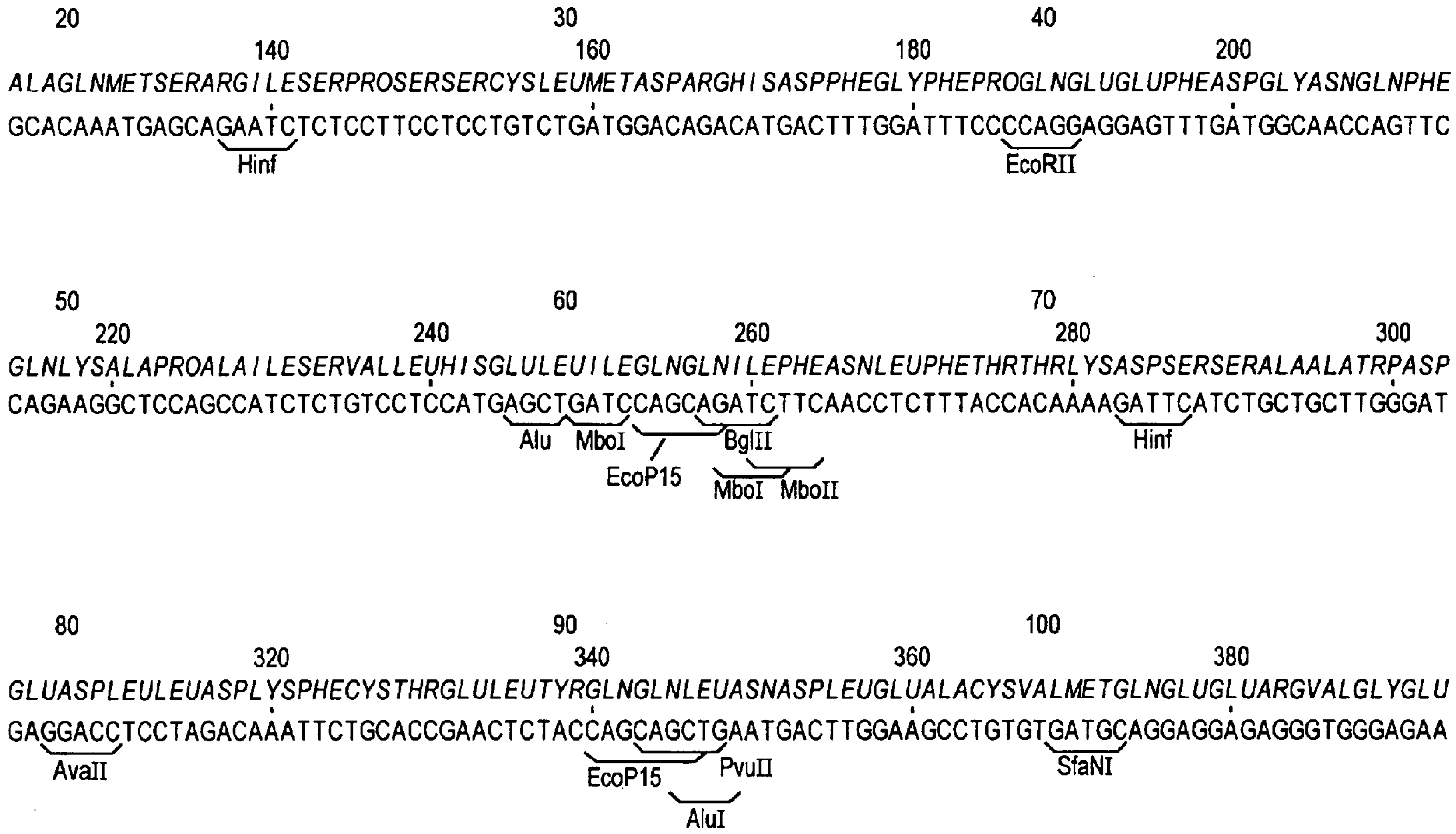

The sequencing strategy employed is depicted in FIG. 19 and described as follows:

1 and 2—cleavage of SchrIF-35HBα with BglII, labelling, cleavage with EcoRI and PstI and isolation of a BglII*-EcoRI fragment (940 bp) (“1”) and a BglII*-EcoRI (360 bp) (“2”);

3 and 4—cleavage of HchrIF-35HBe with EcoRI, labelling, cleavage with BspI and isolation of an EcoRI*-BspI fragment (680 bp) (“3”) and an EcoRI*-BspI, fragment (880 bp) (“4”);

5, 6, 7 and 8—cleavage of HchrIF-35HBa with PvuII, labelling, cleavage with BglI and EcoRI and isolation of PvuII*-EcoRI fragment (780 bp) (“5”), a PvuII*-BII (215 bp) (“6”), a PvuIl*-BglII fragment (90 bp) (“7”), and a PvuII*-EcoRI fragment (290 bp) (“8”);

9 and 10—cleavage of HchrIF-35HBα with EcoRI, isolation by 1% agarose gel electrophoresis in Tris-borate EDTA buffer of a 1300 bp EcoRI-EcoRI fragment, further cleavage with HinfI and isolation of a HinfI—HinfI fragment (450 bp), and a HinfI—HinfI fragment (180 bp). Labelling, of the larger HinfI—HinfI fragment and cleavage with MboII permitted isolation of a HinfI*-MboII (190 bp) (“9”). Labelling of the shorter HinfI—HinfI fragment and cleavage with AvaII permited isolation of a Hinfl*-AvaII fragment (150 bp) (“10”);

11—cleavage of HchrIF-35HBα with MboII, labelling, cleavage with BglII, and isolation of a MboII*-BglII fragment (465 bp) (“11”)

12, 13 and 14—cleavage of HchrIF-35HBα with BspI and BglII, isolation by agarose electrophoresis as above of a 1200 bp BspI—BglII fragment and (a) cleavage with HgiAI, labelling, cleavage with MboII and isolation of an HgiAI*-MboII fragment (300 bp) ("12") and an HgiAI*-MboII fragment (360 bp) ("13"), or (b) cleavage with BsttNI, labelling, cleavage with EcoRI and isolation of a BstNI*-EcoRI fragment (380 bp) ("14").

The various fragments were sequenced by the Maxam-Gilbert procedure (supra). All fragments were sequenced on both strands and across the restriction sites that served as origins for sequencing.

A comparison of the nucleotide sequence of the coding region of HchrIF-35HBα and that of Hif-2h (coding region) (FIGS. 8–10 compared to FIGS. 20–23) reveals that they are identical. In particular, it is surprising that there is no indication of the presence of introns within the coding sequence of the HchrIF-35HBα fragment, i.e., between the HinfI site in the 5' non-coding region and the EcoRI site in the 3' non-coding region. Thus, no intron could be detected in the chromosomal sequence corresponding to mature IFN-αmRNA.

Further Characterization of Hif-chr 26 and Hif-chr 3

The gene-containing segments of chr-3 and chr-26, which appear identical by heteroduplex analysis but differ in at least one BglII restriction site were examined by nucleotide sequencing. Five nucleotide differences in 725 base pairs were founds only two of these appear in the coding sequences. Since not only the genes, but at least 3.5 Kbp preceding and 6.0 np following them formed a perfect heteroduplex and because of the relatively low sequence divergence which entails only 2 amino acid changes, it appears that Hif-chr3 and Hif-chr26 are allelic forms of the same gene. These aredesignated IFN-α4a (Hif-chr3) and IFN-α4b (Hif-chr26). The nucleotide sequence and corresponding amino acid sequence of IFN-α4b determined by conventional sequencing techniques described previously is displayed in FIGS. 29–32.

A comparison of FIGS. 29–32 with FIGS. 8–10, 12–16 and 20–23 reveals that the proteins encoded by each of the sequences differ from each other in about 15% of their residues. This divergence is typical for products of non-allelic genes which have diverged 20–90 million years ago.

Expression of Hif-chr35 in Mouse Cells

Plasmid Z-pBR322(Pst)/HchrIF-35HBα (supra) was used as a source of a Hif-chr35 fragment for expression in mouse cells. The plasmid was restricted with PstI and treated with 5' exonuclease to remove the 5' dG tails. This fragment was then inserted into a 5' dG-tailed KpnI fragment of a plasmid prepared by joining the BamHI—BamHI fragments of pBR322 and polynoma DNA. The resulting vector was used to transform mouse 3T3 cells using the calcium phosphate technique (N. Mantei et al., *Nature*, 281 pp. 40–46(1979)). These transformed cells are designated for convenience Mouse 3T3 (polynoma-Hif-chr35). After 20–40 hours, assays revealed an IFN-α activity of 300 units/ml of IFN-α on human cells and about 3000 units/ml of IFN-α on bovine cells.

It should of course be understood that the nucleotide sequences depicted in FIGS. 8–10, 12–16, 20–23 and 29–32 do not take into account any modifications to the nucleotide sequences such as mutation, including single or multiple, base'substitutions, insertions, inversions or deletions which may have already taken place or which may subsequently be employed. Moreover, the sequence also does not take into account the possible substitution of other codons coding for the same amino acid as a codon depicted in these figures. Therefore, it should be understood that such modified sequences as code for polypeptides displaying an immunological or biological activity of IFN-α are also within this invention.

In addition, it is to be understood that the amino acid sequences depicted in FIGS. 8–10, 12–16, 20–23 and 29–32 do not take into account any modifications to the polypeptides causedby their interaction with in vivo or in vitro agents e.g. in vivo glycosolation enzymes. Therefore, it must be understood that fragments and derivatives of these polypeptides that display an, immunological or biological activity of IFN-α are also part of this invention.

Production of Polypeptides Displaying an Immunological or Biological Activity of Interferon in Bacterial Hosts Since the cytopathic effort reduction assay (W. E. Stewart II and S. E. Sulkin, *S. E. Proc. Soc. Exp. Biol. Med.*, 123, pp. 650–53 (1966)) can detect minute amounts of IFN—less than one active molecule per bacterial cell—lysates of *E. coli* HB101 infected with the ten hybrid A phages, described previously, were assayed for the presence of IFN. Seven of the eleven phages (all except chr-10, chr-12, chr-19 and chr-27) gave lysates containing IFN activity ranging from 3 to 50 units/ml. In the case of chr-10 and chr-12, the hybridizing (to Hif-2h) HindIII—HindIII or EcoRI-EcoRI fragments, subcloned into the PstI site of pBR322, as described previously, expressed IFN-α activity in *E. coli*. Since *E. coli* is believed to be incapable of splicing mRNA (0. Mercereau-Puijalon and P. Kourilsky, *Nature*, 279, pp. 647–49 (1979)), these IFN-α chromosomal genes most likely do not contain introns in their coding region.

Final Conclusions

We have isolated a set of recombinant DNA molecules containing cDNA prepared from poly(A) RNA from Sendai virus-treated (induced) human leukocytes, representatives of which have the following properties:

(1) They hybridize to poly(A) RNA from induced but not from non-induced human leukocytes.

(2) They hybridize to IFN-αmRNA as shown by their capacity to select this RNA from a mixture of RNAs, and by their capacity to inhibit (reversibly) translation of interferon MRKA in the hybrid arrested translation assay.

(3) *E. coli* containing certain members of the set produce a compound with the following properties:

(a) It is sensitive to trypsin (b) It exhibits IFN-α activity in a human cell system and only slight activity in a mouse cell system (c) It has a molecular weight between 20,000 and 30,000 (19,388 based on the nucleotide sequencing of FIGS. 8–10)

(d) The IFN-α activity is specifically inhibited by antibody to human leukocyte interferon.

(4) The DNA inserts of the hybrid plasmids of this invention are able, in addition to their ability to select IFN-αmRNA from a mixture of RNAs, to select IFN-aDNA from mixtures of various sources including cDNAs and from hybrid phage gene banks of chromosomal DNA.

(5) A number of different chromosomal genes for IFN-α exist. It is unexpected that these genes lack introns and permit direct expression of interferon and interferon-like polypeptides in appropriate hosts.

(6) At least three of[]the nucleotide sequences of the DNA inserts of these recombinant DNA molecules are different and suggest the existence of at least three non-allelic genes for IFN-α.

(7) The proteins coded for by these three nucleotide sequences are different from the 35 amino acids determined from authentic lymphoblastoid interferon.

(8) Sybrid proteins prepared for various combinations of IFN-α gene segments display quantitatively different properties than each other or their parents and proteins having additional amino acids fused to IFN-α or proteins comprising IFN-α without a portion of its amino terminal sequence display IFN activity.

These properties demonstrate that the recombinant DNA molecules described by this invention contain at least a part of the coding sequence for human leukocyte interferon and that some of these plasmids lead to expression in E. coli of a polypeptide with an immunological or biological activity of human leukocyte interferon. It should also be evident that the polypeptides disclosed herein may be fragmented, modified or derivatized, as is well known in the protein art, without departing from the scope or disclosure of this invention.

Micro-organisms and recombinant DNA molecules prepared by the processes described herein are exemplified by cultures deposited in the culture collection Deutsche sammlurg von Nikroorganisrmen, in Gottingen, West Germany on Jan. 7, 1980, and identified as HcIF-A to E:

A: *E. coli* HB101 (Z-pBR322(Pst)/HcIF-4c)
B: *E. coli* HB101 (Z-pBR322(Pst)/HcIF-2h)
C: *E. coli* HB101 (Z-pBR322(Pst)/HcIF-SN35)
D: *E. coli* HB101 (Z-pBR322(Pst)/HcIF-SN42)
E: *E. coli* HB101 (Z-pKT287(Pst)/HcIF-2h-AH6)

These cultures were assigned accession numbers DSM 1699–1703, respectively.

In addition, micro-organisms and recombinant DNA molecules prepared by the processes described herein are exemplified by cultures deposited in the culture collection of the American Type Culture collection, Rockville, Md. on Mar. 27, 1980 and identifid ar HcLF to H, and assigned ATCC accession numbers 31633 and 31,634 respectively:

G: *E. coli* HB101 (Z-pBR322(Pst)/HcIF-II-206)
H: *E. coli* HB101 (Z-pBR322(Pst)/HcIF-SN35-AHL6)

Other micro-organisms prepared by the processes described herein are exemplified by cultures deposited in the culture collection Deutsche Sammlung von Mikroorganismem, in Gottingen, West Germany on Oct. 1, 1980 and identified as HchrIF-A through J, and assigned accession numbers DSM 1914–1923:

A. subcloned Hindill fragmentof chr 3 in *E. coli HB*101;
B. subcloned EcoRI fragment of chr 12 in *E. coli HB*101;
C. subcloned HindIII fragment of chr 12 in *E. coli HB*101;
D. subcloned EcoRI fragment of chr 13 in *E. coli HB*101;
E. subcloned EcoRI fragment of chr 23 in *E. coli HB*101;
F. subcloned HindIII fragment of chr 23 in *E. coli HB*101;
G. subcloned EcoRI fragment of chr 26 in *E. coli HB*101;
H. subcloned HindIII fragment of chr 26 in *E. coli HB*101;
I. subcloned HindIII/BamHI fragment of chr 35 in *E. coli* HB101;
J. subcloned BamHI fragment of chr 35 in *E. coli* HB101.

Finally, micro-organisms prepared by the processes described herein are exemplified by cultures deposited in the American Type Culture Collection, Rockville, Md., on Dec. 15, 1980 and identified as HchrIF-K through HchrIF-Q and HcIF-I through HcIF-K, and assigned ATTC accession numbers 31760–31769, respectively:

K. subcloned Tac—Tac fragment of chr 23 in *E. coli HB*101.
L. subcloned BglII—BglII fragment of chr 10 l in *E. coli* EB101.
M. subcloned HindIII—HindII fragment of chr lor in *E. coli* HB101.
N. subcloned BglII—BglII fragment of chr 26 in *E. coli* HB101.
O. subcloned HindIII—HindIII fragment of chr 30 in *E. coli* HB101.
P. subcloned BglII-Tac fragment of chr 13 in *E. coli HB*101.
Q. subeloned BglII-Tac fragment of chr 16 l in *E. coli HB*101.

HcIF-I: *E. coli* DS410 (C8-IFN-α2)
HcIF-J: *E. coli* DS41D (LAC-AUG(α2))
HcIF-K: *E. coli* DS410 (β-Lac-AUG(α2))

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which have been presented hereinbefore by way of example.

What is claimed is:

1. A recombinant DNA molecule comprising:
(a) the portion of a DNA sequence selected from the group consisting of the following subcloned fragments that hybridizes to at least one of the DNA inserts of Z-pBR322 (Pst)/HcIF-II-206 and Z-pBR322 (Pst)/HcIF-SN35-AHL6:

HchrIF-A, the subcloned HindIII fragment of chr 3 in *E.coli* HB101;

HchrIF-B, the subcloned EcoRI fragment of chr 12 in *E.coli* HB101;

HchrIF-C, the subcloned HindIII fragment of chr 12 in *E.coli* HB101;

HchrIF-D, the subcloned EcoRI fragment of chr 13 in *E.coli* HB101;

HchrIF-E, the subcloned EcoRI fragment of chr 23 in *E.coli* HB101;

HchrIF-F, the subdloned HindIII fragment of chr 23 in *E.coli* HB101;

HchrIF-G, the subcloned EcoRI fragment of chr 26 in *E.coli* HB 101; and

HchrEF-H, the subcloned HindIII fragment of chr 26 in *E.coli* HB101, or (b) a DNA sequence that on expression codes for a polypeptide coded for on expression by said hybridizing portion of any of the foregoing DNA inserts.

2. A recombinant DNA molecule comprising a DNA sequence selected from the group consisting of:
(a) DNA sequences of the formula:
TTACTGGTGGCCCTCCTGGTGCTCAGCT-
GCAAGTCAAGCTGCTCTGTGGGCTGT-
GATCTGCCTCAAACCCACAGCCTGGG-
TAGCAGGAGGACCTTGATGCTCCTGGCACAGAT
GAGGAGAATCTCTCTTTTCTCCTGCT-
TGAAGGACAGACATGACTTTGGATTTC-
CCCAGGAGGAGTTTGGCAACCAGTTC-
CAAAAGGCTGAAACCATCCCTGTCCTCCATGAG ATGATCCAGCAGATCTTCAATCTCT-
TCAGCACAAAGGACTCATCTGCTGCT-
TGGGATGAGACCCTCCTAGACAAATTC-
TACACTGAACTCTACCAGCAGCTGAATGACCTG
GAAGCCTGTGTGATA-
CAGGGGGTGGGGGTGACAGAGACTC-
CCCTGATGAAGGAGGACTCCATTCTG-
GCTGTGAGGAAATACTTCCAAAGAATCACTCTC
TATCTGAAAGAGAAGAAATACAGCCCT-
TGTGCCTGGGAGGTTGTCAGAGCA-
GAAATCATGAGATCTTTTTCTTTGTCAA-
CAAACTTGCAAGAAAGTTAAGAAGTAAGGAA and
TGTGATCTGCCTCAAACCCACAGCCTGGGTAG
CAGGAGGACCTTGATGCTCCTGGCACAGATGA GG
AGAATCTCTCTTTTCTCCTGCTTGAAGGACAGA
CATGACTTTGGATTTCCCCAGGAGGAGTTTGGCA
ACCAGTTCCAAAAGGCTGAAACCATCCCTGTCCT
CCATGAGATGATCCAGCAGATCTTCAATCTCTT
CAGCACAAAGGACTCATCTGCTGCTTGGGATGAG
ACCCTCCTAGACAAATTCTACACTGAACTCTACC
AGCAGCTGAATGACCTGGAAGCCTGTGTGATAC
AGGGGGTGGGGGTGACAGAGACTCCCCTGATG
AAGGAGGACTCCATTCTGGCTGTGAGGAAATACT
TCCAAAGAATCACTCTCTATCTGAAAGAGAAGA
AATACAGCCCTTGTGCCTGGGAGGTTGTCAGAGC
AGAAATCATGAGATCTTTTTCTTTGTCAACAAAC
TTGCAAGAAAGTTTAAGAAGTAAGGAA, and (b) a DNA sequence that on expression codes for a polypeptide coded for on expression by either of the foregoing DNA sequences.

3. A recombinant DNA molecule comprising a DNA sequence selected from the group consisting of:

(a) DNA sequences of the formula:

ATGGCCCTGTCCTTTTCTTTACTGATG-
GCCGTGCTGGTGCTCAGCTACAAATC-
CATCTGTTCTCTGGGCTGTGATCTGCCT-
CAGACCCACAGCCTGGGTAATAGGAGGACCTT
GATACTCCTGCAACAAATGGGAA-
GAATCTCTCATTTCTCCTGCCTGAAGGA-
CAGACATGATTTCGGATTCCCCGAGGAG-
GAGTTTGATGGCCACCAGTTCCAGAAGACTCAA
GCCATCTCTGTCCTCCATGAGATGATC-
CAGCAGACCTTCAATCTCTTCAGCACA-
GAGGACTCATCTGCTGCTTGGGAACA-
GAGCCTCCTAGAAAAATTTTCCACTGAACTTTA
CCAGCAACTGAATGACCTGGAAGCATGT-
GTGATACAGGAGGTTGGGGTGGAA-
GAGACTCCCCTGATGAATGTGGACTC-
CATCCTGGCTGTGAGGAAATACTTCCAAAGAATC
ACTCTTTATCTAACAGAGAAGAAATA-
CAGCCCTTGTGCCTGGGAGGTTGTCA-
GAGCAGAAATCATGAGATC-
CCTCTCGTTTTCAACAAACTTGCAAAAAAGATTA
AGGAGGAAGGATand
TGTGATCTGCCTCAGACCCACAGCCTGGGTAATA
GGAGGACCTTGATACTCCTGCAACAAATGGGAA
GAATCTCTCATTTCTCCTGCCTGAAGGACAGACA
TGATTTCGGATTCCCCGAGGAGGAGTTTGATGGCC
ACCAGTTCCAGAAGACTCAAGCCATCTCTGTCC
TCCATGAGATGATCCAGCAGACCTTCAATCTCTT
CAGCACAGAGGACTCATCTGCTGCTTGGGAACA
GAGCCTCCTAGAAAAATTTTCCACTGAACTTTAC
CAGCAACTGAATGACCTGGAAGCATGTGTGATA
CAGGAGGTTGGGGTGGAAGAGACTCCCCTGATGA
ATGTGGACTCCATCCTGGCTGTGAGGAAATACTT
CCAAAGAATCACTCTTTATCTAACAGAGAAGAAA
TACAGCCCTTGTGCCTGGGAGGTTGTCAGAGCA
GAAATCATGAGATCCCTCTCGTTTTCAACAAACT
TGCAAAAAAGATTAAGGAGGAAGGAT, and (b)a DNA sequence that on expression codes for a molypeptide coded for on expression by either of the foregoing DNA sequences.

4. The recombinant DNA molecule according to claim 1 or 3, wherein said DNA sequence is operatively linked to an expression control sequence.

5. The recombinant DNA molecule according to claim 4, wherein said expression control sequence controls the expression of genes of prokaryotic or eukaryotic cells and their viruses.

6. The recombinant DNA molecule according to claim 5, wherein said expression control sequence is selected from the group consisting of a lac system, β-lac system, a trp system, major operator and promoter regions of phage λ, and the control region of fd coat protein.

7. A recombinant DNA molecule selected from the group consisting of C8-IFN-α2, LAC-AUG(α2) and β-lac-AUG (α2).

8. A host cell transformed with at least one recombinant DNA molecule according to any one of claims 1, 3 and 7.

9. The host cell of claim 8 selected from the group consisting of bacteria, yeasts, animal cells in culture, and human tissue cells.

10. A host cell transformed with at least one recombinant DNA molecule according to claim 4.

11. The host cell of claim 10 wherein said expression control sequence controls the expression of genes of prokaryotic or eukaryotic cells and their viruses.

12. The host cell of claim 11 wherein said expression control sequence is selected from the group consisting of a lac system, a β-lac system, a trp system, major operator and promoter regions of phage λ, and the control region of fd coat protein.

13. The host cell of claim 10 selected from the group consisting of bacteria, yeasts, animal cells in culture, and human tissue cells.

14. The recombinant DNA molecule according to claim 2, wherein said DNA sequence is operatively linked to an expression control sequence.

15. The recombinant DNA molecule according to claim 14, wherein said expression control sequence controls the expression of genes of prokaryotic or eukaryotic cells and their viruses.

16. The recombinant DNA molecule according to claim 15, wherein said expression control sequence is selected from the group consisting of a lac system, a β-lac system, a trp system, major operator and promoter regions of phage λ, and the control region of fd coat protein.

17. A host cell transformed with at least one recombinant DNA molecule according to any one of claims 2 and 14–16.

18. The host cell of claim 17 selected from the group consisting of bacteria, yeasts, animal cells in culture, and human tissue cells.

19. A method for producing a recombinant DNA molecule comprising a DNA sequence selected from the group consisting of:

(a) DNA sequences of the formula:

ATGGCCCTGTCCTTTTCTTTACTGATG-
GCCGTGCTGGTGCTCAGCTACAAATC-
CATCTGTTCTCTGGGCTGTGATCTGCCT-
CAGACCCACAGCCTGGGTAATAGGAGGACCTT
GATACTCCTGCAACAAATGGGAA-
GAATCTCTCATTTCTCCTGCCTGAAGGA-
CAGACATGATTTCGGATTCCCCGAGGAG-
GAGTTTGATGGCCACCAGTTCCAGAAGACTCAAG
CCATCTCTGTCCTCCATGAGATGATC-
CAGCAGACCTTCAATCTCTTCAGCACA-

GAGGACTCATCTGCTGCTTGGGAACA-
GAGCCTCCTAGAAAAATTTTCCACTGAACTTTTA
CCAGCAACTGAATGACCTGGAAGCATGT-
GTGATACAGGAGGTTGGGGTGGAA-
GAGACTCCCCTGATGAATGTGGACTC-
CATCCTGGCTGTGAGGAAATACTTCCAAAGAAT
CACTCTTTATCTAACAGAGAAGAAATA-
CAGCCCTTGTGCCTGGGAGGTTGTCA-
GAGCAGAAATCATGAGATC-
CCTCTCGTTTTCAACAAACTTGCAAAAAAGATTA
AGGAGGAAGGAT and TGTGATCTGCCTCAGACCCA-
CAGCCTGGGTAATA GGAGGACCTTGATACTCCTG-
CAACAAATGGGAA GAATCTCTCATTTCTCCTGCCT-
GAAGGACAGACA
TGATTTCGGATTCCCCGAGGAGGAGTTTGATGGC
CACCAGTTCCAGAAGACTCAAGCCATCTCTGT
CCTCCATGAGATGATCCAGCAGACCTTCAATCTC
TTCAGCACAGAGGACTCATCTGCTGCTTGGGAAC
AGAGCCTCCTAGAAAAATTTTCCACTGAACTTTA
CCAGCAACTGAATGACCTGGAAGCATGTGTGAT
ACAGGAGGTTGGGGTGGAAGAGACTCCCCTGA
TGAATGTGGACTCCATCCTGGCTGTGAGGAAAT
ACTTCCAAAGAATCACTCTTTATCTAACAGAGAA
GAAATACAGCCCTTGTGCCTGGGAGGTTGTCA
GAGCAGAAATCATGAGATCCCTCTCGTTTTCAA
CAAACTTGCAAAAAAGATTAAGGAGGAAGGAT, and (b) a DNA sequence that on expression codes for a polypeptide coded for on expression by either of the foregoing DNA sequences, comprising the step of culturing a host cell containing at least one recombinant DNA molecule of claim 3 under conditions in which the host cell replicates the recombinant DNA molecule.

20. A transformed host cell, wherein said host cell is *E.coli* HB101 (Z-pBR322(Pst)/HcIF-II-206).

21. A transformed host cell selected from the group consisting of HchrIF-A, wherein HcHrIF-A is the subcloned HindIII fragment of chr 3 in *E.coli* HB101; HchrIF-B, wherein HcHrIF-B is the subcloned EcoRI fragment of chr 12 in *E.coli* HB101; HchrIF-C, wherein HcHrIF-C is the subeloned HindIII fragment of chr 12 in *E.coli* HB101; HchrIF-D, wherein HchrIF-D is the subcloned EcoRI fragment of chr 13 in *E.coli* HB101; HcHrIF-E, wherein HcHrIF-E is the subcloned EcoRI fragment of chr 23 in *E.coli* HB101; HchrIF-F, wherein HchrIF-F is the subcloned HindIII fragment of chr 23 in *E.coli* HB101; HcHrIF-G, wherein HchrIF-G is the subcloned EcoRI fragment of chr 26 in *E.coli* HB101; and HchrIF-H, wherein HchrIF-H is the subcloned HindIII fragment of chr 26 in *E.coli* HB101.

22. A transformed host cell selected from the group consisting of *E.coli* DS410 (C8-IFN-α2), *E.coli* DS410 (LAC-AUG(α2)) and *E.coli* DS410 HB101 (βlac-AUG (α2)).

23. A method for producing a recombinant DNA molccule comprising a DNA sequence selected from the group consisting of:

(a) DNA sequences of the formula:

TTACTGGTGGCCCTCCTGGTGCTCAGCT-
GCAAGTCAAGCTGCTCTGTGGGCTGT-
GATCTGCCTCAAACCCACAGCCTGGG-
TAGCAGGAGGACCTTGATGCTCCTGGCACAGATG
AGGAGAATCTCTCTTTTCTCCTGCT-
TGAAGGACAGACATGACTTTGGATTTC-
CCCAGGAGGAGTTTGGCAACCAGTTC-
CAAAAGGCTGAAACCATCCCTGTCCTCCATGAG
ATGATCCAGCAGATCTTCAATCTCT-
TCAGCACAAAGGACTCATCTGCTGCT-
TGGGATGAGACCCTCCTAGACAAATTC-
TACACTGAACTCTACCAGCAGCTGAATGACCTG
GAAGCCTGTGTGATA-
CAGGGGGTGGGGGTGACAGAGACTC-
CCCTGATGAAGGAGGACTCCATTCTG-
GCTGTGAGGAAATACTTCCAAAGAATCACTCTC
TATCTGAAAGAGAAGAAATACAGCCCT-
TGTGCCTGGGAGGTTGTCAGAGCA-
GAAATCATGAGATCTTTTTCTTTGTCAA-
CAAACTTGCAAGAAAGTTTAAGAAGTAAGGAA and
TGTGATCTGCCTCAAACCCACAGCCTGGGTAGC
AGGAGGACCTTGATGCTCCTGGCACAGATGAG
GAGAATCTCTCTTTTCTCCTGCTTGAAGGACAG
ACATGACTTTGGATTTCCCCAGGAGGAGTTTGG
CAACCAGTTCCAAAAGGCTGAAACCATCCCTGT
CCTCCATGAGATGATCCAGCAGATCTTCAATCT
CTTCAGCACAAAGGACTCATCTGCTGCTTGGGA
TGAGACCCTCCTAGACAAATTCTACACTGAAC
TCTACCAGCAGCTGAATGACCTGGAAGCCTGTG
TGATACAGGGGGTGGGGGTGACAGAGACTCCCC
TGATGAAGGAGGACTCCATTCTGGCTGTGAGG
AAATACTTCCAAAGAATCACTCTCTATCTGAAA
GAGAAGAAATACAGCCCTTGTGCCTGGGAGGTT
GTCAGAGCAGAAATCATGAGATCTTTTTCTTTGT
CAACAAACTTGCAAGAAAGTTTAAGAAGTAAGG
AA, and (b) a DNA sequence that on expression codes for a polypeptide coded for on expression by either of the foregoing DNA sequences;

comprising the step of culturing a host cell containing at least one recombinant DNA molecule of claim 2 under conditions in which the host cell replicates the recombinant DNA molecule.

24. A DNA sequence coding for an α-interferon selected from the group consisting of:

(a) DNA sequences of the formula:

TTACTGGTGGCCCTCCTGGTGCTCAGCT-
GCAAGTCAAGCTGCTCTGTGGGCTGT-
GATCTGCCTCAAACCCACAGCCTGGG-
TAGCAGGAGGACCTTGATGCTCCTGGCACAG
ATGAGGAGAATCTCTCTTTTCTCCTGCT-
TGAAGGACAGACATGACTTTGGATTTC-
CCCAGGAGGAGTTTGGCAACCAGTTC-
CAAAAGGCTGAAACCATCCCTGTCCTCCATGA
GATGATCCAGCAGATCTTCAATCTCT-
TCAGCACAAAGGACTCATCTGCTGCT-
TGGGATGAGACCCTCCTAGACAAATTC-
TACACTGAACTCTACCAGCAGCTGAATGACCTG
GAAGCCTGTGTGATA-
CAGGGGGTGGGGGTGACAGAGACTC-
CCCTGATGAAGGAGGACTCCATTCTG-
GCTGTGAGGAAATACTTCCAAAGAATCACTCTCT
ATCTGAAAGAGAAGAAATACAGCCCT-
TGTGCCTGGGAGGTTGTCAGAGCA-
GAAATCATGAGATCTTTTTCTTTGTCAA-
CAAACTTGCAAGAAAGTTTAAGAAGTAAGGAA and
TGTGATCTGCCTCAAACCCACAGCCTGGGT AG
CAGGAGGACCTTGATGCTCCTGGCACAGATGAG
GAGAATCTCTCTTTTCTCCTGCTTGAAGGACA GA
CATGACTTTGGATTTCCCCAGGAGGAGTTTGGC
AACCAGTTCCAAAAGGCTGAAACCATCCCTGT
CCTCCATGAGATGATCCAGCAGATCTTCAATCTC
TTCAGCACAAAGGACTCATCTGCTGCTTGGGAT
GAGACCCTCCTAGACAAATTCTACACTGAACTCT
ACCAGCAGCTGAATGACCTGGAAGCCTGTGTGA
TACAGGGGGTGGGGGTGACAGAGACTCCCCTG
ATGAAGGAGGACTCCATTCTGGCTGTGAGGA AATACTTCCAAAGAATCACTCTCTATCTGAAAGA AAGAAATACAGCCCTTGTGCCTGGGAGGTTGTCA GAGCAGAAATCATGAGATCTTTTTCTTTGTCAA CAAACTTGCAAGAAAGTTTAAGAAGTAAGGAA, and (b) a DNA sequence that on expression codes for a polypeptide coded for on expression by either of the foregoing DNA sequences.

25. A method for producing a DNA molecule comprising a DNA sequence encoding an α-interferon comprising the step of culturing a host cell containing a DNA molecule comprising the DNA sequence of claim 24 under conditions in which the host cell replicates the DNA molecule.

26. A DNA sequence coding for an α-interferon selected from the group consisting of:

(a) DNA sequences of the formula:

ATGGCCCTGTCCTTTTCTTTACTGATG-GCCGTGCTGGTGCTCAGCTACAAATC-CATCTGTTCTCTGGGCTGTGATCTGCCT-CAGACCCACAGCCTGGGTAATAGGAGGACCT TGATACTCCTGCAACAAATGGGAA-GAATCTCTCATTTCTCCTGCCTGAAGGA-CAGACATGATTTCGGATTCCCCGAGGAG-GAGTTTGATGGCCACCAGTTCCAGAAGACTCAA GCCATCTCTGTCCTCCATGAGATGATC-CAGCAGACCTTCAATCTCTTCAGCACA-GAGGACTCATCTGCTGCTTGGGAACA-GAGCCTCCTAGAAAAATTTTCCACTGAACTTT ACCAGCAACTGAATGACCTGGAAGCAT-GTGTGATACAGGAGGTTGGGGTGGAA-GAGACTCCCCTGATGAATGTGGACTC-CATCCTGGCTGTGAGGAAATACTTCCAAAGAA TCACTCTTTATCTAACAGAGAAGAAATA-CAGCCCTTGTGCCTGGGAGGTTGTCA-GAGCAGAAATCATGAGATC-CCTCTCGTTTCAACAAACTTGCAAAAAAGAT TAAGGAGGAAGGAT and TGTGATCTGCCTCAGACCCACAGCCTGGGTAA TAGGAGGACCTTGATACTCCTGCAACAAATG GGAAGAATCTCTCATTTCTCCTGCCTGAAGGACA GACATGATTTCGGATTCCCCGAGGAGGAGTTT GATGGCCACCAGTTCCAGAAGACTCAAGCCAT CTCTGTCCTCCATGAGATGATCCAGCAGACCT TCAATCTCTTCAGCACAGAGGACTCATCTGCT GCT-TGGGAACAGAGCCTCCTAGAAAAATTTTC CACT-GAACTTTACCAGCAACTGAATGACCTG GAAGCAT-GTGTGATACAGGAGGTTGGGGTGGA AGAGACTCCCCTGATGAATGTGGACTCCATC CTG-GCTGTGAGGAAATACTTCCAAAGAATC ACTCTT-TATCTAACAGAGAAGAAATACAGCCCT TGTGC-CTGGGAGGTTGTCAGAGCAGAAATCAT GAGATCCCTCTCGTTTTCAACAAACTTGCAA AAAAGATTAAGGAGGAAGGAT, and (b) a DNA seguence that on expression codes for a polypeptide coded for on expression bv either of the foregoing DNA sequences.

27. A method for producing a DNA molecule comprising a DNA sequence encoding an α-interferon, comprising the step of culturing a host cell containing a DNA molecule comprising the DNA sequence of claim 26 under conditions in which the host cell replicates DNA molecule.

* * * * *